(12) United States Patent
Botstein et al.

(10) Patent No.: US 7,118,853 B2
(45) Date of Patent: Oct. 10, 2006

(54) METHODS OF CLASSIFYING, DIAGNOSING, STRATIFYING AND TREATING CANCER PATIENTS AND THEIR TUMORS

(75) Inventors: David Botstein, Belmont, CA (US); Patrick O. Brown, Stanford, CA (US); Charles M. Perou, Carrboro, NC (US); Brian Ring, Foster City, CA (US); Douglas Ross, San Francisco, CA (US); Rob Seitz, Hampton Cove, AL (US); Jan Matthijs van de Rijn, La Henda, CA (US)

(73) Assignees: Applied Genomics, Inc., Sunnyvale, CA (US); Board of Trustees of Leland Stanford Junior University, Stanford, CA (US)

( * ) Notice: Subject to any disclaimer, the term of this patent is extended or adjusted under 35 U.S.C. 154(b) by 598 days.

(21) Appl. No.: 09/916,849

(22) Filed: Jul. 26, 2001

(65) Prior Publication Data

US 2003/0086934 A1  May 8, 2003

Related U.S. Application Data

(60) Provisional application No. 60/220,967, filed on Jul. 26, 2000.

(51) Int. Cl.
*G01N 33/50* (2006.01)
*G01N 33/53* (2006.01)
*G01N 33/536* (2006.01)
*C12Q 1/68* (2006.01)

(52) U.S. Cl. .................. 435/4; 435/6; 435/7.1; 435/7.92; 435/40.52; 436/501; 436/502; 436/536; 436/64

(58) Field of Classification Search .................. 435/4, 435/6, 7.1, 7.92, 40.52; 436/64, 501, 502, 436/536
See application file for complete search history.

(56) References Cited

U.S. PATENT DOCUMENTS 5,158,893 A * 10/1992 Hackett et al. ............ 435/7.21

FOREIGN PATENT DOCUMENTS

| WO | WO 98/21242 | * | 5/1998 |
| WO | WO 98/22139 |   | 5/1998 |
| WO | WO 99/40434 | * | 8/1999 |

OTHER PUBLICATIONS

Kerr and Thorpe (Immunochemistry LabFax, 1994, pp. 175–177).*
Schlom ("Monoclonal Antibodies: They're More and Less Than You Think", In: Molecular foundations of Oncology, 1991, pp. 95–133).*
Abstract of Vlasoff et al (Appl Immunohistochem Mol Morphol. Sep. 2002;10(3):237–41).*
Abstract of Ross and Fletcher, Stem Cells. 1998;16(6):413–28.*
Abstract of Herms et al (Int J Cancer. Sep. 2000;89(5):395–402).*
Abstract of Matsumoto et al (Int J Colorectal Dis. Jul. 1993;8(2):103–5).*
Aas, et al., "Specific P53 Mutations are Associated with De Novo Resistance to Doxorubicin in Breast Cancer Patients", *Nat. Med.* 2: 811–814, 1996.
Abbas, A. K., Lichtman, A. H. & Pober, J. S. Cellular and Molecular Immunology (Saunders, Philadelphia, 1991.
Alizadeh, et al., "Distinct Types of Diffuse Large B–Cell Lymphoma Identified by Gene Expression Profiling", *Nature*, 403(6769): 503–511, 2000.
Alon, et al., "Broad Patterns of Gene Expression Revealed by Clustering Analysis of Tumor and Normal Colon Tissues Probed by Oligonucleotide Arrays", *Proc. Natl. Acad Sci USA*, 96: 6745–6750, 1999.
Anderson, et al., "Prognostic Significance of TP53 Alterations in Breast Carcinoma", *Br. J. Cancer*, 68:540–548, 1993.
Baxa, C. A. et al. Human Adipocyte Lipid–Binding Protein: Purification of the Protein and Cloning of its Complementary DNA, *Biochemistry*, 28:8683–8690, 1989.
Berns, E. M. et al. Prevalance of Amplification of the Oncogenes c–myc, HER2/neu, and int–2 in one thousand human breast tumours: correlation with steroid receptors, *Eur J Cancer*, 28, 697–700, 1992.
Bhargava, V., Kell, D. L., van de Rijn, M. & Warnke, R. A. Bcl–2 Immunoreactivity in Breast Carcinoma Correlates with Hormone Receptor Positivity *Am J Pathol*, 145:535–540, 1994.

(Continued)

*Primary Examiner*—Karen A. Canella
(74) *Attorney, Agent, or Firm*—Choate, Hall & Stewart LLP

(57) ABSTRACT

The invention provides a variety of reagents for use in the diagnosis and management of breast cancer. The invention utilizes cDNA microarray technology to identify genes whose expression profile across a large group of tumor samples correlates with that of cytokeratin 5 and cytokeratin 17, markers for basal cells of the normal mammary lactation gland. The invention demonstrates that tumors that express cytokeratin 5/6 and/or 17 have a poor prognosis relative to tumors overall. The invention provides basal marker genes and their expression products and uses of these genes for diagnosis of breast cancer and for identification of therapies for breast cancer. In particular, the invention provides basal marker genes including cadherin3, matrix metalloproteinase 14, and cadherin EGF LAG seven-pass G-type receptor 2. The invention provides antibodies to the polypeptides expressed by these genes and methods of use thereof.

46 Claims, 15 Drawing Sheets

(5 of 15 Drawing Sheet(s) Filed in Color)

OTHER PUBLICATIONS

Cahill, et al., Mutations of Mitotic Checkpoint Genes in Human Cancers, *Nature*, 392, 300–303, 1998.

Cho, et al., "A Genome–Wide Transcriptional Analysis of the Mitotic Cell Cycle", *Mol Cell*, 2:65–73, 1998.

Chu, et al., "The Transcriptional Program of Sporulation in Budding Yeast", *Science*, 282: (5393): 1421, 1998, *Science*, 282: 699–705, 1998.

Dairkee, S. H., Mayall, B. H., Smith, H. S. & Hackett, A. J. Monoclonal marker that predicts early recurrence of breast cancer,*Lancet*, 1:514, 1987.

Dairkee, S. H., Puett, L. & Hackett, A. J. Expression of Basal and Luminal Epithelium–Specific Keratins in Normal, Benign, and Malignant Breast Tissue, *J Natl Cancer Inst*, 80:691–695,1988.

DeRisi, et al., "Exploring the Metabolic and Genetic Control of Gene Expression on a Genomic Scale", *Science*, 278: 680–686, 1997.

Eisen, et al., "DNA Arrays for Analysis of Gene Expression", *Methods Enzymol*, 303, 179–205, 1999.

Eisen, et al., "Cluster Analysis and Display of Genome–Wide Expression Patterns", *Proc. Natl. Acad Sci USA*, 95: 14863–14868, 1998.

Farnbrough, et al., "Diverse Signaling Pathways Activated by Growth Factor Receptors Induce Broadly Overlapping, Rather than Independent, Sets of Genes", *Cell*, 97:727–741, 1999.

Galitski, et al., "Ploidy Regulation of Gene Expression", *Science*, 285:251–254, 1999.

Golub, et al., "Molecular Classification of Cancer: Class Discovery and Class Prediction by Gene Expression Monitoring", *Science*, 286: 531–537, 1999.

Guelstein, V. I. et al. Monoclonal antibody mapping of keratins 8 and 17 and of vimentin in normal human mammary gland, benign tumors, dysplasias and breast cancer *Int J Cancer*,42, 147–153, 1988.

Guerin, M., Barrois, M., Terrier, M. J., Spielmann, M. & Riou, G. Overexpression of Either c–myc or c–erbB–2/Neu Proto–Oncogenes in Human Breast Carcinomas: Correlation with Poor Prognosis, *Oncogene Res*, 3: 21–31, 1988.

Gusterson, B. A. et al. Distribution of myoepithelial cells and basement membrane proteins in the normal breast and in benign and malignant breast diseases, *Cancer Res*,42:4763–4770 1982.

Heintz, N. H., Leslie, K. O., Rogers, L. A. & Howard, P. L. Amplification of the c–erb B–2 Oncogene and Prognosis of Breast Adenocarcinoma, *Arch Pathol Lab Med*, 114:160–163, 1990.

Hoch, R. V., Thompson, D. A., Baker, R. J. & Weigel, R. J. GATA–3 is Expressed in Association with Estrogen Receptor in Breast Cancer *Int J Cancer*, 84:122–128, 1999.

Iyer, et al., "The Transcriptional Program in the Response of Human Fibroblasts to Serum", *Science*, 283: 83–87, 1999.

Khan, et al., "Gene Expression Profiling of Alveolar Rhabdomyosarcoma with cDNA Microarrays", *Cancer Res*, 58: 5009–5013, 1998.

Leek, R. D., Kaklamanis, L., Pezzella, F., Gatter, K. C. & Harris, A. L. bcl–2 in Normal Human Breast and Carcinoma, Association with Oestrogen Receptor–Positive, Epidermal Growth Factor Receptor–Negative Tumours and in Situ Cancer, *Br J Cancer*, 69:135–139,1994.

Lengauer, et al., "Genetic Instabilities in Human Cancers", *Nature Genetics*, 24(3):227–235, 2000.

Li, et al., "Identification of a Human Mitotic Checkpoint Gene: hsMAD2", *Science*, 274: 246–248, 1996.

Malzahn, K., Mitze, M., Thoenes, M. & Moll, R. Biological and Prognostic Significance of Stratified Epithelial Cytokeratins in Infiltrating Ductal Breast Carcinomas, *Virchows Arch*, 433: 119–129,1998.

Miettinen, M., Lindenmayer, A. E. & Chaubal, A. Endothelial Cell Markers CD31, CD34, and BNH9 Antibody to H– and Y– Antigens—Evaluation of Their Specificity and Sensitivity in the Diagnosis of Vascular Tumors and Comparison with Von Willebrand Factor, *Mod Pathol*, 7:82–90 1994.

Moog–Lutz, C. et al. MLN64 Exhibits Homology with the Steroidogenic Acute Regulatory Protein (STAR) and is Over–Expressed in Human Breast Carcinomas *Int J Cancer*, 71:183–191,1997.

Nagle, R. B. et al. Characterization of breast carcinomas by two monoclonal antibodies distinguishing myoepithelial from luminal epithelial cells, *J Histochem Cytochem*, 34:869–881 1986.

Osborne, et al., "The Value of Estrogen and Progesterone Receptors in the Treatment of Breast Cancer", *Cancer*, 46: 2884–2888, 1980.

Pauletti, G., Godolphin, W., Press, M. F. & Slamon, D. J. Detection and Quantitation of HER–2/neu Gene Amplification in Human Breast Cancer Archival Material using Fluorescence in Situ Hybridization, *Oncogene*, 13:63–72, 1996.

Perou, et al., "Distinctive Gene Expression Patterns in Human Mammary Epithelial Cells and Breast Cancers". *Proc. Natl Acad Sci USA*, 96:9212–9217, 1999.

Pollack, J. R. et al. Genome–Wide Analysis of DNA Copy–Number Changes Using cDNA Microarrays, *Nat Genet*, 23: 41–46, 999.

Prud'homme, J. F. et al. Cloning of a Gene Expressed in Human Breast Cancer and Regulated by Estrogen in MCF–7 cells, *Dna* 4:11–21,1985.

Ronnov–Jessen, et al., "Cellular Changes Involved in Conversion of Normal to Malignant Breast; Importance of the Stromal Reaction", *Physiol, Rev*, 76:69–125, 1996.

Ross, et al., "Systemic Variation in Gene Expression Patterns in Human Cancer Cell Lines", *Nature Genetics*, 24(3):227–235, 2000.

Slamon, et al., Studies of the HER–2/Neu Proto–Oncogene In Human Breast and Ovarian Cancer, *Science*, 244: 707–712, 1989.

Stein, D. et al. The SH2 Domain Protein GRB–7 is Co–amplified, Overexpressed and in a Tight Complex with HER2 in Breast Cancer, *Embo*, J13: 1331–1340, 1994.

Spellman, PT, et al., Comprehensive identification of cell cycle–regulated genes of the yeast *Saccharomyces cerevisiae* by microarray hybridization, *Mol Biol Cell*, 9(12):3273–97, 1998.

Tavassoli, et al., "Pathology of the Breast", (Elsevier, New York, 1992).

Tontonoz, P., Hu, E., Graves, R. A., Budavari, A. I. & Spiegelman, B. M. mPPAR Gamma 2: Tissue–Specific Regulator of an Adipocyte Enhancer, *Genes Dev*, 8:1224–1234, 1994.

Wang, K. et al., Monitoring gene expression profile changes in ovarian carcinomas using cDNA microarray, *Gene*, 229:101–108, 1999.

Wolf, G. et al. Prognostic Significance of Polo–Like Kinase (PLK) Expression in Non–Small Cell Lung Cancer. *Oncogene*, 14: 543–549 1997.

Yang, G. P., Ross, D. T., Kuang, W. W., Brown, P. O. & Weigel, R. J. Combining SSH and cDNA Microarrays for Rapid Identification of Differentially Expressed Genes, *Nucleic Acids Res* 27:1517–1523,1999.

Zhou, H. et al. Tumour Amplified Kinase STK15/BTAK Induces Centrosome Amplification, Aneuploidy and Transformation. *Nat Genet*, 20: 189–193, 1998.

Han, et al.. "Distinct Cadherin Profiles in Special Variant Carcinomas and Other Tumors of the Breast", *Hum Pathol*, 30: 1035–1039, 1999.

Shimoyama, et al., "Cadherin Cell–Adhesion Molecules in Human Epithelial Tissues and Carcinomas", *Cancer Research*, 49: 2128–2133, 1989.

Soler, et al., "P–Cadherin Expression in Breast Carcinoma Indicates Poor Survival", *Cancer*, 86: 1263–1272, 1999.

Takimoto, et al., "Clinical Applications of the Camptothecins", *Biochimica et Biophysica Acta*, 1400: 107–119, 1998.

Internal Search Report issued for corresponding PCT application PCT/US01/23843.

* cited by examiner

FIG. 1A

Sequence of cadherin 3 (GenBank accession number NP_001784)
SEQ ID NO:1

MGLPRGPLASLLLLQVCWLQCAASEPCRAVFREAEVTLEAGGAEQEPGQALGK
VFMGCPGQEPALFSTDNDDFTVRNGETVQERRSLKERNPLKIFPSKRILRRHKRD
WVVAPISVPENGKGPFPQRLNQLKSNKDRDTKIFYSITGPGADSPPEGVFAVEKE
TGWLLLNKPLDREEIAKYELFGHAVSENGASVEDPMNISIIVTDQNDHKPKFTQD
TFRGSVLEGVLPGTSVMQVTATDEDDAIYTNGVVAYSIHSQEPKDPHDLMFTI
HRSTGTISVISSGLDREKVPEYTLTIQATDMDGDGSTTAVAVVEILDANDNAPM
FDPQKYEAHVPENAVGHEVQRLTVTDLDAPNSPAWRATYLIMGGDDGDHFTITT
HPESNQGILTTRKGLDFEAKNQHTLYVEVTNEAPFVLKLPTSTATIVVHVEDVNE
APVFVPPSKVVEVQEGIPTGEPVCVYTAEDPDKENQKISYRILRDPAGWLAMDPD
SGQVTAVGTLDREDEQEFVRNNIYEVMVLAMDNGSPPTTGTGTLLLTLIDVNDHG
PVPEPRQITICNQSPVRHVLNITDKDLSPHTSPFQAQLTDDSDIYWTAEVNEEGDT
VVLSLKKFLKQDTYDVHLSLSDHGNKEQLTVIRATVCDCHGHVETCPGPWKGG
FILPVLGAVLALFLLLVLLLVRKKRKIKEPLLLPEDDTRDNVFYYGEEGGEE
DQDYDITQLHRGLEARPEVVLRNDVAPTIIPTPMYRPRPANPDEIGNFIIENLKAA
NTDPTAPPYDTLLVFDYEGSGSDAASLSSLTSSASDQDQDYDYLNEWGSRFKKL
ADMYGGGEDD

FIG. 1B

Sequence of matrix metalloproteinase 14
(GenBank accession number NP_004986)

SEQ ID NO:2

MSPAPRPPRCLLLPLLTLGTALASLGSAQSSSFSPEAWLQQYGYLPPGDLRTHTQ
RSPQSLSAAIAAMQKFYGLQVTGKADADTMKAMRRPRCGVPDKFGAEIKANVR
RKRYAIQGLKWQHNEITFCIQNYTPKVGEYATYEAIRKAFRVWESATPLRFREVP
YAYIREGHEKQADIMIFFAEGFHGDSTPFDGEGGFLAHAYFPGPNIGGDTHFDSA
EPWTVRNEDLNGNDIFLVAVHELGHALGLEHSSDPSAIMAPFYQWMDTENFVLP
DDDRRGIQQLYGGESGFPTKMPPQPRTTSRPSVPDKPKNPTYGPNICDGNFDTVA
MLRGEMFVFKERWFWRVRNNQVMDGYPMPIGQFWRGLPASINTAYERKDGKF
VFFKGDKHWVFDEASLEPGYPKHIKELGRGLPTDKIDAALFWMPNGKTYFFRGN
KYYRFNEELRAVDSEYPKNIKVWEGIPESPRGSFMGSDEVFTYFYKGNKYWKFN
NQKLKVEPGYPKSALRDWMGCPSGGRPDEGTEEETEVIIIEVDEEGGGAVSAAA
VVLPVLLLLLVLAVGLAVFFFRRHGTPRRLLYCQRSLLDKV

FIG.1C-1

Sequence of cadherin EGF LAG seven-pass G-type receptor 2
(GenBank accession number NP_001399)

SEQ ID NO:3

MRSPATGVPLPTPPPLLLLLLLPPPLLGDQVGPCRSLGSRGRGSSGACAPMG
WLCPSSASNLWLYTSRCRDAGTELTGHLVPHHDGLRVWCPESEAHIPLPPAPEG
CPWSCRLLGIGGHLSPQGKLTLPEEHPCLKAPRLRCQSCKLAQAPGLRAGERSPE
ESLGGRRKRNVNTAPQFQPPSYQATVPENQPAGTPVASLRAIDPDEGEAGRLEYT
MDALFDSRSNQFFSLDPVTGAVTTAEELDRETKSTHVFRVTAQDHGMPRRSALA
TLTILVTDTNDHDPVFEQQEYKESLRENLEVGYEVLTVRATDGDAPPNANILYRL
LEGSGGSPSEVFEIDPRSGVIRTRGPVDREEVESYQLTVEASDQGRDPGPRSTTAA
VFLSVEDDNDNAPQFSEKRYVVQVREDVTPGAPVLRVTASDRDKGSNAVVHYSI
MSGNARGQFYLDAQTGALDVVSPLDYETTKEYTLRVRAQDGGRPPLSNVSGLV
TVQVLDINDNAPIFVSTPFQATVLESVPLGYIVLHVQAIDADAGDNARLEYRLAG
VGHDFPFTINNGTGWISVAAELDREEVDFYSFGVEARDHGTPALTASASVSVTVL
DVNDNNPTFTQPEYTVRLNEDAAVGTSVVTVSAVDRDAHSVITYQITSGNTRNR
FSITSQSGGGLVSLALPLDYKLERQYVLAVTASDGTRQDTAQIVVNVTDANTHRP
VEQSSHYTVNVNEDRPAGTTVVLISATDEDTGENARITYFMEDSIPQFRIDADTG
AVTTQAELDYEDQVSYTLAITARDNGIPQKSDTTYLEILVNDVNDNAPQFLRDSY
QGSVYEDVPPFETSVLQISATDRDSGLNGRVFYTFQGGDDGDFIVESTSGIVRT
LRRLDRENVAQYVLRAYAVDKGMPPARTPMEVTVTLVDVNDNPPVFEQDEFDV

TO FIG.1C-2

FROM FIG.1C-1

FIG.1C-2

FVEENSPIGLAVARVTATDPDEGTNAQIMYQIVEGNIPEVFQLDIFSGELTALVDL
DYEDRPEYVLVIQATSAPLVSRATVHVRLLDRNDNPPVLGNFEILFNNYVTNRSS
SFPGGAIGRVPAHDPDISDSLTYSFERGNELSIVLLNASTGELKLSRALDNNRPLE
AIMSVLVSDGVHSVTAQCALRVTIITDEMLTHSITLRLEDMSPERFLSPLLGLFIQA
VAATLATPPDHVVVFNVQRDTDAPGGHILNVSLSVGQPPGPGGGPPFLPSEDLQE
RLYLNRSLLTAISAQRVLPFDDNICLREPCENYMRCVSVLRFDSSAPFIASSSVLFR
PIHPVGGLRCRCPPGFTGDYCETEVDLCYSRPCGPHGRCRSREGGYTCLCRDGYT
GEHCEVSARSGRCTPGVCKNGGTCVNLLVGGFKCDCPSGDFEKPYCQVTTRSFP
AHSFITFRGLRQRFHFTLALSFATKERDGLLYNGRFNEKHDFVALEVIQEQVQL
TFSAGESTTTVSPFVPGGVSDGQWHTVQLKYYNKPLLGQTGLPQGPSEQKVAVV
TVDGCDTGVALRFGSVLGNYSCAAQGTQGGSKKSLDLTGPLLLGGVPDLPESFP
VRMRQFVGCMRNLQVDSRHIDMADFIANNGTVPGCPAKKNVCDSNTCHNGGT
CVNQWDAFSCECPLGFGGKSCAQEMANPQHFLGSSLVAWHGLSLPISQPWYLSL
MFRTRQADGVLLQAITRGRSTITLQLREGHVMLSVEGTGLQASSLRLEPGRAND
GDWHHAQLALGASGGPGHAILSFDYGQQRAEGNLGPRLHGLHLSNITVGGIPGP
AGGVARGFRGCLQGVRVSDTPEGVNSLDPSHGESINVEQGCSLPDPCDSNPCPA
NSYCSNDWDSYSCSCDPGYYGDNCTNVCDLNPCEHQSVCTRKPSAPHGYTCEC
PPNYLGPYCETRIDQPCPRGWWGHPTCGPCNCDVSKGFDPDCNKTSGECHCKEN

TO FIG.1C-3

FROM FIG.1C-2

FIG.1C-3

HYRPPGSPTCLLCDCYPTGSLSRVCDPEDGQCPCKPGVIGRQCDRCDNPFAEVTT
NGCEVNYDSCPRAIEAGIWPRTRFGLPAAAPCPKGSFGTAVRHCDEHRGWLPP
NLFNCTSITFSELKGFAERLQRNESGLDSGRSQQLALLLRNATQHTAGYFGSDVK
VAYQLATRLLAHESTQRGFGLSATQDVHFTENLLRVGSALLDTANKRHWELIQQ
TEGGTAWLLQHYEAYASALAQNMRHTYLSPFTIVTPNIVISVVRLDKGNFAGAK
LPRYEALRGEQPPDLETTVILPESVFRETPPVVRPAGPGEAQEPEELARRQRRHPE
LSQGEAVASVIIYRTLAGLLPHNYDPDKRSLRVPKRPIINTPVVSISVHDDEELLPR
ALDKPVTVQFRLLETEERTKPICVFWNHSILVSGTGGWSARGCEVVERNESHVSC
QCNHMTSFAVLMDVSRRENGEILPLKTLTYVALGVTLAALLLTFFFLTLRILRS
NQHGIRRNLTAALGLAQIVFLLGINQADLPFACTVIAILLHFLYLCTFSWALLEAL
HLYRALTEVRDVNTGPMRFYYMLGWGVPAFITGLAVGLDPEGYGNPDFCWLSI
YDTLIWSFAGPVAFAVSMSVFLYILAARASCAAQRQGFEKKGPVSGLQPSFAVLL
LLSATWLLALLSVNSDTLLFHYLFATCNCIQGPFIFLSYVVLSKEVRKALKLACSR
KPSPDPALTTKSTLTSSYNCPSPYADGRLYQPYGDSAGSLHSTSRSGKSQPSYIPF
LLREESALNPGQPPGLGDPGSLFLEGQDPQHDPDTDSDSDLSLEDDQSGSYAST
HSSDSEEEEEEEAAFPGEQGWDSLLGPGAERLPLHSTPKDGGPGPGKAPWPG
DFGTTAKESSGNGAPEERLRENGDALSREGSLGPLPGSSAQPHKGILKKKCLPTIS
EKSSLLRLPLEQCTGSSRGSSASEGSRGGPPPRPPPRQSLQEQLNGVMPIAMSIKA
GTVDEDSSGSEFLFNFLH

FIG. 1D

Peptides for antibodies that bind to cadherin3
(GenBank accession number NP_001784):

RAVFREAEVTLEAGGAEQE (SEQ ID NO:4)

QEPALFSTDNDDFTVRN (SEQ ID NO:5)

QKYEAHVPENAVGHE (SEQ ID NO:6)

Peptides for antibodies that bind to matrix metalloproteinase 14
(GenBank accession number NP_004986):

AYIREGHEKQADIMIFFAE (SEQ ID NO:7)

DEASLEPGYPKHIKELGR (SEQ ID NO:8)

RGSFMGSDEVFTYFYK (SEQ ID NO:9)

Peptides for antibodies that bind to anti-cadherin EGF LAG seven-pass
G-type receptor 2 (GenBank accession number NP_001399):

QASSLRLEPGRANDGDWH (SEQ ID NO:10)

ELKGFAERLQRNESGLDSGR (SEQ ID NO:11)

RSGKSQPSYIPFLLREE (SEQ ID NO:12)

Peptides for antibodies that bind to anti-cytokeratin 17:

KKEPVTTRQVRTIVEE (SEQ ID NO:13)

QDGKVISSREQVHQTTR (SEQ ID NO:14)

SSSIKGSSGLGGGSS (SEQ ID NO:15)

Intrinsic Gene Subset

Epithelial-Enriched Gene Subset

FIG.3A 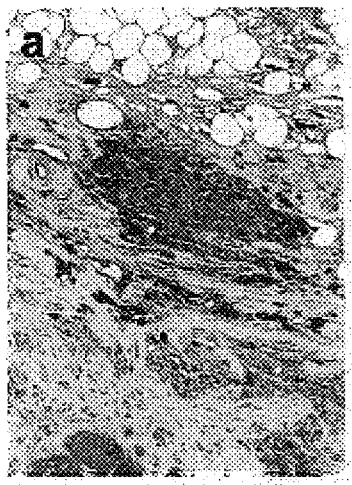 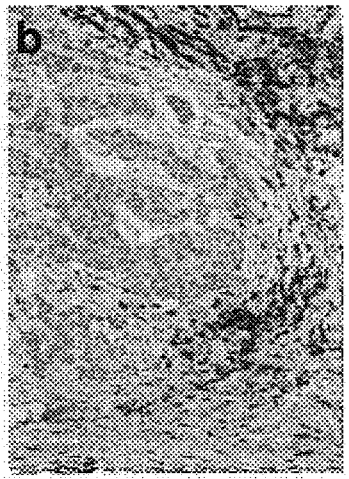 FIG.3B
FIG.3C   FIG.3D
FIG.3E 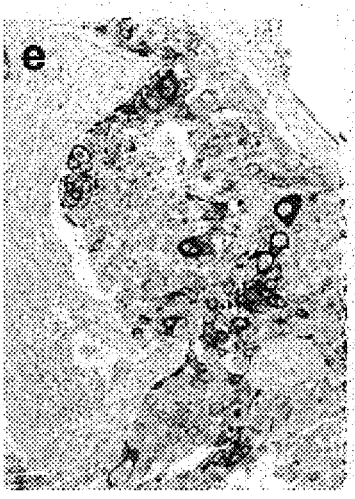 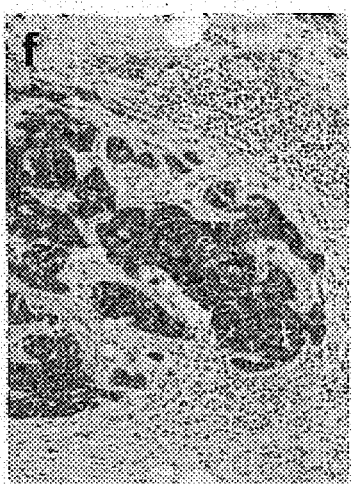 FIG.3F FIG. 6A ck5/6
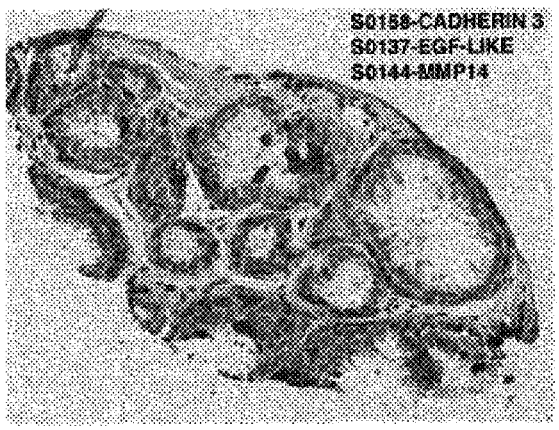
FIG. 6B s0158
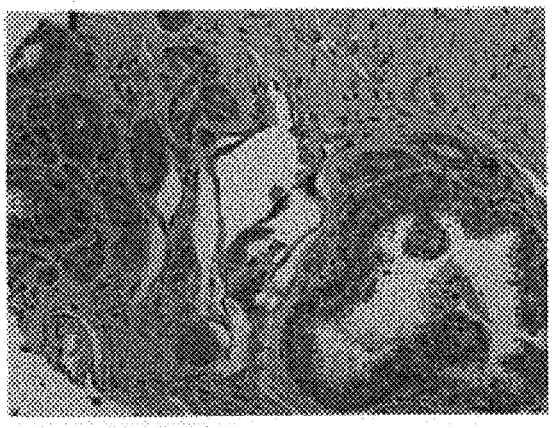
FIG. 6C s0137
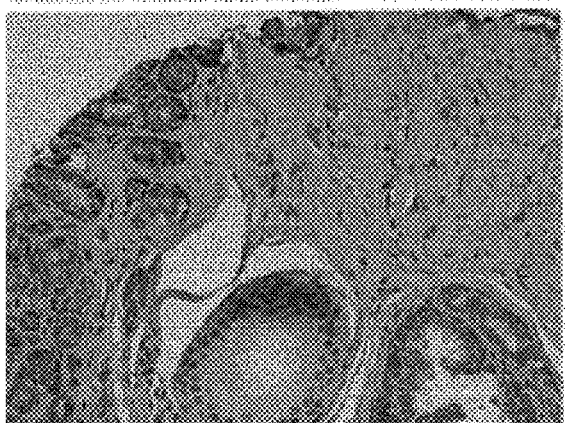
FIG. 6D s0144
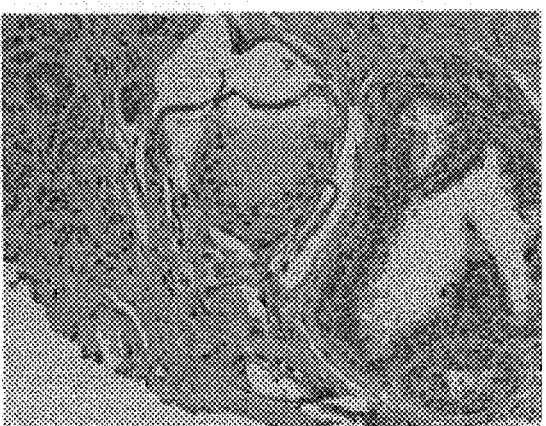

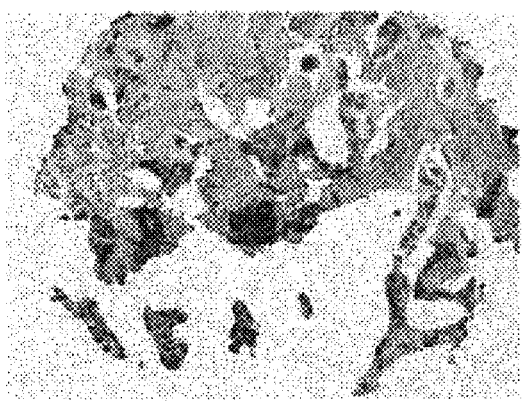
FIG. 7A CK5/6
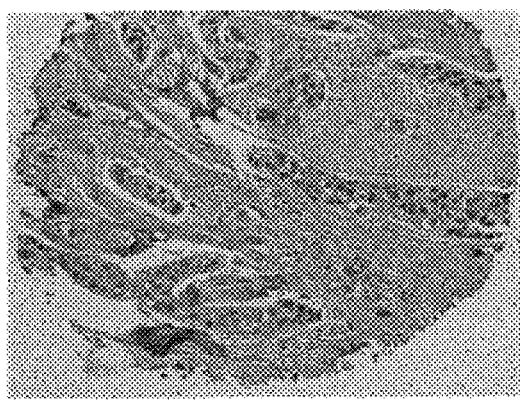
FIG. 7B S0137
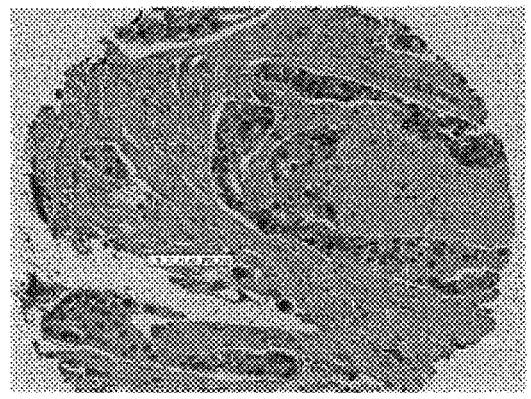
FIG. 7C S0158

METHODS OF CLASSIFYING, DIAGNOSING, STRATIFYING AND TREATING CANCER PATIENTS AND THEIR TUMORS

CROSS-REFERENCE TO RELATED APPLICATIONS

This application claims priority to provisional application U.S. Ser. No. 60/220,967, filed Jul. 26, 2000, which is incorporated herein by reference.

GOVERNMENT SUPPORT

The U.S. Government has a paid-up license in this invention and the right in limited circumstances to require the patent owner to license others on reasonable terms as provided for by the terms of Grant No. NIH CA 77097 awarded by the National Cancer Institute.

REFERENCE TO MATERIAL PRESENTED IN APPENDICES

This patent application refers to material comprising tables and data presented as appendices on CD-ROM. The 24 files on the accompanying CD-ROM are entitled Appendix A (4,651 kb), Appendix B (481 kb), Appendix C (7,810 kb), Appendix D (3,721 kb), Appendix E (1238 kb), Appendix F (540 kb), Appendix G (377 kb), AppendixH_Table1 (2,102 kb), AppendixH_Table2 (760 kb), AppendixH_Table3 (22 kb), AppendixH_Table4 (25 kb) AppendixH_Table5 (27 kb), AppendixH_Table6 (655 kb), AppendixH_Table7 (88 kb) AppendixH_Table8 (28 kb), AppendixH_Table9-1 (22 kb), AppendixH_Table9-2 (22 kb) AppendixH_Table10 (21 kb), AppendixH_Table11 (22 kb), AppendixH_Table12 (23 kb) AppendixH_Table13 (21 kb), AppendixH_Table14 (23 kb), AppendixH_Table15 (21 kb), AppendixH_Table16 (21 kb). The size of each file in kilobytes is listed following the file name. The total number of bytes is 23,164,507. All files were created on Jul. 25, 2001. The format is IBM-PC. The operating system is Windows. The 24 files on the CD-ROM are incorporated herein by reference.

BACKGROUND OF THE INVENTION

A major challenge of cancer treatment is to target specific therapies to distinct tumor types in order to maximize efficacy and minimize toxicity. A related challenge lies in the attempt to provide accurate diagnostic, prognostic, and predictive information. At present, tumors are described with the tumor-node-metastasis (TNM) system. This system, which uses the size of the tumor, the presence or absence of tumor in regional lymph nodes, and the presence or absence of distant metastases, to assign a stage to the tumor is described in the American Joint Committee on Cancer: AJCC Cancer Staging Manual. Philadelphia, Pa.: Lippincott-Raven Publishers, 5th ed., 1997, pp 171–180, and in Harris, J R: "Staging of breast carcinoma" in Harris, J. R., Hellman, S., Henderson, I. C., Kinne D. W. (eds.): *Breast Diseases*. Philadelphia, Lippincott, 1991. The assigned stage is used as a basis for selection of appropriate therapy and for prognostic purposes. In addition to the TNM parameters, morphologic appearance is used to further classify tumors and thereby aid in selection of appropriate therapy. However, this approach has serious limitations. Tumors with similar histopathologic appearance can exhibit significant variability in terms of clinical course and response to therapy. For example, some tumors are rapidly progressive while others are not. Some tumors respond readily to hormonal therapy or chemotherapy while others are resistant.

Assays for cell surface markers, e.g., using immunohistochemistry, have provided means for dividing certain tumor types into subclasses. For example, one factor considered in prognosis and in treatment decisions for breast cancer is the presence or absence of the estrogen receptor (ER) in tumor samples. ER-positive breast cancers typically respond much more readily to hormonal therapies such as tamoxifen, which acts as an anti-estrogen in breast tissue, than ER-negative tumors. Though useful, these analyses only in part predict the clinical behavior of breast tumors. There is phenotypic diversity present in breast cancers that current diagnostic tools fail to detect. Therefore, there exists a need for improved methods for classifying tumors.

Mutation or dysregulation of any of a large number of genes contributes to the development and progression of cancer as discussed in Hanahan, D. and Weinberg, R., The Hallmarks of Cancer, *Cell*, 100, 57–70, 2000. Genes that play a role in cancer can be divided into a number of broad classes including oncogenes, tumor suppressor genes, and genes that regulate apoptosis. Oncogenes such as ras typically encode proteins whose activities promote cell growth and/or division, a function that is necessary for normal physiological processes such as development, tissue regeneration, and wound healing. However, inappropriate activity or expression of oncogenes can lead to the uncontrolled cell proliferation that is a feature of cancer. Tumor suppressor genes such as Rb act as negative regulators of cell proliferation. Loss of their activity, e.g., due to mutations or decreased expression at the level of mRNA or protein, can lead to unrestrained cell division. A number of familial cancer syndromes and inherited susceptibility to cancer are believed to be caused by mutations in tumor suppressor genes. Apoptosis, or programmed cell death, plays important roles both in normal development and in surveillance to eliminate cells whose survival may be deleterious to the organism, e.g., cells that have acquired DNA damage. Many chemotherapeutic agents are believed to work by activating the endogenous apoptosis pathway in tumor cells.

Although a substantial number of genes have been implicated as playing important roles in cancer, the factors responsible for the phenotypic diversity of tumors remain largely unknown. In particular, understanding of the underlying differences in gene expression that may contribute to tumor phenotype is limited. Understanding the differences in gene expression between normal and cancerous tissue and between different tumors of the same tissue type is of significant diagnostic, prognostic, and therapeutic utility. There is therefore a need for the identification of genes exhibiting differential expression between tumors. In particular, there is a need for the identification of additional genes and proteins that can be used to classify tumors, especially genes and proteins that can provide diagnostic, prognostic, and/or predictive information in cancer. There is also a need for antibodies and other reagents for the detection and measurement of such genes and proteins.

Most of the commonly used chemotherapeutic agents act relatively nonselectively. Rather than specifically killing tumor cells, these agents target any dividing cell, resulting in a variety of adverse effects. In addition, current therapeutic strategies are of limited efficacy, and the mortality rate of breast cancer remains high. There is therefore a need for the identification of additional genes and proteins that can be used as targets for the treatment of cancer. There is also a need for antibodies and other reagents that can modulate, regulate, or interact with these genes and proteins to provide new method of treatment for cancer.

SUMMARY OF THE INVENTION

The present invention relates to the identification of markers that are useful in classifying tumors, particularly breast tumors. The markers identify a class of tumors whose cells have characteristics of basal cells of normal breast lactation ducts. The markers were identified based on their expression profiles in human breast tumor samples, normal breast tissue, and cell lines as assessed using cDNA microarrays. In particular, the basal cell markers of the present invention were identified based on the similarity of their mRNA expression patterns to the expression patterns of markers previously known to identify breast duct basal cells, e.g., cytokeratin 5 and cytokeratin 17, across a set of breast tumor samples. The basal markers include the three genes known as cadherin 3 or P-cadherin (SEQ ID NO:1; GenBank protein accession number NP_001784; GenBank cDNA accession number NM_001793), matrix metalloproteinase 14 (SEQ ID NO:2; GenBank protein accession number NP_004986; GenBank cDNA accession number NM_004995); and cadherin EGF LAG seven-pass G-type receptor 2 or EGF-Like Domain, Multiple 2 (SEQ ID NO:3; GenBank protein accession number NP_001399; GenBank cDNA accession number NM_001408). The invention further provides antibodies that specifically bind to the polypeptides encoded by the basal marker genes identified herein. The antibodies recognize basal cells of normal mammary lactation glands.

The invention provides various diagnostic methods based on the reagents mentioned above. The diagnostic methods include methods for classifying a tumor. In particular, the invention allows classification of a breast tumor as belonging to a basal class of breast tumors. According to certain of the inventive methods the presence or amount of a gene product, e.g., a polypeptide or a nucleic acid, encoded by a basal marker gene is detected in a sample derived from a subject (e.g., a sample of tissue or cells obtained from a tumor or a blood sample obtained from a subject). In general the subject is a human, however the subject may also be an animal of any other kind. The subject may be an individual who has or may have a tumor. The sample may be subjected to various processing steps prior to or in the course of detection. In certain embodiments of the invention the gene product is a polypeptide that is detected using an antibody capable of binding to the polypeptide. In certain embodiments of the invention the antibody is used to perform immunohistochemical staining on a sample obtained from a subject. In certain embodiments of the invention basal marker gene mRNA expression is measured using a microarray. In other embodiments of the invention basal marker gene mRNA expression is measured by quantitative PCR using a set of primers designed to amplify a portion of the gene. Additional detection means that may be employed in the present invention are described in U.S. Pat. No: 6,057,105. In any of the methods for tumor classification and diagnosis, it may be advantageous to detect and/or measure expression of a set of basal markers rather than expression of a single marker.

By providing reagents that may reliably be used to classify tumors as belonging to a basal subclass, the invention enables a variety of methods for improving therapeutic options for patients with breast cancer. Much effort has and continues to be expended on the discovery of new chemotherapeutic agents. These agents are tested for efficacy in clinical trials. In many such trials it is noticed that a small number of patients stabilize or improve while receiving the treatment, while most patients do not appear to benefit. Most such agents are not further developed for a number of reasons. For example, the clinical trial results may not be adequate to gain approval by the Food and Drug Administration. In addition, a pharmaceutical company may determine that the potential market for the drug is too small to justify further efforts. However, if it were possible to identify those patients likely to respond to the treatment, then it would be possible to design clinical trials that would show efficacy, and it would be possible to appropriately select patients who would benefit from the treatment. In addition, the availability of markers that can be used to classify breast tumors enables the retrospective examination of the thousands of breast tumor samples archived in hospitals and pathology labs. These samples can be classified using the inventive reagents and classification scheme, and the results can be correlated with the clinical outcome, based on medical records. Thus it is possible to determine whether tumors that fall into a particular tumor class, e.g., a basal tumor class, are responsive to a particular treatment. This will enable the re-evaluation of drugs that failed in clinical trials and may identify a subset of tumors that are likely to respond to a particular drug, and thus a subset of patients that are likely to benefit from treatment with that drug.

The inventors have recognized that in order to achieve these goals it is necessary to develop new and improved methods for classifying breast tumors. The inventive methods provide a molecular basis for classifying tumors, based on their underlying biology. While not wishing to be bound by any theory, the inventors postulate that tumors arising from a particular cell type within the breast are likely to display common features. Such features may include the prognosis (e.g., predicted survival time or likelihood that a patient's life expectancy exceeds a given length of time) or likelihood that a tumor will respond to a particular therapy.

In particular, tumors that display characteristics of basal cells of the normal breast lactation duct (also referred to herein as breast basal cells) form a distinct subclass (referred to herein as the basal subclass). Inventors have confirmed that patients with breast tumors whose cells display characteristics of breast basal cells, e.g., expression of cytokeratin 5 and/or cytokeratin 17, have a poor clinical outcome relative to patients with breast tumors that do not express these markers. However, antibodies to these cytokeratins have been found (by the inventors and by other investigators) to give spotty, focal staining patterns when used to perform immunohistochemistry on breast tumor samples. Thus the utility of cytokeratins 5 and 17 as markers and the utility of antibodies that bind to cytokeratin 5 or 17 for determining whether a tumor is a member of the basal subclass has been limited. The inventors have therefore identified genes whose mRNA expression profiles across a large set of tumor samples correlate with, i.e. are similar to, the expression profiles of the known basal cell markers cytokeratins 5 and 17. These genes include the basal markers of the present invention mentioned above. As described in Examples 10 and 13, the inventors have generated antibodies to the proteins expressed by these genes and shown that the antibodies stain basal cells of normal mammary lactation glands. Thus detection of one or more expression products of these genes may be used to identify tumors that fall within the basal tumor subclass.

The invention further provides therapeutic agents based on the identification of breast basal cell markers. The therapeutic agents include compounds that modulate these genes or that modulate polypeptides encoded by these genes. In particular, the therapeutic agents include antibodies that bind to polypeptides encoded by the basal cell marker genes. The invention further includes agonists and antagonists to the basal marker genes, to the polynucleotides transcribed from those genes, and to their encoded polypeptides. The invention also provides methods for identifying such agonists and antagonists. The invention further includes pharmaceutical compositions comprising such antibodies, agonists, and antagonists as well as methods of use of the pharmaceutical compositions in the treatment of cancer, particularly breast cancer.

According to one aspect, the invention provides a method of classifying a tumor comprising the steps of (i) providing a tumor sample, (ii) detecting expression or activity of a gene encoding the polypeptide of SEQ ID NO:1 in the sample; and (iii) classifying the tumor as belonging to a tumor subclass based on the results of the detecting step. The invention also provides a method of classifying a tumor comprising the steps of (i) providing a tumor sample, (ii) detecting expression or activity of a gene encoding the polypeptide of SEQ ID NO:2 in the sample, and (iii) classifying the tumor as belonging to a tumor subclass based on the results of the detecting step. In addition, the invention provides a method of classifying a tumor comprising the steps of (i) providing a tumor sample, (ii) detecting expression or activity of a gene encoding the polypeptide of SEQ ID NO:3 in the sample, and (iii) classifying the tumor as belonging to a tumor subclass based on the results of the detecting step. The invention further includes a method of classifying a tumor comprising the steps of (i) providing a tumor sample, (ii) detecting expression or activity of at least two genes selected from the group consisting of: a gene encoding the polypeptide of SEQ ID NO:1, SEQ ID NO:2, and SEQ ID NO:3 in the sample, and (iii) classifying the tumor as belonging to a tumor subclass based on the results of the detecting step. In any of the foregoing methods the detecting step may comprise detecting the polypeptide or polypeptides encoded by the genes. A variety of detection techniques may be employed including, but not limited to, immunohistochemical analysis, ELISA assay, antibody arrays, or detecting modification of a substrate by the polypeptide.

In certain embodiments of the methods the tumor is a breast tumor and the tumor subclass is a basal tumor subclass. The methods may further comprise providing diagnostic, prognostic, or predictive information based on the classifying step. Classifying may include stratifying the tumor (and thus stratifying a subject having the tumor), e.g., for a clinical trial. The methods may further comprise selecting a treatment based on the classifying step.

In another aspect, the invention provides a method of testing a subject comprising the steps of (i) providing a sample isolated from a subject, (ii) detecting expression or activity of a gene encoding the polypeptide of SEQ ID NO:1 in the sample, and (iii) providing diagnostic, prognostic, or predictive information based on the detecting step. The invention further provides a method of testing a subject comprising the steps of (i) providing a sample isolated from a subject, (ii) detecting expression or activity of a gene encoding the polypeptide of SEQ ID NO:2 in the sample (iii) and providing diagnostic, prognostic, or predictive information based on the detecting step. The invention further provides a method of testing a subject comprising the steps of (i) providing a sample isolated from a subject, (ii) detecting expression or activity of a gene encoding the polypeptide of SEQ ID NO:3 in the sample (iii) and providing diagnostic, prognostic, or predictive information based on the detecting step. The invention further includes a method of testing a subject comprising the steps of (i) providing a sample isolated from the subject, (ii) detecting expression or activity of at least two genes selected from the group consisting of: a gene encoding the polypeptide of SEQ ID NO:1, SEQ ID NO:2, and SEQ ID NO:3 in the sample, and (iii) providing diagnostic, prognostic, or predictive information based on the detecting step. In any of these methods the detecting step may comprise detecting the polypeptide or polypeptides. Detection may be performed using any appropriate technique including, but not limited to, immunohistochemistry, ELISA assay, protein array, or detecting modification of a substrate by the polypeptide.

The sample may comprise mRNA, in which case the detecting step may comprise hybridizing the mRNA or cDNA or RNA synthesized from the mRNA to a microarray or detecting mRNA transcribed from the gene or detecting cDNA or RNA synthesized from mRNA transcribed from the gene. In any of the above methods, the sample may be a blood sample, a urine sample, a serum sample, an ascites sample, a saliva sample, a cell, and a portion of tissue.

In another aspect, the invention provides a kit for diagnosis of a tumor which may include (i) primers for amplifying an mRNA transcribed from a gene that encodes the polypeptide of any of SEQ ID NO:1, SEQ ID NO:2; and SEQ ID NO:3 (ii) instructions for use of the kit; and/or (iii) control samples for testing the primers, wherein the control samples comprise nucleic acids that hybridize to the primers.

In another aspect, the invention provides an antibody that specifically binds to an epitope found in a polypeptide whose amino acid sequence comprises the amino acid sequence of SEQ ID NO:1, and wherein the antibody recognizes basal cells in normal mammary lactation glands. According to certain embodiments of the invention the antibody distinguishes basal cells from luminal cells in normal mammary lactation gland. According to certain embodiments of the invention the antibody recognizes an epitope found in a peptide having an amino acid sequence selected from the group consisting of SEQ ID NO:4, SEQ ID NO:5, and SEQ ID NO:6.

In another aspect, the invention provides an antibody that specifically binds to an epitope found in a polypeptide whose amino acid sequence comprises the amino acid sequence of SEQ ID NO:2, and wherein the antibody recognizes basal cells in normal mammary lactation glands. According to certain embodiments of the invention the antibody distinguishes basal cells from luminal cells in normal mammary lactation gland. According to certain embodiments of the invention the antibody recognizes an epitope found in a peptide having an amino acid sequence selected from the group consisting of SEQ ID NO:7, SEQ ID NO:8, and SEQ ID NO:9.

In another aspect, the invention provides an antibody that specifically binds to an epitope found in a polypeptide whose amino acid sequence the amino acid sequence of SEQ ID NO:3, and wherein the antibody recognizes basal cells in normal mammary lactation glands. According to certain embodiments of the invention the antibody distinguishes basal cells from luminal cells in normal mammary lactation gland. According to certain embodiments of the invention the antibody recognizes an epitope found in a peptide having an amino acid sequence selected from the group consisting of SEQ ID NO:10, SEQ ID NO:11, and SEQ ID NO:12.

The invention further provides a kit for tumor diagnosis comprising one or more of the foregoing antibodies. The kit may further include instructions for use of the kit and/or a control slide comprising breast tissue samples for testing reagents in the kit or such samples themselves.

According to another aspect, the invention provides a method of testing a compound or a combination of compounds for activity against tumors comprising steps of (i) obtaining or providing tumor samples taken from subjects who have been treated with the compound or combination of compounds, wherein the tumors fall within a tumor subclass, (ii) comparing the response rate of tumors that fall within the tumor subclass and have been treated with the compound with the overall response rate of tumors that have been treated with the compound or combination of compounds or with the response rate of tumors that do not fall within the subclass and have been treated with the compound or combination of compounds and (iii) identifying the compound or combination of compounds as having selective activity against tumors in the tumor subclass if the response rate of tumors in the subclass is greater than the overall response rate or the response rate of tumors that do not fall within the subclass. In certain embodiments of the invention the tumors are breast tumors. In certain embodiments of the invention the tumor subclass is a basal tumor subclass. The tumors may be classified according to any of the inventive classification methods described above. In certain embodiments of the invention the classification is based on expression of the polypeptide of SEQ ID NO:1, 2, 3, or a combination of these.

The invention further provides a method of testing a compound or a combination of compounds for activity against tumors comprising steps of (i) treating subjects in need of treatment for tumors with the compound or combination of compounds, (ii) comparing the response rate of tumors that fall within a tumor subclass with the overall response rate of tumors or with the response rate of tumors that do not fall within the subclass, and (iii) identifying the compound or combination of compounds as having selective activity against tumors in the tumor subclass if the response rate of tumors in the subclass is greater than the overall response rate or the response rate of tumors that do not fall within the subclass. The method may further comprise various additional steps. For example, the method may comprise steps of (i) providing tumor samples from subjects in need of treatment for tumors, (ii) determining whether the tumors fall within a tumor subclass, and (iii) stratifying the subjects based on the results of the determining step prior to performing the treating step. The method may further comprise the steps of (i) providing tumor samples from subjects in need of treatment for tumors, (ii) detecting expression or activity of a gene encoding the polypeptide of SEQ ID NO:1 in the samples, and (iii) stratifying the subjects based on the results of the detecting step prior to performing the treating step. The method may further comprise the steps of (i) providing tumor samples from subjects in need of treatment for tumors, (ii) detecting expression or activity of a gene encoding the polypeptide of SEQ ID NO:2 in the samples, and (iii) stratifying the subjects based on the results of the detecting step prior to performing the treating step. The method may further comprise the steps of (i) providing tumor samples from subjects in need of treatment for tumors, (ii) detecting expression or activity of a gene encoding the polypeptide of SEQ ID NO:3 in the samples, and (iii) stratifying the subjects based on the results of the detecting step prior to performing the treating step. The method may further comprise the steps of (i) providing tumor samples from subjects in need of treatment for tumors, (ii) detecting expression or activity of a gene encoding a polypeptide whose sequence comprises a sequence selected from the group consisting of SEQ ID NO:1, SEQ ID NO:2, and SEQ ID NO:3 in the samples, and (iii) stratifying the subjects based on the results of the detecting step prior to performing the treating step.

In addition, the invention includes a method of testing a compound or a combination of compounds for activity against tumors comprising steps of (i) treating subjects in need of treatment for tumors with the compound or combination of compounds or with an alternate compound, wherein the tumors fall within a tumor subclass, (ii) comparing the response rate of tumors treated with the compound or combination of compounds with the response rate of tumors treated with the alternate compound; and (iii) identifying the compound or combination of compounds as having superior activity against tumors in the tumor subclass, as compared with the alternate compound, if the response rate of tumors treated with the compound or combination of compounds is greater than the response rate of tumors treated with the alternate compound. The method may further comprise various additional steps. For example, the method may comprise steps of (i) providing tumor samples from subjects in need of treatment for tumors, (ii) determining whether the tumors fall within a tumor subclass, and (iii) stratifying the subjects based on the results of the determining step prior to performing the treating step. The method may further comprise the steps of (i) providing tumor samples from subjects in need of treatment for tumors, (ii) detecting expression or activity of a gene encoding the polypeptide of SEQ ID NO:1 in the samples, and (iii) stratifying the subjects based on the results of the detecting step prior to performing the treating step. The method may further comprise the steps of (i) providing tumor samples from subjects in need of treatment for tumors, (ii) detecting expression or activity of a gene encoding the polypeptide of SEQ ID NO:2 in the samples, and (iii) stratifying the subjects based on the results of the detecting step prior to performing the treating step. The method may further comprise the steps of (i) providing tumor samples from subjects in need of treatment for tumors, (ii) detecting expression or activity of a gene encoding the polypeptide of SEQ ID NO:3 in the samples, and (iii) stratifying the subjects based on the results of the detecting step prior to performing the treating step. The method may further comprise the steps of (i) providing tumor samples from subjects in need of treatment for tumors, (ii) detecting expression or activity of a gene encoding a polypeptide whose sequence comprises a sequence selected from the group consisting of SEQ ID NO:1, SEQ ID NO:2, and SEQ ID NO:3 in the samples, and (iii) stratifying the subjects based on the results of the detecting step prior to performing the treating step.

In certain embodiments of the invention the alternate compound is a compound approved by the U.S. Food and Drug administration for treatment of tumors. The invention also provides a method of treating a subject comprising steps of (i) identifying a subject as having a tumor in a basal tumor subclass, and (ii) administering to the subject a compound identified according to any of the inventive methods for identifying a subject.

In another aspect, the invention provides a method of treating a subject comprising steps of (i) providing a subject in need of treatment for cancer, (ii) administering to the subject an antibody that specifically binds to a polypeptide having an amino acid sequence comprising the sequence of SEQ ID NO:1, SEQ ID NO:2, or SEQ ID NO:3 or administering a combination of such antibodies. In certain embodiments of the invention the tumor is a breast tumor. In certain embodiments of the invention the antibody is conjugated with a toxic molecule.

The invention further provides a method of treating a subject comprising steps of (i) providing a subject in need of treatment for cancer, (ii) administering to the subject a compound that activates or inhibits a gene that encodes an amino acid having a sequence comprising the sequence of SEQ ID NO:1, SEQ ID NO:2, or SEQ ID NO:3, or that activates or inhibits an expression product of the gene.

In another aspect, the invention provides a composition comprising two or more compounds identified according to any of the methods described above for identifying compounds. The invention also provides a pharmaceutical composition comprising such a composition and a pharmaceutically acceptable carrier. The invention also provides a composition comprising (i) a compound identified according to any of the methods described above for identifying compounds and (ii) a second compound, wherein the second compound is approved by the U.S. Food and Drug administration for the treatment of cancer or has shown potential efficacy against cancer in pre-clinical studies. The invention also provides a pharmaceutical composition comprising such a composition and a pharmaceutically acceptable carrier.

The present application refers to various patents, publications, books, articles, and other references. The contents of all of these items are hereby incorporated by reference in their entirety. The present application also incorporates by reference six U.S. patent applications filed by inventors on Jul. 26, 2001. These applications are entitled "REAGENTS AND METHODS FOR USE IN MANAGING BREAST CANCER", "BSTP-RAS/RERG PROTEIN AND RELATED REAGENTS AND METHODS OF USE THEREOF", "BSTP-ECG1 PROTEIN AND RELATED REAGENTS AND METHODS OF USE THEREOF", "BSTP-CAD PROTEIN AND RELATED REAGENTS AND METHODS OF USE THEREOF", "BSTP-TRANS PROTEIN AND RELATED REAGENTS AND METHODS OF USE THEREOF", "BSTP-5 PROTEINS AND RELATED REAGENTS AND METHODS OF USE THEREOF".

BRIEF DESCRIPTION OF THE DRAWING

The patent or application file contains at least one drawing executed in color. Copies of this patent or patent application publication with color drawing(s) will be provided by the Office upon request and payment of the necessary fee.

FIG. 1A presents the amino acid sequence of the polypeptide encoded by the basal marker gene known as cadherin 3 or P-cadherin (SEQ ID NO:1).

FIG. 1B presents the amino acid sequence of the polypeptide encoded by the basal marker gene known as matrix metalloproteinase 14 (SEQ ID NO:2).

FIG. 1C presents the amino acid sequence of the polypeptide encoded by the basal marker gene known as cadherin EGF LAG seven-pass G-type receptor 2 or EGF-Like Domain, Multiple 2 (SEQ ID NO:3).

FIG. 1D presents the amino acid sequences of peptides used to raise antibodies that recognize the cadherin 3, matrix metalloproteinase 14, cadherin EGF LAG seven-pass G-type receptor 2, and cytokeratin 17 proteins.

FIG. 3 shows breast tissue immunohistochemistry results obtained using various antibodies.

FIG. 3A shows tumor Stanford 2-P stained for immunoglobulin light chain.

FIG. 3B shows tumor Stanford 16 stained for the T-lymphocyte cell surface antigen CD3.

FIG. 3C shows normal mammary duct stained for the basal epithelial cell keratins 5/6.

FIG. 3D shows normal mammary duct stained for the luminal cell keratins 8/18.

FIG. 3E shows tumor New York 3 stained for keratin 5/6.

FIG. 3F shows tumor Stanford 16 stained for keratins 8/18.

FIG. 6 shows antibody staining of normal breast tissue cores in a breast tissue array.

FIG. 6A shows staining with anti-cytokeratin 5/6 monoclonal antibody.

FIG. 6B shows staining with anti-cadherin 3 polyclonal antibody.

FIG. 6C shows stainin with anti-EGF LAG seven-pass G-type receptor 2 polyclonal antibody.

FIG. 6D shows staining with anti-metallproteinase 14 polyclonal antibody.

FIG. 7 shows antibody staining of breast cancer tissue cores in a breast cancer tissue array.

FIG. 7A shows antibody staining with anti-cytokeratin 5/6 monoclonal antibody.

FIG. 7B shows antibody staining with anti-EGF LAG seven-pass G-type receptor 2 polyclonal antibody.

FIG. 7C shows antibody staining with anti-cadherin 3 polyclonal antibody.

Figures 1, 2:
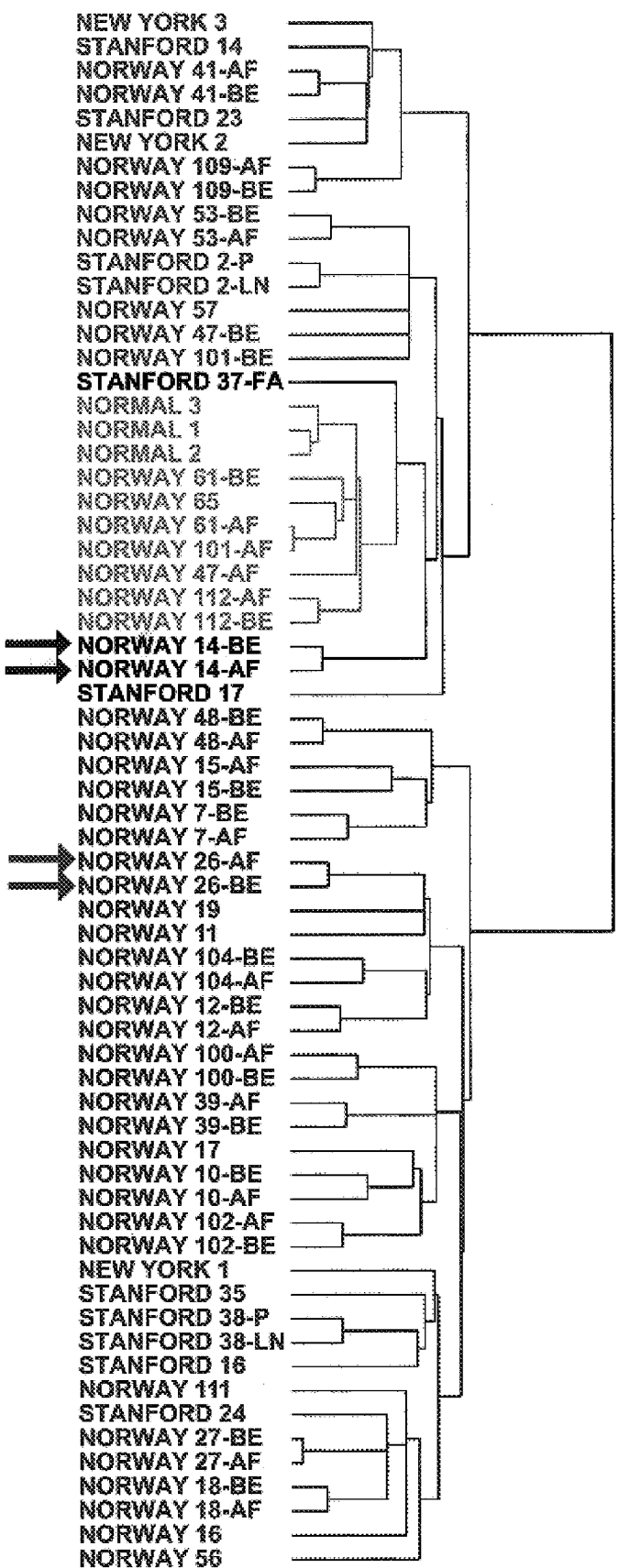
FIG. 2 shows a comparison of dendrograms representing the results of hierarchical clustering of experimental samples using the intrinsic gene set and the epithelial-enriched gene set.
Figure 2:
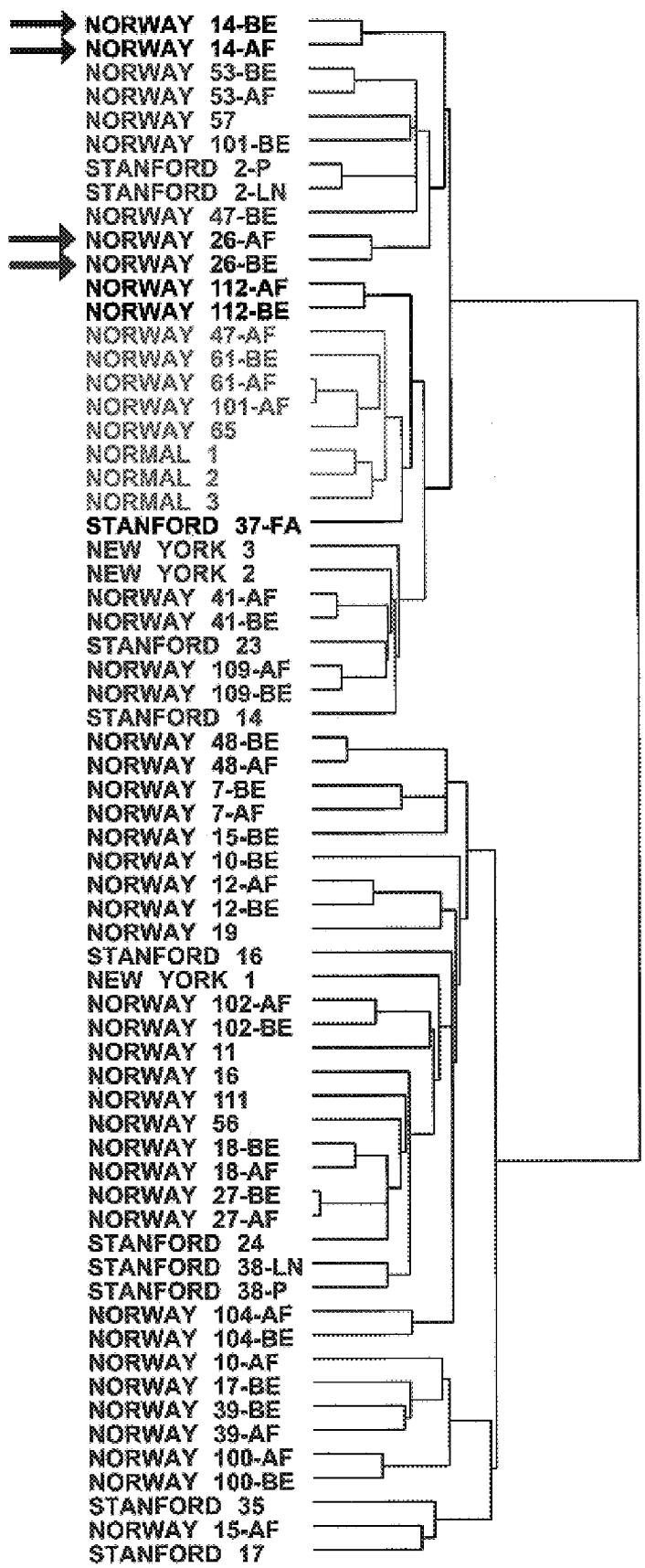

BRIEF DESCRIPTION OF APPENDICES A–G
(ON CD-ROM)

Appendix A presents the variation in expression of the 1753 genes listed in Appendix H, Table 1 in 84 experimental samples, representative of array data from which BST-RAS/RERG was identified.

Part a of Appendix A shows a dendrogram representing similarities in expression patterns between the experimental samples.

Part b of Appendix A shows a scaled down version of the complete 1753 gene cluster diagram.

Part c of Appendix A indicates the endothelial cell gene expression subset.

Part d of Appendix A indicates the stromal/fibroblast gene subset.

Part e of Appendix A indicates the basal epithelial gene subset.

Part f of Appendix A indicates the B-cell gene subset.

Part g of Appendix A indicates the adipose-enriched/normal breast gene subset.

Part h of Appendix A indicates the macrophage gene subset.

Part i of Appendix A indicates the T-cell gene subset.

Part j of Appendix A indicates the luminal epithelial cell gene subset.

Appendix B shows a close-up of the "proliferation" subset of genes taken from Part a of Appendix A.

Appendix C shows cluster analysis using the intrinsic gene set.

Part a of Appendix C shows the tumor dendrogram obtained by hierarchical clustering of the experimental samples based on similarities in expression of the intrinsic gene set.

Part b of Appendix C shows a scaled down version of the complete intrinsic gene color matrix diagram with particular gene subsets indicated by colored bars along the side.

Part c of Appendix C shows an expanded view of the luminal gene subset from part b of Appendix A.

Part d of Appendix C shows an expanded view of the ErbB2 gene subset from part b of Appendix A.

Part e of Appendix C shows an expanded view of a basal gene subset from part b of Appendix A.

Part f of Appendix C shows an expanded view of a second basal gene subset from part b of Appendix A.

Part g of Appendix C shows an expanded view of the lymphocyte/B-cell gene subset from part b of Appendix A.

Appendix D shows the complete gene cluster diagram of 84 experimental samples versus 1753 genes.

Appendix E shows the complete 496 gene cluster diagram formed when using the intrinsic gene set.

Appendix F shows the complete 374 gene cluster diagram formed when using the epithelial enriched gene set.

Appendix G presents the variation in expression of the 1495 genes in 84 experimental samples, representative of array data from which BST-RAS/RERG was identified. Note that the tumor names in this image are the alternate names provided in Appendix H, Table 4, but primarily the same samples as in the other images were used for the experiment.

BRIEF DESCRIPTION OF THE TABLES IN APPENDIX H (ON CD-ROM)

Appendix H includes 16 data tables. Some of the tables contain the numerical data corresponding to the array images in Appendices A through F. Other tables list the individual genes in the various gene subsets.

Table 1 is a master data table for the 65 microarray experiments performed on individual tumor samples, in which rows represent I.M.A.G.E. clones that identify approximately 1753 genes whose expression varied by at least a factor of 4 and columns represent individual microarray experiments. The first 50 pages of the table consist of a reference list in which a descriptive name for each clone (where such a name exists) appears in the column entitled Name, followed by the Genbank accession number for the clone. Each row in the reference list contains a number in the first column that numerically identifies the column. In the subsequent data portion of the table (pages 1–392), each row is similarly identified by a number in the first column so that the name and Genbank accession number for the clone for which data appears in that row may be determined by consulting the reference list. In the data portion of the table, the column headings in the first row identify the tumor samples. Each data cell in the table represents the measured Cy5/Cy3 fluorescence ratio at the corresponding target element on the appropriate array. Empty cells indicate insufficient or missing data. All ratio values are log transformed (base 2) to treat inductions or repressions of identical magnitude as numerically equal but with opposite sign.

Table 2 is a master data table for the 19 microarray experiments performed on cell line samples, in which rows represent I.M.A.G.E. clones that identify approximately 1753 genes whose expression varied by at least a factor of 4 and columns represent individual microarray experiments. This table contains only a data portion, in which the column headings in the first row identify the cell lines. Each row in the table is identified by a number which appears in the first column. The same reference list that forms part of Table 1 may be consulted to determine the name and Genbank accession number for the clone for which data appears in that row. Each data cell in the table represents the measured Cy5/Cy3 fluorescence ratio at the corresponding target element on the appropriate array. Empty cells indicate insufficient or missing data. All ratio values are log transformed (base 2) to treat inductions or repressions of identical magnitude as numerically equal but with opposite sign.

Table 3 presents a listing and description of the 11 cell lines used to create the common reference sample.

Table 4 presents a complete listing of the 84 experimental samples that were assayed versus the common reference sample. The table includes a list of alternate names (in the column entitled Sample ID/old name) for the same tumors. The alternate names are used to identify the tumor samples in certain contexts, and the table allows conversion between the two sets of names.

Table 5 lists the tumors used in the experiments described herein, along with clinical and pathological information about each tumor/patient.

Table 6 is a master data table for the 84 microarray experiments performed on individual tumor, tissue, and cell line samples, in which rows represent I.M.A.G.E. clones that identify the 496 genes in the intrinsic gene set, and columns represent individual microarray experiments. The first 15 pages of the table consist of a reference list in which a descriptive name for each clone (where such a name exists) appears in the column entitled Name, followed by the Genbank accession number for the clone. Each row in the reference list contains a number in the first column that numerically identifies the column. In the subsequent data portion of the table (pages 1–91), each row is similarly identified by a number in the first column so that the name and Genbank accession number for the clone for which data appears in that row may be determined by consulting the reference list. In the data portion of the table, the column headings in the first row identify the tumor samples. Each data cell in the table represents the measured Cy5/Cy3 fluorescence ratio at the corresponding target element on the appropriate array. Empty cells indicate insufficient or missing data. All ratio values are log transformed (base 2) to treat inductions or repressions of identical magnitude as numerically equal but with opposite sign.

Table 7 is a listing of the 374 clones that identify genes selected for the epithelial enriched gene set including Genbank accession numbers.

Table 8 is a listing of the clones that identify genes that comprise the luminal subset including Genbank accession numbers.

Tables 9-1 and 9-2 are listings of the two groups of clones that identify genes that comprise the basal subset including Genbank accession numbers.

Table 10 is a listing of the clones that identify genes that comprise the ErbB2 subset including Genbank accession numbers.

Table 11 is a listing of the clones that identify genes that comprise the endothelial gene subset including Genbank accession numbers.

Table 12 is a listing of the clones that identify genes that comprise the stromal/fibroblast gene subset including Genbank accession numbers.

Table 13 is a listing of the clones that identify genes that comprise the B-cell gene subset including Genbank accession numbers.

Table 14 is a listing of the clones that identify genes that comprise the adipose-enriched/normal breast gene subset including Genbank accession numbers.

Table 15 is a listing of the clones that identify genes that comprise the macrophage gene subset including Genbank accession numbers.

Table 16 is a listing of the clones that identify genes that comprise the T-cell gene subset including Genbank accession numbers.

In Table 1, the Genbank accession number for each clone appears in the column entitled "Name", following a brief descriptive name for the gene identified by the clone, where available. In some cases the descriptive name is a number corresponding to an I.M.A.G.E. clone ID number. As is well known and accepted in the art, the Genbank accession number represents a means of definitively identifying a particular clone, since Genbank accession numbers will be maintained permanently or, if changed, the change will be accomplished in such a manner as to allow unambiguous correlation between any new numbering system and the numbering system currently in use.

Note that Tables 1, 2, and 6 are provided for purposes of presenting the clone identifications and the data that was used to perform hierarchical clustering analysis, and that the format of the tables may not correspond exactly with the format required by software developed for the analysis of the data. Appropriate format will, in general, depend upon the particular computer program. See, for example, the Web site genome-www.stanford.edu~sherlock/tutorial.html for discussion of the appropriate format for one particular analysis program.

In Tables 7–16, each entry identifies a clone. The first portion of each entry is a brief descriptive name for the gene identified by the clone. The Genbank accession number for the clone appears on the last line of the entry for that clone.

DETAILED DESCRIPTION OF CERTAIN EMBODIMENTS

DEFINITIONS

To facilitate understanding of the invention, the following definitions are provided. It is to be understood that, in general, terms not otherwise defined are to be given their meaning or meanings as generally accepted in the art.

Agonist: As used herein, the term "agonist" refers to a molecule that increases or prolongs the duration of the effect of a polypeptide or a nucleic acid. Agonists may include proteins, nucleic acids, carbohydrates, lipids, small molecules, ions, or any other molecules that modulate the effect of the polypeptide or nucleic acid. An agonist may be a direct agonist, in which case it is a molecule that exerts its effect by binding to the polypeptide or nucleic acid, or an indirect agonist, in which case it exerts its effect via a mechanism other than binding to the polypeptide or nucleic acid (e.g., by altering expression or stability of the polypeptide or nucleic acid, by altering the expression or activity of a target of the polypeptide or nucleic acid, by interacting with an intermediate in a pathway involving the polypeptide or nucleic acid, etc.)

Antagonist: As used herein, the term "antagonist" refers to a molecule that decreases or reduces the duration of the effect of a polypeptide or a nucleic acid. Antagonists may include proteins, nucleic acids, carbohydrates, or any other molecules that modulate the effect of the polypeptide or nucleic acid. An antagonist may be a direct antagonist, in which case it is a molecule that exerts its effect by binding to the polypeptide or nucleic acid, or an indirect antagonist, in which case it exerts its effect via a mechanism other than binding to the polypeptide or nucleic acid (e.g., by altering expression or stability of the polypeptide or nucleic acid, by altering the expression or activity of a target of the polypeptide or nucleic acid, by interacting with an intermediate in a pathway involving the polypeptide or nucleic acid, etc.)

Basal cell: The term "basal cell" is a general term applied to any stratified or pseudostratified epithelium. It refers to cells which are juxtaposed to the basement membrane and under one or more additional epithelial layers. Mammary tissue can have both a two cell layer epithelium (basal and luminal cells) or in the duct system, a single layered epithelium. In the two cell layer, the cells adjacent to the basement membrane are termed "basal cells" and express basal cell markers (e.g., cytokeratin 17 and cytokeratin 5/6). In pseudostratified epitheum "non-basal" cells can also contact the basement membrane but since normal breast epithelium is not, in general, pseudostratified, breast basal cells are cells located adjacent to basement membrane and under one or more additional layers of epithelial cells. As used herein, the term "basal cell" is distinct from "myoepithelial cell" in that myoepithelial cell refers to cells that have the contractual apparatus for milk excretion by the ducts (i.e., they express contractile proteins).

Breast basal cell marker: A gene whose expression is characteristic of basal cells of normal breast lactation ducts, or an expression product of such a gene (e.g., an mRNA or polypeptide). The marker may be used to distinguish basal cells from other cells in the breast, e.g., luminal cells. In the case of a marker that is a polypeptide, antibodies to the polypeptide stain cells in the basal layer of normal breast lactation ducts when used to perform immunohistochemistry on breast tissue samples. Since the present invention is concerned primarily with breast cancer, the term "basal cell marker" is used interchangeably with "breast basal cell marker" herein unless otherwise indicated. Examples of basal cell markers include the cytokeratin 5 and cytokeratin 17 genes, mRNAs, and proteins, in addition to the newly identified basal cell markers described herein.

Breast basal tumor marker: A gene whose expression is characteristic of basal cells in the normal breast lactation duct and which is also expressed in a subset of breast tumors, or an expression product of such a gene. These genes include cytokeratin 5 and cytokeratin 17, which are known from the prior art to distinguish breast basal cells from other breast tissue cells, and the genes identified herein. Antibodies to the proteins encoded by these genes identify basal breast cells when used to perform immunohistochemical staining of normal breast tissue, i.e., they stain cells in the basal epithelial layer. The term "basal tumor marker" is used interchangeably with "breast basal tumor marker" herein unless otherwise indicated.

Breast basal tumor subclass: The breast basal tumor subclass, as used herein, refers to breast tumors that display characteristics of basal cells of normal breast lactation ducts. Such characteristics include expression of genes whose expression has been shown to discriminate between normal basal cells of breast lactation ducts and other cells in the breast, including luminal cells of breast lactation ducts. These genes include cytokeratin 5 and cytokeratin 17, which are known from the prior art to distinguish breast basal cells from other breast tissue cells, and the genes identified herein. Antibodies to the proteins encoded by these genes identify basal breast cells when used to perform immunohistochemical staining of normal breast tissue, i.e., they stain cells in the basal epithelial layer. The term "breast basal tumor subclass" is used interchangeably with "basal tumor subclass" herein unless otherwise indicated.

Diagnostic information: As used herein, diagnostic information or information for use in diagnosis is any information that is useful in determining whether a patient has a disease or condition and/or in classifying the disease or condition into a phenotypic category or any category having significance with regards to the prognosis of or likely response to treatment (either treatment in general or any particular treatment) of the disease or condition. Similarly, diagnosis refers to providing any type of diagnostic information, including, but not limited to, whether a subject is likely to have a condition (such as a tumor), information related to the nature or classification of a tumor, information related to prognosis and/or information useful in selecting an appropriate treatment. Selection of treatment may include the choice of a particular chemotherapeutic agent or other treatment modality such as surgery, radiation, etc., a choice about whether to withhold or deliver therapy, etc.

Differential expression: A gene exhibits differential expression at the RNA level if its RNA transcript varies in abundance between different samples in a sample set. A gene exhibits differential expression at the protein level, if a polypeptide encoded by the gene varies in abundance between different samples in a sample set. In the context of a microarray experiment, differential expression generally refers to differential expression at the RNA level.

Gene: For the purposes of the present invention, the term "gene" has its meaning as understood in the art. However, it will be appreciated by those of ordinary skill in the art that the term "gene" has a variety of meanings in the art, some of which include gene regulatory sequences (e.g., promoters, enhancers, etc.) and/or intron sequences, and others of which are limited to coding sequences. It will further be appreciated that definitions of "gene" include references to nucleic acids that do not encode proteins but rather encode functional RNA molecules such as tRNAs. For the purpose of clarity we note that, as used in the present application, the term "gene" generally refers to a portion of a nucleic acid that encodes a protein; the term may optionally encompass regulatory sequences. This definition is not intended to exclude application of the term "gene" to non-protein coding expression units but rather to clarify that, in most cases, the term as used in this document refers to a protein coding nucleic acid.

Gene product or expression product: A gene product or expression product is, in general, an RNA transcribed from the gene or a polypeptide encoded by an RNA transcribed from the gene.

Marker: A marker, as used herein, refers to a gene whose expression is characteristic of a particular cell type. The term may also refer to a product of gene expression, e.g., an RNA transcribed from the gene or a translation product of such an RNA, the production of which is characteristic of a particular cell type. The cell type may be defined based on any phenotypic criterion. For example, a normal breast basal cell is defined based on its position within an epithelial layer. In some cases expression of a marker gene may be the sole criterion used to define the cell type. The statistical significance of the presence or absence of a marker gene expression product may vary depending upon the particular marker. In some cases the detection of a marker is highly specific in that it reflects a high probability that the cell is of a particular type. This specificity may come at the cost of sensitivity, i.e., a negative result may occur even if the cell is a cell that would be expected to express the marker. Conversely, markers with a high degree of sensitivity may be less specific than those with lower sensitivity. Thus it will be appreciated that a useful marker need not distinguish cells of a particular type with 100% accuracy. Furthermore, it will be appreciated that the use of multiple markers may improve the specificity and/or sensitivity with which a cell can be identified as being of a particular cell type. The concept of a marker may be applied not only to individual cells, but also to tumors or to other disease states. In the case of tumors, a marker for a particular tumor class is a gene whose expression is characteristic of a particular tumor type, i.e., a gene whose expression is characteristic of some or all of the cells in the tumor. The term may also refer to a product of gene expression, e.g., an RNA transcribed from the gene or a translation product of such an RNA, the production of which is characteristic of a particular tumor type, i.e., of some or all of the cells in the tumor.

Prognostic information and predictive information: As used herein the terms prognostic information and predictive information are used interchangeably to refer to any information that may be used to foretell any aspect of the course of a disease or condition either in the absence or presence of treatment. Such information may include, but is not limited to, the average life expectancy of a patient, the likelihood that a patient will survive for a given amount of time (e.g., 6 months, 1 year, 5 years, etc.), the likelihood that a patient will be cured of a disease, the likelihood that a patient's disease will respond to a particular therapy (wherein response may be defined in any of a variety of ways). Prognostic and predictive information are included within the broad category of diagnostic information.

Response: As used herein a response to treatment may refer to any beneficial alteration in a subject's condition that occurs as a result of treatment. Such alteration may include stabilization of the condition (e.g., prevention of deterioration that would have taken place in the absence of the treatment), amelioration of symptoms of the condition, improvement in the prospects for cure of the condition, etc. One may refer to a subject's response or to a tumor's response. In general these concepts are used interchangeably herein. Tumor or subject response may be measured according to a wide variety of criteria, including clinical criteria and objective criteria. Techniques for assessing response include, but are not limited to, clinical examination, chest X-ray, CT scan, MRI, ultrasound, endoscopy, laparoscopy, presence or level of tumor markers in a sample obtained from a subject, cytology, histology. Many of these techniques attempt to determine the size of a tumor or otherwise determine the total tumor burden. Methods and guidelines for assessing response to treatment are discussed in Therasse P., et al., "New guidelines to evaluate the response to treatment in solid tumors", European Organization for Research and Treatment of Cancer, National Cancer Institute of the United States, National Cancer Institute of Canada. J Natl Cancer Inst, Feb 2;92(3):205–16, 2000. The exact response criterion can be selected in any appropriate manner, provided that when comparing groups of tumors and/or patients, the groups to be compared are assessed based on the same or comparable criteria for determining response rate. One of ordinary skill in the art will be able to select appropriate criteria.

Sample: As used herein, a sample obtained from a subject may include, but is not limited to, any or all of the following: a cell or cells, a portion of tissue, blood, serum, ascites, urine, saliva, and other body fluids, secretions, or excretions. The term "sample" also includes any material derived by processing such a sample. Derived samples may include nucleic acids or proteins extracted from the sample or obtained by subjecting the sample to techniques such as amplification or reverse transcription of mRNA, etc.

Specific binding: As used herein, the term refers to an interaction between a target polypeptide (or, more generally, a target molecule) and a binding molecule such as an antibody, agonist, or antagonist. The interaction is typically dependent upon the presence of a particular structural feature of the target polypeptide such as an antigenic determinant or epitope recognized by the binding molecule. For example, if an antibody is specific for epitope A, the presence of a polypeptide containing epitope A or the presence of free unlabeled A in a reaction containing both free labeled A and the antibody thereto, will reduce the amount of labeled A that binds to the antibody. It is to be understood that specificity need not be absolute. For example, it is well known in the art that numerous antibodies cross-react with other epitopes in addition to those present in the target molecule. Such cross-reactivity may be acceptable depending upon the application for which the antibody is to be used. One of ordinary skill in the art will be able to select antibodies having a sufficient degree of specificity to perform appropriately in any given application (e.g., for detection of a target molecule, for therapeutic purposes, etc). It is also to be understood that specificity may be evaluated in the context of additional factors such as the affinity of the binding molecule for the target polypeptide versus the affinity of the binding molecule for other targets, e.g., competitors. If a binding molecule exhibits a high affinity for a target molecule that it is desired to detect and low affinity for nontarget molecules, the antibody will likely be an acceptable reagent for immunodiagnostic purposes. Once the specificity of a binding molecule is established in one or more contexts, it may be employed in other, preferably similar, contexts without necessarily re-evaluating its specificity.

Treating a tumor: As used herein, treating a tumor is taken to mean treating a subject who has the tumor.

Tumor sample: The term "tumor sample" as used herein is taken broadly to include cell or tissue samples removed from a tumor, cells (or their progeny) derived from a tumor that may be located elsewhere in the body (e.g., cells in the bloodstream or at a site of metastasis), or any material derived by processing such a sample. Derived tumor samples may include nucleic acids or proteins extracted from the sample or obtained by subjecting the sample to techniques such as amplification or reverse transcription of mRNA, etc.

Tumor subclass: A tumor subclass, also referred to herein as a tumor subset or tumor class, is the group of tumors that display one or more phenotypic or genotypic characteristics that distinguish members of the group from other tumors.

I. Overview and Description of the Basal Marker Genes, Polynucleotides, and Polypeptides The present invention provides new reagents and methods for the management (e.g., detection, classification, provision of diagnostic and prognostic information, treatment, etc.) of breast cancer. Significant progress has been made in understanding risk factors, including genetic factors, that may contribute to breast cancer (See, for example, Vogelstein, B. and Kinzler, eds., "Breast Cancer", by Couch, F. and Weber, B. in *The Genetic Basis of Human Cancer*, McGraw Hill, 1998), but the relevance of these factors to clinical outcome remains unclear. The most powerful prognosticators are clinical features such as lymph node status, tumor size, and tumor grade. In addition, the expression level and antibody staining pattern of several proteins are predictive of outcome and of the likelihood of response to therapy. However, the clinical outcome of individual patients remains uncertain. In addition, the ability to predict which patients are likely to benefit from a particular type of therapy (e.g., a certain drug or class of drug) remains elusive.

The invention encompasses the realization that high throughput analysis techniques, e.g., those involving the use of cDNA microarrays, can be used to provide new insights into the biology of breast cancer. By analyzing the transcriptional profiles of a large number of breast tumor samples and by undertaking comparisons, e.g., between tumors associated with varying prognoses, between primary tumors and metastases, between tumors before and after treatment, and between tumors with differing responses to therapy, the present invention provides new tools and methods for classifying tumors and defines new classes of tumors based on these methods. The invention identifies genes and gene subsets that are useful in classifying breast tumors. In addition, the methods described herein identify genes that are likely to play a role in breast cancer development, progression, and/or response to therapy. Classification based on expression of particular genes may be used to predict clinical course or to predict sensitivity to chemotherapeutic agents. Ultimately such classification may be used to guide selection of appropriate therapy. As described herein, detection of mRNA and protein corresponding to differentially expressed genes provides new methods of use in cancer prognosis, diagnosis, and treatment selection. In addition, differentially expressed genes and their encoded proteins provide targets for the identification of new therapies for breast cancer.

As described in further detail below, the invention employs methods for clustering genes into groups by determining their expression patterns across a set of samples obtained from breast tumors and from normal breast tissue. The invention also clusters the breast tumor and normal breast tissue samples into groups based on similarities in their expression of a set of genes. This two-dimensional clustering approach permits the association of particular classes of tumors with particular subsets of genes that, for example, show relatively high levels of expression in the tumors. Correlation with clinical information indicates that the tumor classes have clinical significance in terms of prognosis or response to chemotherapy.

Genes that are relatively overexpressed in tumors may be particularly appropriate targets for the development of new therapeutic agents. Any gene (or combination of genes) that is overexpressed in some tumors forms a basis by which tumors can be divided into different groups. As demonstrated herein, when particular sets of genes are used such groups have clinical significance in that, for example, they display differences in prognosis. However, regardless of whether the resulting division has significance in terms of known clinical parameters, therapeutic agents directed towards such genes or towards their encoded proteins would be expected to be specific for the tumors that overexpress the genes. Thus the invention offers an opportunity for the development and selection of therapeutic agents based on specific properties of a tumor. In other words, any gene that is overexpressed in a subset of tumors can be used to define that subclass and is a potential target for the development of a therapeutic agent that is specific for that tumor subclass.

In particular, tumors that display characteristics of basal cells of the normal breast lactation gland (also referred to herein as breast basal cells) form a distinct subclass (referred to herein as the basal subclass). It is known in the art that two distinct types of epithelial cells are found in the adult human mammary gland: basal cells and luminal epithelial cells. Expression of cytokeratin 5 and/or cytokeratin 17 is a characteristic of basal cells of the normal mammary lactation gland, while cytokeratins 8 and 18 are expressed in luminal cells. Cytokeratins are a family of intermediate filament proteins, members of which are found in most or all epithelial cell types (Moll, R., et al., "The catalog of human cytokeratins: patterns of expression in normal epithelia, tumors, and cultured cells", *Cell,* 31(1), 11–24, 1982. Intermediate-sized filaments are morphologically similar but biochemically and immunologically distinguishable cytoplasmic proteins of which five major filament types have been identified (cytokeratin, vimentin, desmin, neurofilament protein, glia filament protein), and antibodies to these proteins have been used for distinguishing different cell types and tumors derived therefrom. Epithelial and carcinoma cells are characterized by the presence of cytokeratin filaments that can be identified by antibodies. These antibodies can be used to distinguish between different cell and tumor types (Dobus, E., et al., "Immunohistochemical distinction of human carcinomas by cytokeratin typing with monoclonal antibodies", *Am J. Pathol.,* 114(1): 121–30, 1984). In particular, antibodies against cytokeratins 5/6, 17, 8, and 18 may be used to distinguish between breast basal and luminal cell types in normal breast and in tumors (See, e.g., Purkis, P., et al., "Antibody markers of basal cells in complex epithelia", *J. Clin. Pathol.,* 48:26–32, 1990; Taylor,-Papadimitriou and Lane, E., "Keratin expression in the mammary gland" in Neville, M and Daniel C, eds. *The Mammary Gland: Development, Regulation, and Function.* New York: Plenum, pp. 181–215, 1987; Dairkee, S., et al., "Immunolocalization of a human basal epithelium-specific keratin in benign and malignant breast disease. *Breast Cancer Res. Treat.,* 10:11–20, 1987.)

Several previous studies suggested that expression of basal cell keratins is associated with a poor clinical outcome (Dairkee, S. H., et al., "Monoclonal antibody that predicts early recurrence of breast cancer", *Lancet,* 1:514, 1987; Malzahn, K., etal., "Biological and prognostic significance of stratified epithelial cytokeratins in infiltrating ductal breast carcinomas", *Virchows Archiv,* 433:119–29, 1998). Inventors have confirmed, in a large-scale study, that patients with breast tumors whose cells display characteristics of breast basal cells, e.g., expression of cytokeratin 5 and/or cytokeratin 17, have a poor clinical outcome relative to patients with breast tumors that do not express these markers. However, antibodies to these cytokeratins have been found (by the inventors and by other investigators) to give spotty, focal staining patterns when used to perform inimunohistochemistiy on breast tumor samples. Thus the utility of cytokeratins 5 and 17 as markers and the utility of antibodies that bind to cytokeratin 5 or 17 for determining whether a tumor is a member of the basal subclass has been limited. The inventors have therefore identified genes whose mRNA expression profiles across a large set of tumor samples correlate with, i.e., are similar to, the expression profiles of the known basal cell markers cytokeratins 5 and 17. These genes include the basal marker genes of the present invention, i.e., genes that encode cadherin3 or P-cadherin (SEQ ID NO:1; GenBank protein accession number NP_001784; GenBank cDNA accession number NM_001793), matrix metalloproteinase 14 (SEQ ID NO:2; GenBank protein accession number NP_004986; GenBank cDNA accession number NM_004995); and cadherin EGF LAG seven-pass G-type receptor 2 or EGF-Like Domain, Multiple 2 (SEQ ID NO:3; GenBank protein accession number NP_001399; GenBank cDNA accession number NM_001408). A portion of the cadherin3 gene was present as I.M.A.G.E. clone 777301 on the cDNA microarray described below. This clone is entry #421 in Appendix H, Table 1. A portion of the matrix metalloproteinase 14 gene was present as I.M.A.G.E. clone 270505 on the cDNA microarray described below. This clone is entry #424 in Appendix H, Table 1. A portion of the cadherin EGF LAG seven-pass G-type receptor 2 gene was present as I.M.A.G.E. clone 175103 on the cDNA microarray described below. This clone is entry #1443 in Appendix H, Table 1. Information about these genes may be found at NCBI's LocusLink (www.ncbi.nlm.nih.gov/LocusLink), among other sources. As described in Examples 10 and 13, the inventors have generated antibodies to the proteins expressed by these genes and shown that the antibodies stain basal cells of normal mammary lactation glands. Thus detection of one or more expression products of these genes may be used to identify tumors that fall within the basal tumor subclass.

As is well known in the art, breast carcinomas lose the typical histology and architecture of normal breast glands. Generally, carcinoma cells overgrow the normal cells and lose their ability to differentiate into glandular like structures. The degree of loss of differentiation in general is related to the aggressiveness of the tumor. For example, "in situ" carcinoma by definition retains the basement membrane intact, whereas as it progresses to "invasive", the tumor shows breakout of basement membranes. Thus one would not expect to see, within breast carcinomas, staining of a discrete layer of basal cells as seen in normal breast tissue. For a discussion of the physiology and histology of normal breast and breast carcinoma, see Ronnov-Jessen, L., Petersen, O. W. & Bissell, M. J. Cellular changes involved in conversion of normal to malignant breast: importance of the stromal reaction. Physiol Rev 76, 69–125 (1996).

The basal marker genes provided herein are expressed in the best model of basal cells (HMECs, Human Mammary Epithelial Cells) and based on antibody staining, in normal breast basal cells. Therefore describing them as basal markers is appropriate. However, in addition to their specific staining properties, a major characteristic that makes these genes and their expression products useful is their variation in expression across cohorts of breast carcinoma patients, which portends their utility in stratification of breast carcinoma patients. While not wanting to be limited by the implications of having chosen a particular descriptor (i.e.

"basal") inventors refer to the set of genes, proteins, and antibody reactivity patterns as "basal" as it serves as a reminder of their utility in recognizing breast tumor cells that have characteristics reminiscent of normal breast basal cells. Breast tumors containing such cells are likewise referred to as "basal" without intending any limitations thereby.

Two of the basal marker genes, cadherin3 and cadherin EGF LAG seven-pass G-type receptor 2 encode members of the cadherin superfamily. The cadherin EGF LAG seven-pass G-type receptor 2 or EGF-Like Domain, Multiple 2 protein is a member of the flamingo subfamily, part of the cadherin superfamily. The cadherins are a large family of proteins with critical roles in the regulation of cell-cell adhesion. Generally expressed in development- or tissue-specific manners, these factors have been shown to have important roles in development, cellular proliferation, and differentiation. The cadherin superfamily include classic cadherins, desmogleins, desmocollins, protocadherins, CNRs, Fats, and seven-pass transmembrane cadherins (for review see Nollet et al. 2000). Typically transmembrane proteins, the cadherins are characterized by the unique cadherin, or EC, domain. These cadherin domains, which are involved in $Ca^{++}$ binding (Takeichi 1990), are repeated in the extracellular region of all of the family members. The amino acid sequences of other regions shows significant divergence among members, suggesting functional diversity amongst the various cadherin proteins. However, amid the members of each subfamily, the cytoplasmic domains are conserved. In the classic cadherins, which are components of adherens junctions and desmoplakin plaques, this region interacts with catenin $p120^{ctn}$, and plakoglobin or β-catenin. The latter binds to α-catenin, and this molecular complex further associates with α-actinin, F-actin and other cytoskeletal proteins. Consistent with their roles in regulating cell-cell adhesion events, altered expression of cadherin genes has been associated with human cancer. Alteration of cadherin function may lead to subsequent metastasis by disaggregation of tumor cells, and one proposed role of many cadherins studied to date is as tumor- and invasion-suppressors. Further discussion of some of the many members of the cadherin superfamily and their possible role in cancer is found in references 53–61.

The flamingo subfamily consists of nonclassic-type cadherins; a subpopulation that does not interact with catenins. The flamingo cadherins are located at the plasma membrane and have nine cadherin domains, seven epidermal growth factor-like repeats and two laminin A G-type repeats in their ectodomain. They also have seven transmembrane domains, a characteristic unique to this subfamily. While not wishing to be bound by any theory, it is postulated that these proteins are receptors involved in contact-mediated communication, with cadherin domains acting as homophilic binding regions and the EGF-like domains involved in cell adhesion and receptor-ligand interactions. The cadherin EGF LAG seven-pass G-type receptor 2 gene (also known as CELSR2) has not been as extensively studied as the classic cadherins, but is implicated in cell signaling. The *Drosophila* homolog of this gene has been studied in more detail, and is clearly important in regulating different cellular events (Usui T, Shima Y, Shimada Y, Hirano S, Burgess R W, Schwarz T L, Takeichi M, Uemura T, "Flamingo, a seven-pass transmembrane cadherin, regulates planar cell polarity under the control of Frizzled", *Cell* 1999 98:585–95. While not wishing to be bound by any theory, it is postulated that this protein is a receptor involved in contact-mediated communication, with the cadherin domains acting as homophilic binding regions and the EGF-like domains involved in cell adhesion and receptor-ligand interactions.

Proteins of the matrix metalloproteinase (MMP) family are involved in the breakdown of extracellular matrix in normal physiological processes, such as embryonic development, reproduction, and tissue remodeling, as well as in disease processes, such as arthritis and metastasis. Most MMP's are secreted as inactive proproteins which are activated when cleaved by extracellular proteinases. However, matrix metalloproteinase 14 protein is a member of the membrane-type MMP (MT-MMP) subfamily; each member of this subfamily contains a potential transmembrane domain suggesting that these proteins are expressed at the cell surface rather than secreted. This protein activates MMP2 protein, and this activity may be involved in tumor invasion.

Cadherin3 is predicted to be membrane-bound, with an extracellular portion. As indicated by the presence of seven putative transmembrane domains, cadherin EGF LAG seven-pass G-type receptor 2 is also likely to be a membrane bound protein. The presence of a predicted transmembrane domain indicates that matrix metalloproteinase 14 is also membrane bound. The likelihood that the proteins encoded by the basal marker genes are membrane bound makes them attractive candidate for the application of serological assays for diagnostic purposes. In addition, the likelihood that cadherin3, cadherin EGF LAG seven-pass G-type receptor 2, and matrix metalloproteinase 14 are membrane bound makes them attractive candidates for antibody therapeutics.

The invention provides antibodies that specifically bind to the polypeptide expression products of the basal marker genes, i.e., the polypeptides of SEQ ID NO:1, 2, and 3. The antibodies stain basal cells of the normal mammary lactation gland. In certain embodiments of the invention the antibodies distinguish basal cells from luminal cells in normal mammary lactation glands.

The antibodies are potentially useful as therapeutic reagents for cancer, particularly breast cancer, either by themselves or when conjugated to or delivered with another molecule such as a toxic compound. The invention further provides pharmaceutical compositions comprising agonists or antagonists of the polynucleotides and their encoded polypeptides, and methods of use thereof for the treatment of cancer. The invention includes a variety of methods for providing information of use in the prognosis, classification, diagnosis, etc. of cancer, particularly breast cancer.

In order that the manner in which the basal cell marker genes of the present invention were identified may be better understood, a description of cDNA microarray technology is provided below. Following this description the specific experimental approach employed herein is described. Certain aspects of the invention are then described in further detail.

II. cDNA Microarray Technology cDNA microarrays consist of multiple (usually thousands) of different cDNAs spotted (usually using a robotic spotting device) onto known locations on a solid support, such as a glass microscope slide. The cDNAs are typically obtained by PCR amplification of plasmid library inserts using primers complementary to the vector backbone portion of the plasmid or to the gene itself for genes where sequence is known. PCR products suitable for production of microarrays are typically between 0.5 and 2.5 kB in length. Full length cDNAs, expressed sequence tags (ESTs), or randomly chosen cDNAs from any library of interest can be chosen. ESTs are partially sequenced cDNAs as described, for example, in L. Hillier, et al., Generation and analysis of 280,000 human expressed sequence tags, *Genome Research*, 6, 807–828, 1996. The afore-mentioned article is herein incorporated by reference, as are the entire teachings of all other patents and journal articles mentioned herein, for all purposes and not just those related to the particular context in which they are mentioned. Although some ESTs correspond to known genes, frequently very little or no information regarding any particular EST is available except for a small amount of 3' and/or 5' sequence and, possibly, the tissue of origin of the mRNA from which the EST was derived. As will be appreciated by one of ordinary skill in the art, in general the cDNAs contain sufficient sequence information to uniquely identify a gene within the human genome. Furthermore, in general the cDNAs are of sufficient length to hybridize, preferably specifically and yet more preferably uniquely, to cDNA obtained from mRNA derived from a single gene under the hybridization conditions of the experiment.

In a typical microarray experiment, a microarray is hybridized with differentially labeled RNA or DNA populations derived from two different samples. Most commonly RNA (either total RNA or poly $A^+$RNA) is isolated from cells or tissues of interest and is reverse transcribed to yield cDNA. Labeling is usually performed during reverse transcription by incorporating a labeled nucleotide in the reaction mixture. Although various labels can be used, most commonly the nucleotide is conjugated with the fluorescent dyes Cy3 or Cy5. For example, Cy5-dUTP and Cy3-dUTP can be used. cDNA derived from one sample (representing, for example, a particular cell type, tissue type or growth condition) is labeled with one fluor while cDNA derived from a second sample (representing, for example, a different cell type, tissue type, or growth condition) is labeled with the second fluor. Similar amounts of labeled material from the two samples are cohybridized to the microarray. In the case of a microarray experiment in which the samples are labeled with Cy5 (which fluoresces red) and Cy3 (which fluoresces green), the primary data (obtained by scanning the microarray using a detector capable of quantitatively detecting fluorescence intensity) are ratios of fluorescence intensity (red/green, R/G). These ratios represent the relative concentrations of cDNA molecules that hybridized to the cDNAs represented on the microarray and thus reflect the relative expression levels of the mRNA corresponding to each cDNA/gene represented on the microarray.

Each microarray experiment can provide tens of thousands of data points, each representing the relative expression of a particular gene in the two samples. Appropriate organization and analysis of the data is of key importance. Various computer programs that incorporate standard statistical tools have been developed to facilitate data analysis. One basis for organizing gene expression data is to group genes with similar expression patterns together into clusters. A method for performing hierarchical cluster analysis and display of data derived from microarray experiments is described in Eisen, M., Spellman, P., Brown, P., and Botstein, D., Cluster analysis and display of genome-wide expression patterns, *Proc. Natl. Acad. Sci. USA,* 95: 14863–14868, 1998. As described therein, clustering can be combined with a graphical representation of the primary data in which each data point is represented with a color that quantitatively and qualitatively represents that data point. By converting the data from a large table of numbers into a visual format, this process facilitates an intuitive analysis of the data. Additional information and details regarding the mathematical tools and/or the clustering approach itself may be found, for example, in Sokal, R. R. & Sneath, P.H.A. Principles of numerical taxonomy, xvi, 359, W. H. Freeman, San Francisco,1963; Hartigan, J. A. Clustering algorithms, xiii, 351, Wiley, New York, 1975; Paull, K. D. et al. Display and analysis of patterns of differential activity of drugs against human tumor cell lines: development of mean graph and COMPARE algorithm. *J Natl Cancer Inst* 81, 1088–92, 1989; Weinstein, J. N. et al. Neural computing in cancer drug development: predicting mechanism of action. *Science* 258, 447–51, 1992; van Osdol, W. W., Myers, T. G., Paull, K. D., Kohn, K. W. & Weinstein, J. N. Use of the Kohonen self-organizing map to study the mechanisms of action of chemotherapeutic agents. *J Natl Cancer Inst* 86, 1853–9, 1994; and Weinstein, J. N. et al. An information-intensive approach to the molecular pharmacology of cancer. *Science,* 275, 343–9, 1997.

Further details of the experimental methods used in the present invention are found in the Examples. Additional information describing methods for fabricating and using microarrays is found in U.S. Pat. No. 5,807,522, which is herein incorporated by reference. Instructions for constructing microarray hardware (e.g., arrayers and scanners) using commercially available parts can be found at cmgm.stanford.edu/pbrown/ and in Cheung, V., Morley, M., Aguilar, F., Massimi, A., Kucherlapati, R., and Childs, G., Making and reading microarrays, *Nature Genetics Supplement,* 21:15–19, 1999, which are herein incorporated by reference. Additional discussions of microarray technology and protocols for preparing samples and performing microarray experiments are found in, for example, DNA arrays for analysis of gene expression, *Methods Enzymol,* 303:179–205, 1999; Fluorescence-based expression monitoring using microarrays, *Methods Enzymol,* 306: 3–18, 1999; and M. Schena (ed.), DNA Microarrays: A Practical Approach, Oxford University Press, Oxford, UK, 1999. Descriptions of how to use an arrayer and the associated software are found at cmgm.stanford.edu/pbrown/mguide/arrayerHTML/ArrayerDocs.html, which is herein incorporated by reference.

III. Experimental Approach of the Invention

The present invention encompasses the realization that genes that are differentially expressed are of use in classifying tumors. Differentially expressed genes are likely to be responsible for the different phenotypic characteristics of tumors. The present invention identifies such genes. In general, a differentially expressed gene is a gene whose transcript abundance varies between different samples, e.g., between different tumor samples, between normal versus tumor samples, etc. In the case of the experiment described herein, the transcript level of a differentially expressed gene varies by at least 4-fold from its average abundance in a given sample set in at least 3 of the samples. However, genes that display smaller variations in expression are also within the scope of the invention. In general, the amount by which the expression varies and the number of samples in which the expression varies by that amount will depend upon the number of samples and the particular characteristics of the samples. One skilled in the art will be able to determine, based on knowledge of the samples, what constitutes a significant degree of differential expression.

While analysis of multiple genes is of use in developing a robust classification of tumors, each of the differentially expressed genes and their encoded proteins is a target for the development of diagnostic and therapeutic agents. Investigation of variation in individual genes in breast tumors reveals that molecular variation can be related to important features of clinical variation. For example, expression of the estrogen receptor alpha gene (ESR1), the Erb-B2/HER2/neu oncogene, and the mutational status at the TP53, BRCA1 and BRCA2 loci have shown that molecular variation can be related to important features of clinical variation. (Discussed, for example, in Osborne, C. K., et al., The value of estrogen and progesterone receptors in the treatment of breast cancer, *Cancer* 46, 2884–2888, 1980; Ingvarsson, S., Molecular genetics of breast cancer progression, *Seminars in Cancer Biology*, 9, 277–288, 1999; Breast Cancer Linkage Consortium, Pathology of familial breast cancer: differences between breast cancers in carriers of BRCA1 and BRCA2 mutations and sporadic cases, *Lancet*, 349, 1505–1510, 1997; Anderson, T. I., et al., Prognostic significance of TP53 alterations in breast carcinoma. *Br J Cancer*, 68, 540–548, 1993 and references cited in these articles). In particular, approximately 60% to 70% of breast tumors express the estrogen receptor, and this expression has been shown to be a favorable prognostic factor (reviewed in Allred, D. C., et al. Prognostic and Predictive Factors in Breast Cancer by Immunohistochemical Analysis, *Modern Pathology*, 11(2), 155–168, 1998).

As described in more detail in Examples 1, 2, and 4, cDNA microarrays each representing the same set of approximately 8100 different human genes were produced. The human cDNA clones used to produce the microarrays contained approximately 4000 named genes, 2000 genes with homology to named genes in other species, and approximately 2000 ESTs of unknown function. An mRNA sample was obtained from each of a set of 84 tissue samples or cell lines. The expression levels of the approximately 8100 genes were measured in each mRNA sample by hybridization to an individual microarray, yielding an expression profile for each gene across the experimental samples. Although more details will be found in the Examples, an overview of the experimental procedure is presented here so that the invention may be better understood.

Variation in patterns of gene expression were characterized in 62 breast tumor samples from 40 different patients, 3 normal breast tissue samples, and 19 samples from 17 cultured human cell lines (one of which was sampled 3 times under different conditions). Twenty of the tumors had been sampled twice, before and after a 16 week course of doxorubicin chemotherapy, and two tumors were paired with a lymph node metastasis from the same patient. The other 18 tumor samples were single samples from individual tumors. A detailed listing of the tumor samples and various characteristics including clinical estrogen receptor and Erb-B2 status as assessed using antibody staining, estrogen receptor and Erb-B2 status as assessed by microarray result, tumor grade, differentiation, survival status and time, age at diagnosis, doxorubicin response, and p53 status is presented in Table 5. A listing of the cell lines including description and ATCC (American Tissue Culture Collection) number or reference is presented in Table 3. The cell lines provided a framework for interpreting the variation in gene expression patterns seen in the tumor samples and included gene expression models for many of the cell types encountered in tumors.

As described in more detail in Example 2, mRNA was isolated from each sample. cDNA labeled with the fluorescent dye Cy5 was prepared from each experimental sample separately. Fluorescently labeled cDNA, labeled using a second distinguishable dye (Cy3), was prepared from a pool of mRNAs isolated from 11 different cultured cell lines. The pooled mRNA sample served as a reference to provide a common internal standard against which each gene's expression in each experimental sample was measured.

Comparative expression measurements were made by separately mixing Cy5-labeled experimental cDNA derived from each of the 84 samples with a portion of the Cy3-labeled reference cDNA, and hybridizing each mixture to an individual cDNA microarray. The ratio of Cy5 fluorescence to Cy3 fluorescence measured at each cDNA element on the microarray was then quantitatively measured. The use of a common reference standard in each hybridization allowed the fluorescence ratios to be treated as comparative measurements of the expression level of each gene across all the experimental samples.

A hierarchical clustering method (Eisen, et al., 1998) was used to group genes based on similarity in the pattern with which their expression varied over all experimental samples. The same clustering method was used to group the experimental samples (tissue and cell lines separately) based on the similarity in their patterns of expression. Interpretation of the data obtained from the clustering algorithm was facilitated by displaying the data in the form of tumor and gene dendrograms. In the tumor dendrograms, the pattern and length of the branches reflects the relatedness of the tumor samples with respect to their expression of genes represented on the microarray. For example, Appendix A, part a shows a representative tumor dendrogram obtained by clustering the tumor samples based on their expression profiles with respect to 1753 of the genes represented on the cDNA microarrays. In general, the similarity of the gene expression profiles of individual tumor samples or groups of tumor samples to one another is inversely related to the length of the branches that connect them. Thus, for example, adjacent tumor samples connected to one another by short vertical branches descending from a common horizontal branch (e.g., tumor samples Norway 48-BE and Norway 48-AF close to the right of the tumor dendrogram) are more closely related to one another in terms of their gene expression profiles than adjacent tumor samples connected to one another by longer vertical branches descending from a common horizontal branch (e.g., tumor samples Norway 100-BE and Norway 100-AF at the left side of the tumor dendrogram). To the extent that the gene expression programs dictate the biological properties and behavior of the tumors and reflect their physiological state and environment, it is expected that the clustering of the tumors reflects phenotypic relationships among them, e.g., tumor samples connected by short horizontal branches (i.e., located in close proximity to one another) are expected to exhibit similar phenotypic features. In the gene dendrograms, the pattern and length of the branches reflects the relatedness of the genes with respect to their expression profiles across the tumor samples. Appendix D shows a representative gene dendrogram. Similarly to the tumor samples, genes connected by short vertical branches are more similar to one another in terms of expression profile than genes connected by longer vertical branches.

The expression patterns of the genes were also displayed using a matrix format, with each row representing all of the hybridization results for a single cDNA element on the array and each column representing the measured expression levels for all genes in a single sample. A representative matrix is shown in Appendix A, in which a set of 1753 differentially expressed genes was analyzed. Appendix A, part a shows a dendrogram representing similarities in the expression patterns between experimental samples. Appendix A, part b shows a scaled down version of the complete 1753 gene set. In this format, tumor samples with similar patterns of expression across the gene set are close to each other along the horizontal dimension. Similarly, genes with similar expression patterns across the set of samples are close to each other along the vertical dimension. To allow the patterns of expression to be visualized, the normalized expression value of each gene was represented by a colored box, using red to represent expression levels greater than the median and green to represent expression levels less than the median. In all images the brightest red color represents transcript levels at least 16-fold greater than the median, and the brightest green color represents transcript levels at least 16-fold below the median. This display format facilitates comparisons between genes and the recognition of significant patterns.

As described herein, systematic investigation of gene expression patterns in human breast tumors and their correlation to specific features of phenotypic variation offers a basis for an improved molecular taxonomy of breast cancers. Such a taxonomy has significant clinical utility. For example, correlation of gene expression patterns with outcome in the absence of treatment is of use in deciding whether a patient should receive adjuvant chemotherapy after surgery. As another example, genes whose expression level varies between tumors that are sensitive to chemotherapy and tumors that are resistant to chemotherapy are of use in predicting likelihood of response and in selection of appropriate treatment. Genes whose expression level varies between tumor samples taken before and after therapy are of use in understanding the response of tumors to treatment.

IV. Further Aspects of the Invention

A. Basal Tumor Subclasses and Corresponding Gene Subsets

Gene and tumor dendrograms were derived from data obtained by performing a microarray analysis on the set of breast tumor and breast tissue samples described above, using a set of genes (the "intrinsic" gene set) described further below and in Example 8. Appendices A and C present the resulting tumor dendrograms and color matrix displays of the gene expression profiles obtained. Although technically the dendrograms identify groups of tumor samples, since each sample is obtained from a specific tumor the dendrograms also identify groups of tumors. Thus, in general, a group of tumor samples corresponds to a group of tumors. Therefore, throughout most of the discussion herein reference will be made to tumor groups, classes, etc., rather than tumor sample groups, classes, etc. The clustering method permits the identification of subsets of genes with related expression profiles across a set of tumors and the identification of groups or classes of tumors with similar expression profiles across a set of genes. Although the existence of gene subsets is revealed by the display of the data in dendrogram format, understanding the significance of the gene subsets obtained in experiments such as those described above requires interpretation in light of knowledge about the genes and tumor samples. Groups of tumors identified based on their expression patterns of sets of genes (e.g., groups of tumors that overexpress genes in particular gene subsets) can be designated as tumor classes when deemed significantly distinct to warrant a distinct classification.

Table 5 includes information regarding the clinical outcome of the tumors from which the samples were obtained. In particular, the table includes survival time of the patients and, for some of the tumors, whether or not the tumor responded to chemotherapy (doxorubicin). Such information was used to demonstrate that the basal tumor class is characterized by a poor clinical outcome relative to the other tumors. Differences in survival between groups of patients was demonstrated using the Kaplan-Meier technique for survival analysis, which is implemented in computer software such as the SAS package (SAS Institute, Inc, Cary, N.C.) and described in the accompanying manual. Of course various other statistical techniques can be used to detect differences in survival or any other clinical parameters between groups of tumors. Various appropriate statistical techniques useful for analyzing survival are discussed, for example, in Lawless, J. F., *Statistical Models and Methods for Lifetime Data.* New York: John Wiley & Sons, 1982. Lee, Elisa T. *Statistical Methods for Survival Data Analysis.* 2nd ed. New York: John Wiley & Sons, 1992. Marubini, Ettore, and Valsecchi, Maria Grazia, *Analysing Survival Data from Clinical Trials and Observational Studies.* New York: John Wiley & Sons, 1995. Miller, Rupert G. Jr. *Survival Analysis.* New York: John Wiley & Sons, 1981. Rosner, Bernard, *Fundamentals of Biostatistics.* 4th ed. Belmont, Calif.: Duxbury Press, 1995.) Other clinical parameters of importance include response to therapy, time to recurrence, etc. As will be appreciated by one of ordinary skill in the art, the correlation of particular tumor groups with survival or other parameters of clinical importance can be strengthened by the inclusion of data obtained from additional tumor samples.

The invention identifies genes and gene subsets that are associated with the basal tumor subclass. The genes and gene subsets are identified in part by the overexpression of certain members of each subset in a particular tumor group and are also defined in part based on the proximity of genes within each subset to one another in a gene dendrogram. As used herein unless otherwise stated, a gene is overexpressed in a tissue sample at the RNA level if a mRNA corresponding to (i.e., transcribed from) the gene is present in excess relative to the median abundance of that mRNA across the set of analyzed specimens. A gene is overexpressed in a tissue sample at the protein level if a polypeptide corresponding to (i.e., translated from a mRNA that was transcribed from) the gene is present in excess relative to the abundance of that polypeptide across the set of analyzed specimens. The measurement of relative abundance using cDNA microarrays relies upon the comparison of all samples relative to a common reference sample that provides cognate mRNA for as many genes as possible with the goal of providing a common denominator for the measured ratios across all samples. Each tested sample can be compared to all other tested samples in ratio units relative to the reference. This allows reproducible determination of gene expression in each tested sample relative to the median gene expression across any given sample set (Ross, D T, et al., Systematic variation in gene expression patterns in human cancer cell lines, *Nat Genet.* 2000 24(3):227–35, 2000). In general, an appropriate reference sample comprises a renewable source of diverse cell samples such as a mixture of cells obtained from the panel of 11 cell lines listed in Table 3. A particularly preferred reference sample is one in which all relevant genes are represented in significant abundance above measured background. This provides for a reproducible measurement of reference signal for all relevant genes. As is well known in the art, there is generally a correlation between overexpression or underexpression at the RNA level and overexpression or underexpression at the protein level. In other words, if a mRNA is overexpressed then it is highly likely that the corresponding polypeptide is also overexpressed, and if a mRNA is underexpressed then it is highly likely that the corresponding polypeptide is underexpressed. Therefore, detection of either mRNA or a corresponding polypeptide is generally sufficient to determine whether a particular gene is over or underexpressed.

However, as is well known in the art, in certain situations it may be more convenient and/or practical to detect mRNA while in other situations it may be more convenient and/or practical to detect polypeptides.

As mentioned above, genes that are overexpressed in one or more samples may be identified by examining the microarray data displayed in matrix format, wherein red squares indicate overexpression. The basal gene subset includes a number of genes known to be expressed in basal epithelial cells (e.g., cytokeratins 5 and 17) and is characterized in that certain of the genes in the subset are overexpressed at the RNA level in samples obtained from a subset of tumors that had a poor prognosis relative to the entire group of tumors (the basal group). Referring to Appendix C, the basal gene subset comprises two subsets identified with a blue bar and a green bar along the side of the color matrix in part b and shown in expanded form in parts e and f. The clones that identify the genes in these two basal subsets are listed by their Genbank accession numbers in Table 9. As is evident from examination of Appendix C, parts e and f, genes in the basal gene subset are, in general, overexpressed in tumors in the basal tumor group (identified with orange dendrogram branches). Of course it will be appreciated that additional genes, not necessarily falling into either of the two basal gene subsets, also have an expression pattern similar to that of cytokeratin 5 and/or cytokeratin 17.

It will be appreciated that not all of the genes are overexpressed to a similar extent within a particular group of tumors and that expression of any given gene will likely vary between different tumors in a group. For example, as shown in Appendix C, part c, genes identified as "Cytochrome P450, subfamily IIA" and "Lymphoid nuclear protein related to AF4" are significantly overexpressed in tumors at the far right of the luminal tumor group (Stanford 24, Norway 27, 28, 26, and 56) while they are expressed at lesser levels in other members of the luminal tumor group. Conversely, genes identified as "417081" and "Homo Sapiens PWD gene mRNA, 3' end" are, in general, relatively underexpressed in these tumors. However, the overall expression patterns of genes in each subset over all tissue samples, are sufficiently similar to cause them to cluster in close proximity on the gene dendrogram. Thus whether a gene is a member of one of the inventive gene subsets is not determined solely on the basis of the overexpression of that gene within a tumor subset but also on the relationship of the overall expression pattern of the gene to the expression pattern of other genes within the subset. It will further be appreciated that a gene may be overexpressed in more than one tumor group. For example, certain of the genes in the basal subset are expressed in a group identified with green dendrogram branches, which includes both tumor and normal tissue samples, in addition to being overexpressed in the basal tumor group.

B. Diagnostics and Methods of use Thereof

The invention provides reagents for detecting expression products of the basal marker genes described herein, i.e., cadherin3, matrix metalloproteinase 14, and cadherin EGF LAG seven-pass G-type receptor 2. Detection of these expression products identifies tumors in the basal tumor subclass. While not wishing to be bound by any theory, inventors suggest that breast carcinoma with basal cell like features has distinguishing biology that could be targeted in therapeutic development. Once therapeutics targeted at such tumors are identified (as described elsewhere herein), detection of these expression products allows identification of subjects likely to benefit from these therapeutics. In addition, since the invention has established a correlation between the expression of the three basal marker genes and the expression of cytokeratinl7 and also established that cytokeratin 5/6 and/or cytokeratin 17 expression in breast tumors correlates with a poor outcome, detection of expression of the basal marker genes is useful in guiding therapeutic decisions in general. If it is known that a patient has a tumor that falls into the basal tumor subclass and thus has a poor prognosis, a more aggressive approach to therapy may be warranted than in tumors not falling within the basal subclass. For example, in patients where there is no evidence of disease in lymph nodes (node-negative patients), a decision must be made regarding whether to administer chemotherapy (adjuvant therapy) following surgical removal of the tumor. While some patients are likely to benefit from such treatment, it has significant side effects. Presently it is difficult or impossible to predict which patients would benefit. Knowing that a patient falls into a poor prognosis category may help in this decision. Of note, inventors showed that in node-negative patients cytokeratin 5/6 and/or 17 expression was a prognostic factor independent of tumor size and tumor grade. See Example 13 for further discussion of these issues and inventor's findings. Detecting expression of the basal marker genes of the present invention may provide information related to tumor progression. It is well known that as tumors progress, their phenotypic characteristics may change. The invention contemplates the possibility that breast tumors may evolve from luminal-like to basal-like (or vice versa), and that detection of expression products of the basal marker genes can be used to detect such progression.

It is well known in the art that some tumors respond to certain therapies while others do not. In general there is very little information that may be used to determine, prior to treatment, the likelihood that a specific tumor will respond to a given therapeutic agent. Many compounds have been tested for anti-tumor activity and appear to be effective in only a small percentage of tumors. Due to the current inability to predict which tumors will respond to a given agent, these compounds have not been developed into marketed therapeutics. This problem reflects the fact that current methods of classifying tumors are limited. However, the present invention offers the possibility of identifying tumor subgroups characterized by a significant likelihood of response to a given agent. Tumor sample archives containing tissue samples obtained from patients that have undergone therapy with various agents are available along with information regarding the results of such therapy. In general such archives consist of tumor samples embedded in paraffin blocks. These tumor samples can be analyzed for their expression of polypeptides encoded by the basal marker genes of the present invention. For example, immunohistochemistry can be performed using antibodies that bind to the polypeptides. Tumors belonging to the basal tumor subclass may then be identified on the basis of this information. It is then possible to correlate the expression of the basal marker genes with the response of the tumor to therapy, thereby identifying particular compounds that show a superior efficacy in tumors in this class as compared with their efficacy in tumors overall or in tumors not falling within the basal tumor subclass. Once such compounds are identified it will be possible to select patients whose tumors fall into the basal tumor subclass for additional clinical trials using these compounds. Such clinical trials, performed on a selected group of patients, are more likely to demonstrate efficacy. The reagents provided herein, therefore, are valuable both for retrospective and prospective trials.

In the case of prospective trials, detection of expression products of one or more of the marker genes may be used to stratify patients prior to their entry into the trial or while they are enrolled in the trial. In clinical research, stratification is the process or result of describing or separating a patient population into more homogeneous subpopulations according to specified criteria. Stratifying patients initially rather than after the trial is frequently preferred, e.g., by regulatory agencies such as the U.S. Food and Drug Administration that may be involved in the approval process for a medication. In some cases stratification may be required by the study design. Various stratification criteria may be employed in conjunction with detection of expression of one or more basal marker genes. Commonly used criteria include age, family history, lymph node status, tumor size, tumor grade, etc. Other criteria including, but not limited to, tumor aggressiveness, prior therapy received by the patient, ER and/or PR positivity, Her2neu status, p53 status, various other biomarkers, etc., may also be used. Stratification is frequently useful in performing statistical analysis of the results of a trial. Ultimately, once compounds that exhibit superior efficacy against breast basal tumors are identified, reagents for detecting expression of the basal marker genes may be used to guide the selection of appropriate chemotherapeutic agent(s).

In summary, by providing reagents and methods for classifying tumors based on their expression of the basal marker genes, the present invention offers a means to individualize therapy. The invention further provides a means to identify a patient population that may benefit from potentially promising therapies that have been abandoned due to inability to identify the patients who would benefit from their use.

Information regarding the expression of the basal marker genes is useful even in the absence of specific information regarding their biological function or role in tumor development, progression, maintenance, or response to therapy. Although the reagents disclosed herein find particular application with respect to breast cancer, the invention also contemplates their use to provide diagnostic and/or prognostic information for other cancer types. As is well known in the art, mutations in a single gene (e.g., the p53 gene) may play a role in the development of multiple cancer types. Thus it is contemplated that some or all of the basal marker genes described herein will be important both in breast cancer and in one or more other tumor types, particularly since basal cells are a feature of epithelia throughout the body.

In one aspect, the invention provides a method of classifying tumors by detecting the presence of one or more of the inventive gene products encoded by the cadherin3, matrix metalloproteinase 14, and cadherin EGF LAG seven-pass G-type receptor 2 genes. As is well known in the art, a polypeptide may be detected using a variety of techniques that employ an antibody that binds to the polypeptide. As described further below, these techniques include enzyme-linked immunosorbent assay (ELISA), immunoblot, and immunohistochemistry. The invention encompasses the use of protein arrays, including antibody arrays, for detection of the polypeptide. The use of antibody arrays is described, for example, in Haab, B., et al., "Protein microarrays for highly parallel detection and quantitation of specific proteins and antibodies in complex solutions", *Genome Biol.* 2001;2(2), 2001. Other types of protein arrays are known in the art.

In addition, in certain embodiments of the invention the polypeptides are detected using other modalities known in the art for the detection of polypeptides, such as aptamers (Aptamers, *Molecular Diagnosis,* Vol. 4, No. 4, 1999), reagents derived from combinatorial libraries for specific detection of proteins in complex mixtures, random peptide affinity reagents, etc. In general, any appropriate method for detecting a polypeptide may be used in conjunction with the present invention, although antibodies may represent a particularly appropriate modality.

The invention provides antibodies to the polypeptides encoded by the encoded by the cadherin3, matrix metalloproteinase 14, and cadherin EGF LAG seven-pass G-type receptor 2 genes. Example 10 describes the generation of polyclonal antibodies to these polypeptides. In general, antibodies (either monoclonal or polyclonal) may be generated by methods well known in the art and described, for example, in Harlow, E., Lane, E., and Harlow, E., (eds.) *Using Antibodies: A Laboratory Manual,* Cold Spring Harbor Laboratory Press, Cold Spring Harbor, 1998. Details and references for the production of antibodies based on an inventive polypeptide may also be found in U.S. Pat. No. 6,008,337. Antibodies may include, but are not limited to, polyclonal, monoclonal, chimeric (e.g., "humanized"), and single chain antibodies, and Fab fragments, antibodies generated using phage display technology, etc. The invention encompasses "fully human" antibodies produced using the XenoMouse™ technology (AbGenix Corp., Fremont, Calif.) according to the techniques described in U.S. Pat. No. 6,075,181.

The invention encompasses a number of uses for these antibodies. Detection of the basal marker polypeptides may be used to provide diagnostic information. As used herein the term "diagnostic information" includes, but is not limited to, any type of information that is useful in determining whether a patient has, or is at increased risk for developing, a disease or disorder; for providing a prognosis for a patient having a disease or disorder; for classifying a disease or disorder; for monitoring a patient for recurrence of a disease or disorder; for selecting a preferred therapy; for predicting the likelihood of response to a therapy, etc. In certain embodiments of the invention, the antibodies are used for providing diagnostic information for cancer, particularly for breast cancer, but they may also be of use for providing diagnostic information for other diseases, e.g., other types of cancer.

In general, diagnostic assays in which the antibodies may be employed include methods that use the antibody to detect the polypeptide in a tissue sample, cell sample, body fluid sample (e.g., serum), cell extract, etc. Such methods typically involve the use of a labeled secondary antibody that recognizes the primary antibody (i.e., the antibody that binds to the polypeptide being detected). Depending upon the nature of the sample, appropriate methods include, but are not limited to, immunohistochemistry, radioimmunoassay, ELISA, immunoblotting, and FACS analysis. In the case where the polypeptide is to be detected in a tissue sample, e.g., a biopsy sample, immunohistochemistry is a particularly appropriate detection method. Techniques for obtaining tissue and cell samples and performing immunohistochemistry and FACS are well known in the art. Such techniques are routinely used, for example, to detect the ER in breast tumor tissue or cell samples. In general, such tests will include a negative control, which can involve applying the test to normal tissue so that the signal obtained thereby can be compared with the signal obtained from the sample being tested. In tests in which a secondary antibody is used to detect the antibody that binds to the polypeptide of interest, an appropriate negative control can involve performing the test on a portion of the sample with the omission of the antibody that binds to the polypeptide to be detected, i.e., with the omission of the primary antibody. Antibodies suitable for use as diagnostics generally exhibit high specificity for the target polypeptide and low background. In general, monoclonal antibodies are preferred for diagnostic purposes.

In general, the results of such a test can be presented in any of a variety of formats. The results can be presented in a qualitative fashion. For example, the test report may indicate only whether or not a particular polypeptide was detected, perhaps also with an indication of the limits of detection. The results may be presented in a semi-quantitative fashion. For example, various ranges may be defined, and the ranges may be assigned a score (e.g., 1+ to 4+) that provides a certain degree of quantitative information. Such a score may reflect various factors, e.g., the number of cells in which the polypeptide is detected, the intensity of the signal (which may indicate the level of expression of the polypeptide), etc. The results may be presented in a quantitative fashion, e.g., as a percentage of cells in which the polypeptide is detected, as a protein concentration, etc. As will be appreciated by one of ordinary skill in the art, the type of output provided by a test will vary depending upon the technical limitations of the test and the biological significance associated with detection of the polypeptide. For example, in the case of certain polypeptides a purely qualitative output (e.g., whether or not the polypeptide is detected at a certain detection level) provides significant information. In other cases a more quantitative output (e.g., a ratio of the level of expression of the polypeptide in the sample being tested versus the normal level) is necessary.

Sequence analysis of two of the basal marker proteins, matrix metalloproteinase 14 and cadherin EGF LAG seven-pass G-type receptor 2 indicates that they possess one or more transmembrane domains and an extracellular portion. Sequence analysis of the third basal marker protein, cadherin3, indicates that it also has an extracellular portion. The invention encompasses the recognition that since these proteins have an extracellular domain, the likelihood exists that a portion of these proteins may therefore be present in serum (e.g., the portion may be cleaved by endogenous proteases and released into the bloodstream), enabling their detection through a blood test rather than requiring a biopsy specimen. Regardless of whether the proteins are present in serum, the likelihood that cadherin3, cadherin EGF LAG seven-pass G-type receptor 2, and matrix metalloproteinase 14 are membrane bound makes them attractive candidates for antibody diagnostics. The proteins may be detected on cells that enter the bloodstream or in samples obtained from a tumor site (e.g., cell or tissue samples).

Measurement of prostate specific antigen (PSA) in serum using an immunoassay technique is widely used as a method for early detection of prostate cancer and for monitoring recurrence or progression after therapy, etc. Methods and considerations in the use of this clinical marker are described, for example, in Chen D W, et al. Prostate-specific antigen as a marker for prostate cancer: A monoclonal and polyclonal immunoassay compared. *Clin Chem,* 33:1916–1920, 1987; Oesterling J E, et al. Free, complexed and total serum prostate specific antigen: The establishment of appropriate reference ranges for their concentrations and ratios. *J Urol* 154:1090–1095, 1995; Hybritech Tandem®-MP Free PSA. Package insert. March 1998 and Hybritech Tandem® Total PSA. Package insert., Hybritech, Inc., San Diego, Calif. One of ordinary skill in the art will readily be able to develop appropriate assays for polypeptides encoded by the basal marker genes described herein and to apply them to the detection of such polypeptides in serum. Such assays may be used as screening tests for cancer, to detect recurrence or progression of cancer, to monitor the response of cancer to therapy, to classify and/or provide prognostic information regarding a tumor, etc.

In certain embodiments of the inventive methods a single antibody is used whereas in other embodiments of the invention multiple antibodies, directed either against the same or against different polypeptides can be used to increase the sensitivity or specificity of the test or to provide more detailed information than that provided by a single antibody. Thus the invention encompasses the use of a battery of antibodies that bind to polypeptides encoded by the basal marker genes identified herein. Of course these antibodies can also be used in conjunction with antibodies against other polypeptides, including antibodies that bind to cytokeratin 5/6 or 17.

Various other techniques for detecting the basal marker polypeptides identified herein are within the scope of the invention. For example, a basal marker polypeptide may be detected using an assay for a biochemical activity of the polypeptide, e.g., an enzymatic activity. This type of assay may be especially convenient for tests on samples such as blood or other body fluids. Such an approach may be particularly attractive in the case of matrix metalloproteinase 14. As described above, matrix metalloproteinases are involved in cleavage of various proteins in the extracellular matrix. The cleavage specificity of this protein may readily be determined, and an appropriate substrate prepared. (See, e.g., Turk, B., et a)., "Determination of protease cleavage site motifs using mixture-based oriented peptide libraries", *Nature Biotechnology,* 19(7): 661–667, 2001, which discusses cleavage site motifs for various metalloproteases including MMP14, referred to as MT1-MMP therein.) Cleavage of this substrate may then be detected. In certain embodiments of the invention the substrate includes a fluorescent moiety for convenient detection. The invention contemplates use of fluorescent resonance energy transfer (FRET) assays to detect matrix metalloproteinase 14 (see www.aurorabio.com).

Although in many cases detection of polypeptides using antibodies represents the most convenient means of determining whether a gene is expressed (or overexpressed) in a particular sample, the invention also encompasses the use of polynucleotides for this purpose. Microarray analysis is but one means by which polynucleotides can be used to detect or measure gene espression. Expression of a gene can also be measured by a variety of techniques that make use of a polynucleotide corresponding to part or all of the gene rather than an antibody that binds to a polypeptide encoded by the gene. Appropriate techniques include, but are not limited to, in situ hybridization, Northern blot, and various nucleic acid amplification techniques such as PCR, quantitative PCR, and the ligase chain reaction.

One detection method involves performing quantitative PCR on a diagnostic sample using a set of oligonucleotide primers designed to amplify the genes in one or more of the inventive gene sets of gene subsets. (Considerations for primer design are well known in the art and are described, for example, in Newton, et al. (eds.) *PCR: Essential data Series,* John Wiley & Sons; *PCR Primer: A Laboratory Manual,* Cold Spring Harbor Laboratory Press, Cold Spring Harbor, N.Y., 1995; White, et al. (eds.) *PCR Protocols: Current methods and Applications,* Methods in Molecular Biology, The Humana Press, Totowa, N.J., 1993. In addition, a variety of computer programs known in the art may be used to select appropriate primers.)

According to one embodiment of this method the diagnostic sample is distributed into multiple vessels, e.g., multiple wells of a 396 well microtiter plate. A pair of primers designed to amplify a portion of a gene in one of the inventive gene sets or subsets is added to each well, and PCR amplification is performed. The resulting product can then be detected using any of a number of methods known in the art depending upon the particular method of performing quantitative PCR that is employed. Primers sufficient for amplification of genes that allow quantitation of different cell types within the sample may also be included in the set of primers.

The invention also encompasses the detection of mutations within any of the basal marker genes or within a regulatory region of a basal marker gene. Such mutations may include, but are not limited to, deletions, additions, substitutions, and amplification of regions of genomic DNA that include all or part of a gene. Methods for detecting such mutations are well known in the art. Such mutations may result in overexpression or inappropriate expression of the gene. Detection of mutations can be used, for example, to predict the likelihood that an individual will develop a condition associated with the mutation.

Another aspect of the invention comprises a kit to test for the presence of any of the inventive polynucleotides or polypeptides, e.g., in a tissue sample or in a body fluid. The kit can comprise, for example, an antibody for detection of a polypeptide or a probe for detection of a polynucleotide. In addition, the kit can comprise a reference or control sample, instructions for processing samples, performing the test and interpreting the results, buffers and other reagents necessary for performing the test. In certain embodiments of the invention the kit comprises a panel of antibodies. In certain embodiments of the invention the kit comprises pairs of primers for detecting expression of one or more of the basal marker genes. In certain embodiments of the invention the kit comprises a cDNA or oligonucleotide array for detecting expression of one or more of the basal marker genes.

D. Therapeutics

The invention encompasses the use of the basal marker genes and their expression products as targets for the development of therapeutics. The invention specifically encompasses antagonists to the basal marker genes and their expression products. Such antagonists (which include, but are not limited to, antibodies, small molecules, antisense nucleic acids) may be produced or identified using any of a variety of methods known in the art. For example, a purified polypeptide or fragment thereof may be used to raise antibodies or to screen libraries of compounds to identify those that specifically bind to the polypeptide. The likelihood that cadherin3, cadherin EGF LAG seven-pass G-type receptor 2, and matrix metalloproteinase 14 are membrane bound makes them attractive candidates for antibody therapeutics.

Preferably antibodies suitable for use as therapeutics exhibit high specificity for the target polypeptide and low background binding to other polypeptides. In general, monoclonal antibodies are preferred for therapeutic purposes. In the case of breast cancer, antibodies against the HER2/neu/ErbB2 polypeptide (a polypeptide homologous to the epidermal growth factor receptor) represent a paradigm in terms of the development of therapeutic antibodies. The HER2/neu/ErbB2 gene is overexpressed in approximately 25 to 30 percent of metastatic breast tumors, and an antibody against the HER2/neu/ErbB2 polypeptide, Herceptin® (Trastuzumab) is approved for the treatment of certain patients with metastatic breast cancer, confirming the utility of therapeutic antibodies directed against polypeptides that are specifically overexpressed in particular tumors subsets.

Proteins that are expressed on the cell surface, such as the basal marker proteins described herein, represent preferred targets for the development of therapeutic agents, particularly therapeutic antibodies. The presence of these proteins on the cell surface can be confirmed using immunohistochemisty.

Antibodies directed against a polypeptide expressed by a cell may have a number of mechanisms of action. In certain instances, e.g., in the case of a polypeptide that exerts a growth stimulatory effect on a cell, antibodies may directly antagonize the effect of the polypeptide and thereby arrest tumor progression, trigger apoptosis, etc. While not wishing to be bound by any theory, it may be particularly likely that certain genes that are overexpressed in tumors having a poor prognosis (e.g., genes in the basal gene subsets) encode polypeptides that have a growth stimulatory effect on tumor cells or facilitate the growth of such cells in some other way, e.g., by enhancing angiogenesis, by allowing cells to overcome normal growth regulatory mechanisms, or by blocking mechanisms that would normally lead to elimination of mutated or otherwise abnormal cells.

In certain embodiments of the invention the antibody may serve to target a toxic moiety to the cell. Thus the invention encompasses the use of antibodies that have been conjugated with a cytotoxic agent, e.g., a toxin such as ricin or diphtheria toxin, a radioactive moiety, etc. Such antibodies can be used to direct the cytotoxic agent specifically to cells that express the inventive polypeptide, particularly in the case of a polypeptide that is expressed on the cell surface.

Although certain antagonists may function through direct interaction with a polypeptide, e.g., by inhibiting its activity, others may function by affecting expression of the polypeptide. Reduction in expression of an endogenously produced polypeptide may be achieved by the administration of antisense nucleic acids (e.g., oligonucleotides, RNA, DNA, most typically oligonucleotides that have been modified to improve stability or targeting) or peptide nucleic acids comprising sequences complementary to those of the mRNA that encodes the polypeptide. Antisense technology and its applications are described in Phillips, M. I. (ed.) *Antisense Technology*, Methods Enzymol., Volumes 313 and 314, Academic Press, San Diego, 2000, and references mentioned therein. Ribozymes (catalytic RNA molecules that are capable of cleaving other RNA molecules) represent another approach to reducing gene expression. Such ribozymes can be designed to cleave specific mRNAs corresponding to a gene of interest. Their use is described in U.S. Pat. No. 5,972,621, and references therein. The invention encompasses the delivery of antisense and/or ribozyme molecules via a gene therapy approach in which vectors or cells expressing the antisense molecules are administered to an individual.

It may also be desirable to increase the expression of a gene in an inventive gene subset or to increase the activity of the corresponding polypeptide. For example, in the case of genes that are overexpressed in tumors having a good prognosis, e.g., certain genes in the luminal subset, it may be desirable to increase the expression of such genes or the activity of the corresponding polypeptides in tumors that fail to express these genes.

Small molecule modulators (e.g., inhibitors or activators) of gene expression are also within the scope of the invention and may be detected by screening libraries of compounds using, for example, cell lines that express the polypeptide or a version of the polypeptide that has been modified to include a readily detectable moiety. Methods for identifying compounds capable of modulating gene expression are described, for example, in U.S. Pat. No. 5,976,793. The screening methods described therein are particularly appropriate for identifying compounds that do not naturally occur within cells and that modulate the expression of genes of interest whose expression is associated with a defined physiological or pathological effect within a multicellular organism.

More generally, the invention encompasses compounds that modulate the activity of a basal marker gene of the present invention. Methods of screening for such interacting compounds are well known in the art and depend, to a certain degree, on the particular properties and activities of the polypeptide encoded by the gene. Representative examples of such screening methods may be found, for example, in U.S. Pat. Nos. 5,985,829, 5,726,025, 5,972,621, and 6,015,692. The skilled practitioner will readily be able to modify and adapt these methods as appropriate for a given polypeptide. Thus the invention encompasses methods of screening for molecules that modulate the activity of a polypeptide encoded by a basal marker gene.

The invention also encompasses the use of polynucleotide sequences corresponding to basal marker genes, or portions thereof, as DNA vaccines. Such vaccines comprise polynucleotide sequences, typically inserted into vectors, that direct the expression of an antigenic polypeptide within the body of the individual being immunized. Details regarding the development of vaccines, including DNA vaccines for various forms of cancer may be found, for example, in Brinckerhoff L. H., Thompson L. W., Slingluff C. L., Jr., Melanoma Vaccines, *Curr Opin Oncol,* 12(2):163–73, 2000 and in Stevenson, F. K., DNA vaccines against cancer: from genes to therapy, *Ann. Oncol.,* 10(12): 1413–8, 1999 and references therein. The polypeptides, or fragments thereof, that are encoded by genes in the inventive gene subsets may also find use as cancer vaccines. Such vaccines may be used for the prevention and/or treatment of cancer.

The invention includes pharmaceutical compositions comprising the inventive antibodies, or small molecule inhibitors, agonists, or antagonists described above. In general, a pharmaceutical composition will include an active agent in addition to one or more inactive agents such as a sterile, biocompatible carrier including, but not limited to, sterile water, saline, buffered saline, or dextrose solution. The pharmaceutical compositions may be administered either alone or in combination with other therapeutic agents including other chemotherapeutic agents, hormones, vaccines, and/or radiation therapy. By "in combination with", it is not intended to imply that the agents must be administered at the same time or formulated for delivery together, although these methods of delivery are within the scope of the invention. In general, each agent will be administered at a dose and on a time schedule determined for that agent. Additionally, the invention encompasses the delivery of the inventive pharmaceutical compositions in combination with agents that may improve their bioavailability, reduce or modify their metabolism, inhibit their excretion, or modify their distribution within the body. The invention encompasses treating cancer, particularly breast cancer, by administering the pharmaceutical compositions of the invention. Although the pharmaceutical compositions of the present invention can be used for treatment of any subject (e.g., any animal) in need thereof, they are most preferably used in the treatment of humans.

The pharmaceutical compositions of this invention can be administered to humans and other animals by a variety of routes including oral, intravenous, intramuscular, intraarterial, subcutaneous, intraventricular, transdermal, rectal intravaginal, intraperitoneal, topical (as by powders, ointments, or drops), bucal, or as an oral or nasal spray or aerosol. In general the most appropriate route of administration will depend upon a variety of factors including the nature of the compound (e.g., its stability in the environment of the gastrointestinal tract), the condition of the patient (e.g., whether the patient is able to tolerate oral administration), etc. At present the intravenous route is most commonly used to deliver therapeutic antibodies and nucleic acids. However, the invention encompasses the delivery of the inventive pharmaceutical composition by any appropriate route taking into consideration likely advances in the sciences of drug delivery.

General considerations in the formulation and manufacture of pharmaceutical agents may be found, for example, in *Remington's Pharmaceutical Sciences,* 19$^{th}$ ed., Mack Publishing Co., Easton, Pa., 1995. It will be appreciated that certain of the compounds of the present invention can exist in free form for treatment, or, where appropriate, in salt form, as discussed in more detail below. Compounds to be utilized in the pharmaceutical compositions include compounds existing in free form or pharmaceutically acceptable derivatives thereof, as defined herein, such as pharmaceutically acceptable salts, esters, salts of such esters, or any other adduct or derivative, which upon administration to a patient in need, is capable of providing, directly or indirectly, a compound as otherwise described herein, or a metabolite or residue thereof, e.g., a prodrug. Thus, as used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge, et al. describe pharmaceutically acceptable salts in detail in *J. Pharmaceutical Sciences,* 66: 1–19 (1977), incorporated herein by reference. The salts can be prepared in situ during the final isolation and purification of the compounds of the invention, or separately by reacting the free base function with a suitable organic acid. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid, or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate and aryl sulfonate.

Additionally, as used herein, the term "pharmaceutically acceptable ester" refers to esters that hydrolyze in vivo and include those that break down readily in the human body to leave the parent compound or a salt thereof. Suitable ester groups include, for example, those derived from pharmaceutically acceptable aliphatic carboxylic acids, particularly alkanoic, alkenoic, cycloalkanoic and alkanedioic acids, in which each alkyl or alkenyl moiety advantageously has not more than 6 carbon atoms. Examples of particular suitable esters includes formates, acetates, propionates, butyrates, acrylates and ethylsuccinates.

Furthermore, the term "pharmaceutically acceptable prodrugs" as used herein refers to those prodrugs of the compounds of the present invention that are, within the scope of sound medical judgment, suitable for use in contact with the tissues of humans and lower animals without undue toxicity, irritation, allergic response, and the like, commensurate with a reasonable benefit/risk ratio, and effective for their intended use, as well as the zwitterionic forms, where possible, of the compounds of the invention. The term "prodrug" refers to compounds that are rapidly transformed in vivo to yield a particular active compound, for example by hydrolysis in blood. A thorough discussion is provided in T. Higuchi and V. Stella, "Pro-drugs as Novel Delivery Systems", Vol. 14 of the A.C.S. Symposium Series, and in Edward B. Roche, ed., *Bioreversible Carriers in Drug Design,* American Pharmaceutical Association and Pergamon Press, 1987, both of which are incorporated herein by reference.

As mentioned above, the pharmaceutical compositions of the present invention additionally comprise a pharmaceutically acceptable carrier, which, as used herein, means a non-toxic, inert solid, semi-solid or liquid filler, diluent, encapsulating material, or formulation auxiliary of any type. Some examples of materials which can serve as pharmaceutically acceptable carriers are sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols; such a propylene glycol; esters such as ethyl oleate and ethyl laurate; agar; buffering agents such as magnesium hydroxide and aluminum hydroxide; alginic acid; water; isotonic saline; Ringer's solution; ethyl alcohol, and phosphate buffer solutions, dextrose solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

Liquid dosage forms for oral administration include pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a drug, it is often desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle. Injectable depot forms are made by forming microencapsulated matrices of the drug in biodegradable polymers such as polylactide-polyglycolide. Depending upon the ratio of drug to polymer and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions which are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar—gar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polethylene glycols and the like.

The active compounds can also be in micro-encapsulated form with one or more excipients as noted above. The solid dosage forms of tablets, dragees, capsules, pills, and granules can be prepared with coatings and shells such as enteric coatings, release controlling coatings, and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation and ear drops are also contemplated as being within the scope of this invention. The ointments, pastes, creams and gels may contain, in addition to an active compound of this invention, excipients such as animal and vegetable fats, oils, waxes, paraffins, starch, tragacanth, cellulose derivatives, polyethylene glycols, silicones, bentonites, silicic acid, talc and zinc oxide, or mixtures thereof. Powders and sprays can contain, in addition to the compounds of this invention, excipients such as lactose, talc, silicic acid, aluminum hydroxide, calcium silicates and polyamide powder, or mixtures of these substances. Sprays can additionally contain propellants known in the art such as chlorofluorohydrocarbons.

Transdermal patches have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

In yet another aspect, the present invention also provides a pharmaceutical pack or kit comprising one or more containers filled with one or more of the ingredients of the pharmaceutical compositions of the invention, and in certain embodiments, includes an additional approved therapeutic agent for use as a combination therapy. Optionally associated with such container(s) can be a notice in the form prescribed by a governmental agency regulating the manufacture, use or sale of pharmaceutical products, which notice reflects approval by the agency of manufacture, use or sale for human administration. Instructions for use of the compound(s) may also be included.

According to the methods of treatment of the present invention, cancer, particularly breast cancer, is treated or prevented in a patient such as a human or other mammal by administering to the patient a therapeutically effective amount of a compound of the invention, in such amounts and for such time as is necessary to achieve the desired result. By a "therapeutically effective amount" of a compound of the invention is meant a sufficient amount of the compound to treat (e.g. to ameliorate the symptoms of, delay progression of, prevent recurrence of, cure, etc.) cancer, particularly breast cancer, at a reasonable benefit/risk ratio, which involves a balancing of the efficacy and toxicity of the compound. In general, therapeutic efficacy and toxicity may be determined by standard pharmacological procedures in cell cultures or with experimental animals, e.g., by calculating the $ED_{50}$ (the dose that is therapeutically effective in 50% of the treated subjects) and the $LD_{50}$ (the dose that is lethal to 50% of treated subjects). The $ED_{50}/LD_{50}$ represents the therapeutic index of the compound. Although in general drugs having a large therapeutic index are preferred, as is well known in the art, a smaller therapeutic index may be acceptable in the case of a serious disease, particularly in the absence of alternative therapeutic options. Ultimate selection of an appropriate range of doses for administration to humans is determined in the course of clinical trials.

It will be understood that the total daily usage of the compounds and compositions of the present invention for any given patient will be decided by the attending physician within the scope of sound medical judgment. The specific therapeutically effective dose level for any particular patient will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts.

The total daily dose of the compounds of this invention administered to a human or other mammal in single or in divided doses can be in amounts, for example, from 0.01 to 50 mg/kg body weight or more usually from 0.1 to 25 mg/kg body weight. Single dose compositions may contain such amounts or submultiples thereof to make up the daily dose. In general, treatment regimens according to the present invention comprise administration to a patient in need of such treatment from about 0.1 ·g to about 2000 mg of the compound(s) of the invention per day in single or multiple doses.

EXAMPLES

Note: A numbered list of references appears following the Examples, all of which are incorporated herein by reference.

Example 1

Preparation of Microarrays Containing 8498 Human cDNAs

The human cDNA clones used in this study were obtained from Research Genetics (Huntsville AB, USA) as bacterial colonies in 96-well microtiter plates. The clones were chosen from a set of 15,000 cDNA clones that corresponded to the Research Genetics Human Gene Filters sets GF200–202 (www.resgen.com/). These clones form part of a set of clones assembled by the I.M.A.G.E. consortium (Lennon, G. G., Auffray, C., Polymeropoulos, M., Soares, M. B. The I.M.A.G.E. Consortium: An Integrated Molecular Analysis of Genomes and their Expression. Genomics 33:151–152, 1996) and are identified by I.M.A.G.E. clone ID numbers. All clones printed on these arrays were sequence validated as part of a product offered at Research Genetics, Inc. We estimate that greater than 97% of the clones on the array are correctly identified.

A detailed protocol for the production of the cDNA microarrays used in this study is available at cmgm.stanford.edu/pbrown/protocols.html and is reproduced below with insubstantial changes. As described below, the protocol includes steps of (1) cleaning the glass slides onto which the DNAs (e.g., products of PCR reactions) are to be spotted; (2) spotting the DNAs onto the glass slides with an arrayer; (3) Post processing to prepare arrays containing spotted DNAs for hybridization. All procedures are done at room temperature and with double distilled water unless otherwise stated. Unless otherwise stated, in this Example and the following Examples, reagents are prepared according to protocols available in Maniatis, T., Sambrook, J. and Fritsch, E., *Molecular Cloning: A Laboratory Manual* (3 Volume Set), Cold Spring Harbor Laboratory Press, Cold Spring Harbor, 1989.

Cleaning Slides
Use 30 slide racks in 350 mL glass dishes
 1. Dissolve 50 g of NaOH pellets into 150 ml ddH2O
 2. Add 200 ml of 95% EtOH, stir until completely mixed
 3. If solution remains cloudy, add ddH2O until clear
 4. Pour solution into glass slide box.
 5. Drop in 30 slides in a metal rack. (Gold Seal slides, Cat. 3010)
 6. Let soak on an orbital shaker for at least two hours
 7. Rinse slides by transferring rack to slide dish filled with ddH2O
 8. Repeat ddH2O rinses×3. It's important to remove all traces of the NaOH-ethanol.
 9. Prepare Poly-1-lysine solution: Use Sigma Poly-1-lysine solution. Cat. No. 8920
 10. Add 70 mL poly-1-lysine to 280 ml of water
 11. Transfer slides to poly-1-lysine solution and let soak for 1 hour.
 12. Remove excess liquid from slides by spinning the rack of slides on microtiter plate carriers at 500 rpm.
 13. Dry slides at 40 degrees C. for 5 minutes in a vacuum oven.
 14. Store slides in a closed box for at least two weeks prior to use.
 15. Before printing arrays, check a sample slide to make sure it's hydrophobic (water should bead off it) but the lysine coating is not turning opaque.

Arraying
 1. Transfer PCR reactions to 96-well V-bottom tissue culture plates (Costar). Add ⅟10 vol. 3M sodium acetate (pH 5.2) and equal volume isopropanol. Store at −20 C. for a few hours.
 2. Centrifuge in Sorvall at 3500 RPM for 45 min. Rinse with 70% EtOH, centrifuge again and dry.
 2. Resuspend DNA in 12 ul 3×SSC for a few hours and transfer to flexible U-bottom printing plates.
 4. Spot DNA onto poly-1-lysine slides with an arrayer.

Post Processing
 1. Rehydrate arrays by suspending slides over a dish of warm ddH2O. (~1 minute)
 2. Snap-dry each array (DNA side up) on a 100C hot plate for 3 seconds.
 3. UV cross-link DNA to the glass by using a Stratalinker set for 60 milliJoules
 4. Dissolve 5 g of succinic anhydride (Aldrich) in 315 mL of n-methyl-pyrrolidinone.
 5. To this, add 35 mL of 0.2M NaBorate pH 8.0 (made by dissolving boric acid in water and adjusting the pH with NaOH), and stir until dissolved.
 6. Soak arrays in this solution for 15 minutes with shaking.
 7. Transfer arrays to 95C water bath for 2 minutes
 8. Quickly transfer arrays to 95% EtOH for 1 minute.
 9. Remove excess liquid from slides by spinning the rack of slides on microtiter plate carriers at 500 rpm.
 10. Arrays can be used immediately.

Reagent Suppliers
Microscope slides Goldseal brand. (Cat. 3010)
Poly-1-lysine solution Sigma product number P8920
Succinic Anhydride Aldrich product number 23,969–0
N-Methyl-Pyrrolidinone Aldrich product number 32,863–4

Microarrays were prepared according to the above protocol using the 8498 cDNA clones described above. All microarrays used in the experiments described herein were from a single print run batch of microarrays.

Example 2

Cell Lines, Breast Tissue, and Breast Tumor Samples for Microarray Analysis and Preparation of mRNA Samples Common Reference Sample Each of the 84 experimental samples tested here was analyzed by a comparative hybridization, using a common reference RNA pool as a standard; this reference sample was composed of equal mixtures of mRNA isolated from 11 established cell lines derived from human tissue (MCF7, Hs578T, OVCAR3, HepG2, NTERA2, MOLT4, RPMI-8226, NB4+ATRA, UACC-62, SW872, and Colo205: also see Table 3 for more details). The 11 cell lines were all grown to 70–90% confluence in RPMI medium, containing 10% Fetal Calf Serum and Penicillin/Streptomycin. The cells were harvested either by scraping or centrifugation, quickly resuspended in RNA lysis buffer and mRNA prepared using the FastTrack™ 2.0 mRNA Isolation Kit (Invitrogen, Carlsbad, Calif.) according to the manufacturer's instructions. In each case, multiple individual mRNA preparations were collected for each cell line, which were then pooled together and analyzed via Northern analysis before final mixing to ensure the quality of the input mRNAs (e.g., to confirm that the mRNA exhibited a size distribution indicating that it was substantially nondegraded). The 11 mRNA samples were then mixed together in equal amounts, aliquoted in 10 mM Tris (7.4), and stored at −80 C until use (2 micrograms of common reference sample was used per microarray hybridization and was always labeled using Cy3).

Normal Breast Tissue

Three samples of normal breast tissue were analyzed. Two of the samples were obtained from Clontech (Palo Alto, Calif.) and were pools of six (Normal 1) or two (Normal2) whole normal breasts. The third sample (Normal3) was obtained from a single individual.

Breast Tumor Samples

The 40 individual breast tumor samples were collected at either Stanford University in Stanford Calif., USA, or in the Haukeland University Hospital in Bergen, Norway. Twenty of the forty breast tumors were sampled twice as part of a larger Norwegian study on locally advanced breast cancers (T3/T4 and/or N2 tumors) and have been described previously (Aas, T., et al., *Nat. Med.,* 2, 811–814, 1996, the contents of which are incorporated herein by reference); these patients underwent an open surgical biopsy before treatment with doxorubicin monotherapy (range 12–23 weeks), followed by the definitive surgical resection of the remaining tumor after therapy, and were evaluated for clinical responses according to UICC criteria (Hayward, J., et al., *Br. J. Cancer,* 35, 292–298, 1977). In addition to the 20 pairs, there were 8 additional "before" specimens from Norway and 10 tumor specimens from Stanford (all Stanford tumors tested had a diameter of 3 cm or larger). Finally, 2 of the 10 Stanford tumor specimens assayed were also paired with a lymph node metastasis from the same patient.

mRNA Isolation from Breast Tumor and Tissue Samples

Following their excision, breast tumor samples were rapidly frozen in liquid N2 and then stored at −80 C until use. mRNA was isolated from breast tumors and normal breast tissue using the Trizol Reagent (Gibco-BRL) and Invitrogen FastTrack 2.0 Kit (all Stanford samples, and see genome-www.stanford.edu/sbcmp/web.shtml for the detailed protocol) or using the Trizol Reagent followed by Dynal bead separation for the mRNA purification step (all Norway tissue samples). Briefly, frozen tumor samples were cut into small pieces and immediately placed into 12 ml of Trizol Reagent. Each tumor sample in Trizol was homogenized using a PowerGen 125 Tissue Homogenizer (Fisher Scientific), and total RNA was isolated according to the Trizol reagent manufacturer's protocol. Tumor mRNA was isolated according to the manufacturer's protocols using the FastTrack 2.0 Kit (Invitrogen) or Dynal beads.

Example 3

Characterization of Breast Tissue and Tumor Samples

For all but two of the tumor specimens (i.e. New York 1 and New York 2), the mutational status of the TP53 gene was determined using published methods (Aas, T., et al.).

A single pathologist (applicant Matt van de Rijn) reviewed hematoxylin and eosin (H&E) sections of each tumor, including all before and after pairs, and made a histological evaluation of each while blinded to the source. Tumors were graded using a modified version of the Bloom-Richardson method (Robbins, P., et al., *Hum Pathol,* 26, 873–879, 1995). These data are displayed in Appendix H, Table 4. Representative H&E sections of each tumor are posted on Applicants' website at genome-www.stanford.edu/molecularportraits/.

Immunohistochemistry was performed as described previously (Perou, C., et al., 1999; Bindl, J. and Warnke, R., *Am J Clin Pathol,* 85, 490–493, 1986, and Natkunam, Y., et al., Am. J. Path., 156(1), 2000). The antibodies used included the commercially available monoclonal antibodies CAM5.2 (specific for keratins 8/18, available from Becton Dickinson), anti-keratin 5/6 (available originally from Boehringer Mannheim, Indianapolis, Ind., cat. no. 1273396 and now from Chemicon International, Temekula, Calif.), anti-keratin 17 (clone E3, available from Dako, Carpinteria, Calif., cat. no. M7046), anti-CD3 (available from Dako), and anti-immunoglobulin light chain (A191, A193, available from Dako). These immunohistochemical methods were applied for all the immunohistochemical studies described in the present application unless otherwise stated. Results are presented in FIG. 3 and are described in further examples as appropriate.

Example 4 cDNA Synthesis and Labeling and Microarray Hybridization mRNA was isolated from breast tissue, breast tumor samples, and cell lines as described in Example 2. Fluorescently labeled cDNA was synthesized from the mRNA using a reverse transcriptase reaction that included dUTP labeled with either Cy3 or Cy5. For each hybridization experiment differentially labeled cDNA samples (an experimental sample and a reference sample) were pooled and hybridized to a cDNA microarray, which was then scanned as described in Example 4. The protocol below provides details of the steps performed for cDNA synthesis and labeling and for microarray hybridization.

1. To set up for the reverse transcriptase (RT) reaction, combine the following (e.g., in an Eppendorf tube):
    (a) Anchored Oligo dT primer—2 microliters at 2.5 micrograms/microliter or control—2 microliters.
    (b) mRNA—(whatever volume is needed to reach 1.5–2 micrograms)
    (c) DEPC/H2O—add sufficient volume so that final volume is 16 microliters
2. Heat at 70° C. for 10 minutes
3. Chill on ice for 1–2 minutes
4. Add the following RT reaction components to each individual tube:
    (a) 5X RT Buffer—6 microliters
    (b) 50X dNTPs—0.7 microliters—(500 mm A,C,G, 200 mm T)
    (c) Cy Dyes dUTP—3 microliters—(either Cy3 or Cy5)
    (d) DTT Stock—3 microliters—(comes with RT setup)
    (e) Superscript II R—1.7 microliters—(cat# 18064–014 Gibco-BRL)
5. Mix well
6. Incubate at 42° C. for 1 hour
7. Add another 1 microliter of Superscript II RT and mix
8. Incubate at 42° C. for 1 more hour
9. Degrade mRNA with 1.5 microliters of 1M NaOH/2 mM EDTA
10. Incubate at 65° C. for 8 minutes (do NOT go TOO long here)
11. Add 15 microliters of 0.1M HCL
12. Add 450 microliters of TE (pH 7.4) to each sample and place each sample into a microcon-30 filter.
13. Add 15 microliters of Human COT1 DNA (Gibco-BRL=1 microgram/microliter) to each sample in the microcon filter.
14. Spin in Eppendorf centrifuge until volume equals about 50 microliters (8–10')
15. Remove flowthroughs, and pool Cy3 and Cy5 flowthroughs together for future recovery of Cy dyes (store at −20·C).
16. Invert microcons, recover labeled samples, and pool Cy3 and Cy5 samples together that will be used for an individual experiment, in a single microcon filter that was used in step 15.
17. Add 500 microliters of T.E again, and spin until final volume equals 8 microliters or less (BE VERY CAREFUL TO NOT SPIN THE SAMPLE DRY!!!)
18. To the 8 microliter combined Cy3+Cy5 sample, add the following:
    (a) Yeast tRNA—1 microliter—(10 micrograms/microliter)
    (b) PolyA DNA—2 microliters—(10 micrograms/microliter)

(c) 20×SSC—2 microliters—(FINAL SSC concentration approximately 3×)
(d) 10% SDS—0.3 microliters
FINAL VOLUME=13.3 MICROLITERS
19. Mix well.
20. Heat sample at 100° C. for 2 minutes, spin very briefly.
21. Place samples at 42° C. for 20–30 minutes.
22. During Step 21, prepare the necessary number of hybridization chambers (Custom made by Die-Tech, San Jose, Calif. (see "Drawings for custom parts at cmgm.stanford.edu/pbrown/mguide/HybChamber.pdf") or purchased at Corning Costar, Acton, Mass. (CTMT™ Hybridization Chamber, #2551), get 22 mm×22 mm coverslips ready, and get arrays ready.
23. Add the 13 microliters of probe (i.e., labeled cDNA mixture) onto the center of the array while NOT actually touching the array face with the pipette tip.
24. Quickly and gently place the 22 mm×22 mm glass#1 coverslip onto the array face.
25. Add about 15–20 microliters of 3XSSC in two drops onto the end of the array slide away from the actual array for hydration purposes.
26. Assemble the hybridization chamber with the array slide in it, and place into a 65 C water bath overnight.
27. Pull out the hybridization chamber and dry off the excess $H_2O$.
28. Disassemble the hybridization chamber, and quickly place the slides into a slide washing chamber that contains 2×SSC/0.05% SDS. Jiggle the slide holder up and down until the slide coverslip falls off. Repeat this individually for each array, one at a time, until all are done
29. Wash slides in 1×SSC for 3–5 minutes.
30. Wash slides in 50 C 0.2×SSC for 3–5 minutes, twice.
31. Spin slides down in centrifuge at 200 RPM for 2 minutes.
32. SCAN immediately.

Example 5

Collection, Processing, and Analysis of Data from Microarray Hybridizations

The cDNA microarrays were scanned with either a General Scanning (Watertown, Mass.) ScanArray 3000 at 20 microns resolution, or with a prototype Axon Instruments (Foster City, Calif.) GenePix Scanner at 10 micron resolution. The output files, which were TIFF images, were then analyzed using the program ScanAlyze (M. Eisen; available at www.microarrays.org/software). Fluorescent ratios and quantitative data on spot quality (see ScanAlyze manual) were stored in a prototype of the AMAD) database (M. Eisen; available at www.microarrays.org/software). Areas of the array with obvious blemishes were manually flagged and excluded from subsequent analyses. The primary data tables can be downloaded at genome-www.stanford.edu/molecularportraits/, in text/tab delimited format after obtaining a password.

Data were extracted from the database in a single table, with each row representing an array element, each column a hybridization, and each cell the observed fluorescent ratio for the array element in the appropriate hybridization. Previously flagged spots were excluded, as were spots that did not pass quality control. This table had 9216 rows and 84 columns. Array elements were removed if they were not well measured in at least 80% of the hybridizations. The data table was split into tumors and cell lines, and the two subtables were separately median polished (the rows and columns were iteratively adjusted to have median 0) before being rejoined into a single table. Genes whose expression varied by at least 4-fold from the median in this sample set in at least three of the samples tested were selected for the analyses described in the Detailed Description and in Examples 6 and 7 (1753 genes satisfied these conditions).

Average-linkage hierarchical clustering, as implemented in the program Cluster (M. Eisen; www.microarrays.org/software), was applied separately to both the genes and arrays. The results were analyzed, and images generated, using TreeView (M. Eisen; www.microarrays.org/software).

Example 6

Molecular Portraits of Tumors Based on Variation in Expression of 1753 Genes

Methods

A hierarchical clustering method (Eisen, 1998) was used to group 1753 differentially expressed genes (i.e., those genes whose expression varied by at least 4-fold from the median in the sample set in at least three of the samples tested) based on similarity in the pattern with which their expression varied over all samples. The same clustering method was used to group the experimental samples (tissues and cell lines separately) based on the similarity in their patterns of expression. The expression patterns of the 1753 genes are displayed in Appendix A. In this illustration, the data are presented in a matrix format, with each row representing a single gene, and each column representing an experimental sample. The ratio of the abundance of transcripts of each gene, in each sample, to the median abundance of the gene's transcript among all the cell lines (left panel) or to its median abundance across all the clinical samples (right panel) is represented by the color of the corresponding cell in the matrix. Green squares represent transcript levels below the median; black squares represent transcript levels equal to the median; red squares represent transcript levels greater than the median; gray squares indicate technically inadequate or missing data. The color saturation reflects the magnitude of the ratio relative to the median for each set of samples (see scale at bottom left). In all images the brightest red color represents transcript levels at least 16-fold greater than the median, and the brightest green color represents transcript levels at least 16-fold below the median. The full gene cluster diagram is presented in Appendix D.

Results (i) Molecular Portraits of Tumors

Three striking general features of the tumors' ene expression patterns are evident in Appendices A and D. First, the breast tumors show remarkable variation in their patterns of gene expression. Second, this variation is multidimensional, that is, many different sets of genes show largely independent patterns of variation. Third, the patterns of gene expression have a pervasive order reflecting relationships among the genes, relationships among the tumors, and connections between specific genes and specific tumors.

The hierarchical clustering algorithm organized the experimental samples based only on overall similarity in their gene expression patterns; relationships among the experimental samples are summarized in a dendrogram (Appendix A, part a), in which the pattern and length of the branches reflect the relatedness of the samples (Eisen, M., et al., 1998). Fifteen of the 20 pairs of samples taken from the same tumor before and after doxorubicin chemotherapy (red dendrogram branches), and both pairs of samples taken from a primary tumor and an associated lymph node metastasis (blue branches) were clustered together on adjacent terminal branches in the dendrogram (Appendix A, part a). The three clustered normal breast samples are highlighted in green. The branches representing the four breast luminal epithelial cell lines are displayed in pink; breast basal epithelial cell lines are displayed in orange, the endothelial cell lines in blue, the mesynchemal-like cell lines in dark green, and the lymphocyte-derived cell lines in dark red.

As is evident from Appendix A, part a, application of the clustering method to the samples and genes identified the two members of each primary tumor/metastasis pair as being closely related to one another based on similarity in gene expression. Thus this method can provide information useful in determining whether a tumor sample obtained from a second tumor is a metastasis originating from a first tumor or is an independent primary tumor. In addition, despite the potential confounding effects of an interval of 16 weeks, independent surgical procedures and cytotoxic chemotherapy, the independent samples taken from the same tumor before and after chemotherapy were in most cases recognizably more similar to each other in their overall pattern of gene expression than either was to any of the other samples.

Closer examination of the five before and after pairs that were not matched by the clustering algorithm provided further insight. In three instances, the after chemotherapy specimens (i.e. Norway 47, 61, and 101) were clustered into a branch of the dendrogram that contained the three normal breast samples along with five additional tumor samples; we know from the clinical data that these three tumors were all classified as doxorubicin responders (Table 5 and Aas, T., et al.). Thus, in most cases, independent tumor biopsies from the same individual could be recognized as such solely on the basis of gene expression patterns. This implies that the patterns of gene expression are homogeneous and stable in each breast tumor, and yet, sufficiently diverse between tumors, so that they can be viewed as molecular portraits of each tumor.

(ii) Specific Properties of the Tumors

The molecular portraits revealed in the patterns of gene expression not only uncovered similarities and differences among the tumors but, in many cases, pointed to a biological interpretation. As discussed below, variation in growth rate, in the activity of specific signaling pathways, and in the cellular composition of the tumors were all reflected in corresponding variations in the expression of specific subsets of genes.

Growth and Proliferation. The largest distinct subset of genes among the 1753 genes presented in Appendix A was the proliferation subset, illustrated in Appendix B, which is a group of approximately 120 genes whose level of expression correlates with cellular proliferation rates (See Perou, C., et al., 1999; Ross, D., et al., *Nature Genetics,* 24(3): 227–35, 2000.). Expression of this subset of genes varied widely among the tumor samples, and was generally well correlated with a standard pathological index of tumor cell proliferation, namely the mitotic index. The mitotic grade of each tumor, as determined by evaluating mitotic index, is displayed in a color-coded format below the tumor name, with green indicating mitotic grade 1, black indicating mitotic grade 2, red indicating mitotic grade 3, and gray indicating that mitotic grade was not evaluated. The growth and proliferation cluster also included the genes encoding two widely used immunohistochemical markers of cell proliferation (Ki-67 and PCNA, names in blue/purple letters).

Diverse proliferation-related functions are represented in the genes comprising this subset, including macromolecular synthesis, cell-cycle regulation, mitosis and cytokinesis. Many genes in which alterations in sequence or expression that are associated with tumorigenesis were also found in this gene subset, in particular, numerous genes implicated in chromosomal instability and/or anueploidy (names in pink letters in Appendix B)[22]. These genes included the spindle checkpoint gene hBUB1[23], the human MAD2 homologue[24], the STK15/IPL1 kinase[25], and the PLK1/HSTPK13 kinase[26].

The importance of this clustered set of genes in cancer biology is further highlighted by its inclusion of genes encoding the molecular targets of widely used anticancer agents (names in orange letters in Appendix B), including both subunits of ribonucleotide reductase, topoisomerase II alpha, and dihydrofolate reductase. The many uncharacterized genes in this subset, therefore, are candidates for important roles in the regulation and execution of the cell's program for growth and proliferation, and potential targets for oncogenic mutations or antiproliferative drugs. Thus the clustering method, by generating a set of genes known to be involved in proliferation and/or known to be targets for antiproliferative drugs and further identifying a set of unknown genes whose expression patterns cause them to fall within the subset, identifies potential targets for the development of new chemotherapeutic agents.

Variation in signaling pathways. Several groups of co-expressed genes provided views of the activities of specific signaling and/or regulatory systems.

(a) Interferon signaling: A large subset of genes known to be regulated by the interferon pathway (including STAT1) showed substantial variation in expression among the tumors.

(b) Estrogen receptor: Variation in expression of the estrogen receptor alpha gene (ESR1) correlated well with the direct clinical measurement of the estrogen receptor protein levels in the tumors (Table 5, concordance in 36/38 tumors tested), and paralleled variation in the expression of a larger group of genes that included three other transcription factors (GATA-binding protein 3, X-box binding protein 1 and hepatocyte nuclear factor 3 alpha (see also references 27 and 28). In a specific subset of the estrogen receptor positive tumors, the BCL2 gene and two previously known estrogen regulated genes (LIV1 and trefoil factor 1[29]) were also highly expressed (See Appendices C and D). The regulatory program reflected in the expression of this ESR1-containing subset of genes may play an important role in the clinical course of a breast tumor, as the loss of expression of the estrogen receptor is known to be associated with a poor prognosis[17], while high levels of expression of both BCL2 and ESR1 are associated with a more favorable prognosis[30,31].

(c) Erb-B2: HER2/neu, also known as the Erb-B2 oncogene, is a gene whose aberrant expression is thought to contribute to tumorigenesis in the breast[16]. The Erb-B2 receptor-tyrosine kinase is known to be overexpressed in 20–30% of all breast tumors, usually associated with DNA amplification of the chromosomal locus (17q12-q22) that contains the ERB-B2 gene[32,33]. Interestingly, most of the other genes contained within the Erb-B2 cluster were also located in this same small region of Chromosome 17 (Appendix C, part d and Appendix D). These expression data suggested, and the results of microarray comparative genomic hybridization confirmed, that these other closely linked genes were also amplified on the genomic DNA level and, consequently, overexpressed on the mRNA level in tumors with an amplified Erb-B2 gene[33–35].

(d) Fos/Jun Signaling: A subset of genes that included c-Fos, JunB, and other genes involved in the "immediate-early" response to serum, co-varied in expression among the tumor specimens (See Appendix D); these genes were most highly expressed in the three normal breast samples. Applicants have found that this set of genes is characteristically induced by prolonged handling of the samples following surgical resection. The observed variation in the expression of this set of genes may therefore reflect variation in post surgical handling rather than true in vivo differences.

Example 7

Identification of Cell Type Specific Components Within Tumors Based on Variation in Expression of 1753 Genes Methods and Rationale Clustering was performed as described in the previous Example. The resulting dendrogram and matrix were used to identify gene expression patterns indicative of the presence of certain cell types within the samples. Human breast tumors are histologically complex tissues, containing a variety of cell types in addition to the carcinoma cells[18]. In analyzing the gene expression patterns in tumors and tissues, two lines of reasoning were used to infer the lineage of the cells that accounted for apparently cell-type specific expression of particular clustered groups of genes. First, such gene subsets usually included genes whose expression patterns have been well characterized by previous workers, and have consistently pointed to a specific cell type. Second, these inferences were often corroborated by observing comparable expression of the same group of genes in one or more of the cultured cell lines (Appendix A and reference 21). Some of the prominent patterns of gene expression that appear, on this basis, to indicate the variable abundance of particular cell types in these tissue samples are summarized below.

Immunohistochemistry was performed as described in Example 3.

Results

At least eight subsets of genes appeared to reflect variation in specific cell types present within the tumors (Appendices A and D). Appendix A, part b presents a scaled down representation of the complete 1753 gene cluster diagram; the colored bars to the right identify the locations of the inserts displayed in 1c-j, each of which represents a portion of a gene subset associated with one of the cell types/populations described below.

The notion that developmental lineage has a pervasive influence on gene expression patterns is highlighted by the clustering pattern of the cultured cell lines in Appendix A. For example, the three lymphocyte cell lines comprise one branch, the two endothelial cell lines constitute another and the mesenchymal cell lines form a third. Cell lines derived from two distinct types of breast epithelial cells (basal and luminal) also formed distinct dendrogram branches. Some of the prominent patterns of gene expression that appear to indicate the variable abundance of particular cell types within a tumor sample are summarized in the remainder of this Example.

(a) Endothelial cells: A subset of genes characteristically expressed by endothelial cells, including CD34, CD31 and von Willebrand Factor[36,37] were also strongly expressed in the two endothelial cell lines HUVEC and HMVEC (Appendix A, part c). Variation among the tumor samples in the abundance of transcripts from this subset of genes may therefore reflect variation in the vascularity or angiogenic activity within the tumors.

(b) Stromal cells: A previously characterized subset of genes that included multiple isoforms of collagen and other genes encoding extracellular matrix components, many of which are characteristically expressed by mesenchymal cells, showed significant variation in expression among the tumor samples (Appendix A, part d)[8,21].

(c) Adipose-Enriched/Normal Breast: A subset of genes that included fatty acid binding protein 4 and PPAR• may represent the presence of adipose cells in the tumor samples[38,39]. This subset of genes was most highly expressed in the three normal breast samples (Appendix A, part g). As we have no cell line guide for this cluster, the exact nature of the cell type underlying expression of these genes cannot be unequivocally determined.

(d) B-lymphocytes: Variation in expression of a subset of genes that were highly expressed in RPMI-8226 (a multiple myeloma-derived cell line), including many immunoglobulin genes, appears to represent variable B-cell infiltration of the tumors. This interpretation was corroborated by immunohistochemistry (Appendix A, part f)[8,21].

(e) T-lymphocytes: One subset of co-expressed genes included CD3, and two subunits of the T-cell receptor (Appendix A, part i). Most of the genes in this subset were expressed at their highest levels in the T-cell leukemia derived cell line, MOLT-4. Variation in expression of this subset of genes was therefore interpreted as representing variation in T-lymphocyte populations in the tumors. Immunohistochemical staining of tumor samples, using anti-CD3 antibodies, confirmed that tumors with the highest levels of expression of this subset of genes contained numerous CD3-positive lymphocytes (FIG. 3b).

(f) Macrophages: A subset of genes that appeared to be markers of macrophage/monocyte populations included CD68, acid phosphatase 5, chitinase, and lysozyme (Appendix A, part h). Interestingly, the transcripts for these genes were the most abundant in the three after chemotherapy tumor samples that clustered apart from their before counterparts (i.e. Norway 47, 61, and 101). These three tumors, all of which had responded to the chemotherapy, were thus notable not only for an overall gene expression pattern resembling that of normal breast tissue, but also, for a particularly large population of macrophages, perhaps representing a secondary response to tumor necrosis.

(g) Basal and Luminal Epithelial Cells of the Mammary Duct, and Their Malignant Counterparts: Two distinct kinds of epithelial cells are found in the adult human mammary gland, basal (and/or myoepithelial cells) and luminal epithelial cells[18,40]. These two cell types are conveniently distinguished immunohistochemically; basal epithelial cells can be stained with antibodies to keratin 5/6 (FIG. 3c), while luminal epithelial cells stain with antibodies against keratins 8/18 (FIG. 3c). Many genes were expressed by one of these two cell lines, but not by the other (Appendix A, parts e, f, and j and Appendix D). The gene expression subsets characteristic of basal epithelial cells included several genes that have previously been shown to play important roles in this cell type, e.g., keratin 5, keratin 17, integrin-•4 and laminin (Appendix A, parts e and f)[18]. The gene expression subset characteristic of luminal cells was anchored by the previously noted subset of transcription factors that included the estrogen receptor gene (Appendix A, part j).

Example 8

Classification of Breast Tumors Using an Optimized Set of Genes Showing Differential Expression Between Tumors Methods and Rationale As described in Examples 6 and 7, analysis of genes that are differentially expressed in breast tumor samples provides an indication of the relatedness of the samples and allows identification of samples taken from the same tumor or members of a tumor/metastasis pair. Such analysis further provides insight into specific tumor properties such as variation in growth rate, activity of specific signaling pathways, and the cellular composition of the tumors. The subset of genes analyzed in Examples 6 and 7 was selected solely based upon the fact that genes in the subset were differentially expressed among the experimental samples. Recognizing that the choice of genes whose expression levels provide the basis for the ordering of the tumor samples determines which phenotypic relationships among the tumors are reflected in the clustering patterns, applicants devised methods for selecting subsets of genes optimized to reflect phenotypic relationships among the tumors.

(i) Selection of an Intrinsic Gene Subset

The rationale behind the first optimized gene subset was Applicants' recognition that specific features of a gene expression pattern that are to be used as the basis for classifying tumors should typify• that tumor; that is, these features should be similar in any sample taken from the same tumor, and they should vary among different tumors. The 22 pairs of independent samples taken from 22 different tumors provided an opportunity for the selection of genes that fulfill these criteria. To select a set of genes whose variation in expression optimally represented differences between tumors rather than just differences between tumor samples, a "within-between" score was assigned to each gene equal to the mean effect of the gene on the pairwise correlation coefficients of the 22 matched tumor pairs less the mean effect of the gene on the remaining 210 tumor-tumor pairwise correlation coefficients. The "effect" of a gene on a pairwise correlation was defined as the difference in the correlation coefficient with and without data for the gene included. Higher "within-between" scores indicated that the gene had a good tendency to group together paired samples.

The 496 genes with a score one standard deviation above the mean score were selected and defined as the "intrinsic" gene subset. To confirm the existence of an "intrinsic" set of genes and to verify that the "within-between" score identified these genes, the predictive quality of the score was examined using a type of "leave-one-out" cross-validation analysis. The entire analysis was repeated 22 times, each with one of the 22 matched pairs completely removed from the analysis. If an "intrinsic" set of genes existed, and if the "within-between" score successfully identified these genes, it was expected that the genes with high scores in each reduced dataset would produce relatively high correlations in the excluded pair. When the genes were sorted based on their "within-between" score in each reduced dataset, the correlation coefficient of the excluded matched pair in sliding windows of 250 genes increased progressively with increasing "within-between" score for nearly all of the matched pairs, while no such increase was found when randomly matched pairs were used.

The clustering method was used as described above to cluster the experimental samples based on the gene expression patterns of the 496 genes included in the "intrinsic" gene subset.

(ii) Selection of an "Epithelial-enriched" Gene Subset

A second optimized gene subset (called the "epithelial-enriched" gene subset) was selected consisting of 374 genes that Applicants considered likely to be expressed primarily by normal or malignant breast epithelial cells. The rationale for this gene subset is that each of the tumors was ultimately caused by alterations in breast epithelial cells. The seven individual subsets of genes that were chosen to form the "epithelial-enriched" gene subset were selected from the 1753 gene cluster diagram presented in Appendix B. The actual groups of genes chosen are listed in Table 7. These seven subsets of genes included:

1) A subset that was very highly expressed in the cultured basal cell lines, along with some of the other breast derived cell lines including Hs578T and BT-549;
2) A subset that was expressed in all of the cultured epithelial cell lines (both basal and luminal);
3) A subset of genes centered around the high level of expression of Erb-B2;
4) A subset of genes that contained genes known to be important for tumor biology (e.g., the urokinase receptor);
5) A subset that contained genes that were most highly expressed in the basal-like tumors;
6) A subset of genes highly expressed in some of the luminal-like tumors;
7) A subset of genes that was primarily expressed in the four breast carcinoma derived cell lines and/or in many of the luminal-like tumors.

The clustering method was used as described above to cluster the experimental samples based on the gene expression patterns of the 374 genes included in the "epithelial-enriched" gene set.

To confirm the results of the clustering analysis described below, a "weighted voting" method was applied to the data as described in Golub, T. R., et al., *Science*, 286, 531–537, 1999.

Results

The 496 genes included in the "intrinsic" gene set are identified in Table 6, and Appendix D shows the complete 496 gene cluster diagram formed using the "intrinsic" gene set. Appendix C presents details of the results of cluster analysis using the "intrinsic" gene set. Two large branches were apparent in the tumor dendrogram, and within each of these two branches, smaller branches were identified for which common biological themes could be inferred. The branches are colored accordingly (basal-like=ORANGE, Erb-B2 positive=PINK, normal breast-like=GREEN, and luminal epithelial-like=BLUE). Appendix C, part a shows the cluster dendrogram obtained by hierarchical clustering of the experimental samples based on similarities in expression of the intrinsic gene set. As is evident from this dendrogram, 17 of the 20 before and after doxorubicin pairs (indicated with suffixes BE and AF following the numerical identifier for each tumor) were matched together on terminal dendrogram branches (red branches), as were both of the tumor/lymph node metastasis pairs (blue branches). The small black bars beneath the dendrogram identify the 17 pairs that were correctly matched by this hierarchical clustering, while the larger green bars identify the positions of the three pairs that were not matched by the clustering. It is noted that the after-chemotherapy sample in each of these three sample pairs was clustered in a branch with normal breast tissue samples. Thus as for the 1753 gene set described in Examples 6 and 7, the intrinsic gene subset correctly identified independent tumor samples from the same tumor as related to each other. Despite the potential confounding effects of an interval of 16 weeks, independent surgical procedures and cytotoxic chemotherapy, the independent samples taken from the same tumor were in most cases recognizably more similar to each other in their overall pattern of gene expression than either was to any of the other samples. In addition, samples taken from a primary tumor and a metastasis from the same tumor could be recognized as closely related to one another. Thus in most cases independent samples from the same tumor were recognizable as such solely on the basis of gene expression patterns. This implies that the patterns of gene expression are homogeneous and stable in each breast tumor and yet sufficiently diverse between tumors so that they can be viewed as molecular portraits of each tumor.

Appendix C, part b shows a scaled-down representation of the entire "intrinsic" cluster diagram (the complete "intrinsic" cluster diagram, with all gene names is presented in Appendix E). Appendix C, part c shows the luminal epithelial cell gene subset, including the estrogen receptor. Appendix C, part d shows the Erb-B2 overexpression subset. Appendix C, part e shows the basal epithelial cell-associated gene subset, including keratins 5 and 17, while Appendix C, part f shows a second basal epithelial cell-associated gene subset. Appendix C, part g shows the lymphocyte/B-cell-associated gene subset. The 374 genes included in the "epithelial-enriched" subset are listed in Table 8, and the complete 374 gene cluster diagram formed when using the "epithelial-enriched" gene set is shown in Appendix F.

FIG. 2 presents a comparison of tumor dendrograms representing the results of hierarchical clustering of experimental samples using the "intrinsic" gene set (Appendix E) and the dendrogram obtained by clustering using the "epithelial-enriched" gene set (Appendix F). The dendrograms are colored according to the clustering patterns obtained using the "intrinsic" gene set. Only two tumors (identified by the colored arrows) were placed in significantly different groups when the clustering was based on expression of the "epithelial-enriched" gene set instead of the "intrinsic" gene set.

The overall architecture of the two dendrograms representing the clustering of breast tumor samples using these two alternative gene sets was very similar, with only two tumor pairs (i.e. Norway 14 and 26) materially changing position (FIG. 2). Thus, the classifications derived from the "intrinsic" gene set are consistent with the results using the "epithelial-enriched" gene set, even though the two sets shared only 25% of their genes.

A consistent division of the tumor samples into two subgroups was a striking feature of the dendrograms produced by both gene sets. Application of the "weighted voting" method of Golub recapitulated the sorting of the tissue samples between these two subgroups for all but one of the 65 samples, thus confirming the robustness of the division.

Example 9

Identification of Breast Tumor Subgroups Based on Optimized Gene Sets

Several groups of tumors that shared pervasive similarities in their expression patterns could be identified by cluster analysis; the dendrograms in FIG. 2 and Appendices A, C, and D are color-coded to highlight these subgroups. Characteristic features of the expression patterns, or the membership, of each highlighted group also suggested biological interpretations. These data confirm the ability of the clustering method to divide breast tumors into meaningful subgroups when applied using the "intrinsic" and "epithelial-enriched" gene subsets. Specific subgroups are discussed below and are named according to correlations between the genes expressed at high levels in the tumors and genes known to be expressed in particular cell types.

Luminal Epithelial Cell Pattern: As described above, the major distinction was between a large group of tumors (identified by blue letters and dendrogram branches) and a second large group that included all of the other tumor subtypes and the normal breast samples (highlighted in other colors). The tumors in this "blue" group were characterized by relatively high levels of expression of many genes known to be expressed by the luminal epithelial cells of the normal mammary duct, notably including the estrogen and prolactin receptors (Appendix C, part c). This connection was further corroborated using immunohistochemical analysis of breast tumor sections using antibodies against the luminal cell keratins 8/18, which stained the carcinoma cells in tumor specimens in this "blue" branch as shown, for example, in FIG. 3f. With one exception, none of the tumors in this group expressed Erb-B2 at high levels (Appendix C, part d). An estrogen receptor-positive phenotype is known to be associated with a relatively favorable prognosis[30,31], while Erb-B2 expression is believed to contribute to tumorogenesis.

Normal Breast Tissue Pattern: Several tumors, including two "before and after" pairs and the single fibroadenoma tested (displayed in green), were clustered in a group of samples that contained all three of the normal breast specimens (Appendices C and E). The "normal breast" gene expression pattern was typified by a relatively high level of expression of genes characteristic of basal epithelial cells and adipose cells, and relatively low levels of expression of genes characteristic of luminal epithelial cells.

Basal Epithelial Cell Pattern: Many of the genes characteristic of basal epithelial cells were highly expressed in a group of six tumors (New York 2 and 3, Stanford 14 and 23, and Norway 41 and 109, indicated in orange in the dendrogram in Appendix C, part a), that were clustered based on pervasive similarities in their gene expression patterns (Appendices C and E). To corroborate the "basal cell-like" characteristics of these tumors, immunohistochemistry was performed using antibodies against keratins 5/6, 8/18, and 17. All six of these tumors showed staining for either keratins 5/6 and/or 17 (basal cell keratins), and no staining for keratins 8/18 (See FIG. 3e.) Notably, these six tumors also failed to express the estrogen receptor and most of the other genes that were usually co-expressed with it (Appendix C, part c). Approximately 90% of breast tumors are suggested to have characteristics of luminal epithelial cells, while the characteristics of the remaining 10% are less well defined[18]. Breast tumors that stain positive for basal cell keratins may account for 3–15% of all breast tumors[41-46]. The incidence among the tumor samples described herein was 15% (6/40). Many of the tumors that stained positive for basal cell keratins only showed staining in a fraction of the tumor cells, and neither basal nor luminal keratins could be detected in any of the other remaining tumor cells (FIG. 3e).

Erb-B2 Positive: As mentioned above, overexpression of the Erb-B2 oncogene was associated with a high level of expression of a specific set of genes, almost all of which map to the Erb-B2 region of chromosome 17[33]. A clustered group of tumors was identified that was partially characterized by the high level of expression of this subset of genes (Appendix C, part d: Stanford 2 and Norway 47, 53, 57 and 101, indicated in pink on the dendrogram in Appendix C, part a). These tumors showed low levels of expression of the estrogen receptor[48,49] and almost all of the other genes associated with estrogen receptor expression (Appendix C, part c), a trait they share with the "basal-like" tumors, and which may contribute to the poor prognosis associated with these two subtypes of breast tumors[41,43,49,50]; in addition, both the basal-like and ErbB2 positive tumors also show many p53 sequence mutations (see Table 5).

Example 10

Producing Antibodies to Basal Marker Polypeptides and Cytokeratin 17

This example describes the generation of polyclonal antibodies that bind to cytokeratin 17 and the generation of polyclonal antibodies that bind to the polypeptides encoded by the three basal marker genes described herein, i.e., cadherin3, matrix metalloproteinase 14, and cadherin EGF LAG seven-pass G-type receptor 2. The example further describes affinity purification of the antibodies.

Materials

Anisole (Cat. No. A4405, Sigma)
2,2'-azino-di-(3-ethyl-benzthiazoline-sulfonic acid) (ABTS) (Cat. No. A6499, Molecular Probes Eugene, Oreg.)
Activated Maleimide Keyhole Limpet Cyanin (Cat. No. 77106, Pierce Chemical Co. Rockford, Ill.)
Biotin (Cat. No. B2643, Sigma)
Boric acid (Cat. No. B0252, Sigma)
Sepharose 4b (Cat. No. 17-0120-01, LKB/Pharmacia, Uppsala, Sweden)
Bovine Serum Albumin (LP) (Cat. No. 100 350, Boehringer Mannheim, Indianapolis, Ind.)
Cyanogen bromide (Cat. No. C6388 Sigma, St. Louis, Mo.)
Dialysis tubing Spectra/Por Membrane MWCO: 6-8,000 (Cat. No. 132 665, Spectrum Industries Inc., Laguna Hills, Calif.)
Dimethyl formamide (DMF) (Cat. No. 22705-6, Aldrich Chemical Company, Milwaukee, Wis.)
DIC (Cat. No. BP 592-500, Fisher)
Ethanedithiol (Cat. No. 39,802-0, Aldrich Chemicals, Milwaukee, Wis.)
Ether (Cat. No. TX 1275-3, EM Sciences)
Ethylenediaminetetraacetatic acid (EDTA) (Cat No. BP 120-1, Fisher Scientific, Springfield, N.J.)
1-ethyl-3-(3'dimethylaminopropyl)-carbodiimide, HCL (EDC) (Cat No. 341-006, Calbiochem, San Diego, Calif.)
Freund's Adjuvant, complete (Cat. No. M-0638-50B, Lee Laboratories, Grayson, Ga.)
Freund's Adjuvant, incomplete (Cat. No. M0639-50B, Lee Laboratories)
Fritted chromatography columns (Column part No. 12131011; Frit: Part No. 12131029, Varian Sample Preparation Products, Harbor City, Calif.)
Gelatin from Bovine Skin (Cat. No. G9382, Sigma)
Glycine (Cat. No. BP381-5, Fisher)
Goat anti-rabbit IgG, biotinylated (Cat No. A 0418, Sigma)
HOBt (Cat. No. 01-62-0008, Calbiochem-Novabiochem)
Horseradish peroxidase (HRP) (Cat. No. 814 393, Boehringer Mannheim)
HRP-Streptavidin (Cat. No. S 5512, Sigma)
Hydrochloric Acid (Cat No. 71445-500, Fisher)
Hydrogen Peroxide 30% w/w (Cat. No. H1009, Sigma)
Methanol (Cat. No. A412-20, Fisher)
Microtiter plates, 96 well (Cat. No. 2595, Corning-Costar Pleasanton, Calif.)
N-•-Fmoc protected amino acids available from Calbiochem-Novabiochem, San Diego, Calif. See 1997–1998 catalog pages 1–45.
N-•-Fmoc protected amino acids attached to Wang Resin available from Calbiochem-Novabiochem. See 1997–1998 catalog pages 161–164.
NMP (Cat. No. CAS 872-50-4, Burdick and Jackson, Muskegon, Mich.)
Peptide (Synthesized by Research Genetics, Inc. Details given below)
Piperidine (Cat. No. 80640, Fluka, available through Sigma)
Sodium Bicarbonate (Cat. No. BP328-1, Fisher)
Sodium Borate (Cat. No. B9876, Sigma)
Sodium Carbonate (Cat. No. BP357-1, Fisher)
Sodium Chloride (Cat. No. BP 358-10, Fisher)
Sodium Hydroxide (Cat. No. SS 255-1, Fisher)
Streptavidin (Cat. No. 1 520, Boehringer Mannheim)
Thioanisole (Cat. No. T-2765, Sigma)
Trifluoroacetic acid (Cat. No. TX 1275-3, EM Sciences)
Tween-20 (Cat. No. BP 337-500, Fisher)
Wetbox—(Rubbermaid Rectangular Servin' Saver™ Part No. 3862 Wooster, Ohio)

Solutions

BBS—Borate Buffered Saline with EDTA dissolved in distilled water (pH 8.2 to 8.4 with HCl or NaOH)
  25 mM Sodium borate (Borax)
  100 mM Boric Acid
  75 mM NaCl
  5 mM EDTA
0.1 N HCl in saline
  concentrated HCl (8.3 mL/0.917 L distilled water)
  0.154 M NaCl
Glycine (pH 2.0 and pH 3.0) dissolved in distilled water and adjusted to the desired pH.
  0.1 M glycine
  0.154 M NaCl
5×Borate 1X Sodium Chloride dissolved in distilled water.
  0.11 M NaCl
  60 mM Sodium Borate
  250 mM Boric Acid
Substrate Buffer in distilled water adjusted to pH 4.0 with sodium hydroxide:
  50 to 100 mM Citric Acid
Peptide Synthesis Solutions
AA solution: HOBt is dissolved in NMP (8.8 grams HOBt to 1 liter NMP). Fmoc-N-a-amino at a concentration at 0.53 M.
DIC solution: 1 part DIC to 3 parts NMP.
Deprotecting solution: 1 part Piperidine to 3 parts DMF
Reagent R: 2 parts anisole, 3 parts ethanedithiol, 5 parts thioanisole, 90 parts trifluoroacetic acid.

Equipment

MRX Plate Reader (Dynatech Inc., Chantilly, Va.)
Hamilton Eclipse (Hamilton Instruments, Reno, Nev.)
Beckman TJ-6 Centrifuge, Refrigerated (Model No. TJ-6, Beckman Instruments, Fullerton, Calif.)
Chart Recorder (Recorder 1 Part No. 18-1001-40, Pharmacia LKB Biotechnology)
UV Monitor (Uvicord SII Part No. 18-1004-50, Pharmacia LKB Biotechnology)
Amicon Stirred Cell Concentrator (Model 8400, Amicon Inc., Beverly, Mass.)
30 kD MW cut-off filter (Cat. No. YM-30 Membranes Cat. No. 13742, Amicon Inc., Beverly, Mass.)
Multi-channel Automated Pipettor (Cat. No. 4880, Corning Costar Inc., Cambridge, Mass.)
pH Meter Corning 240 (Corning Science Products, Corning Glassworks, Corning, N.Y.)

ACT396 peptide synthesizer (Advanced ChemTech, Louisville, Ky.)
Vacuum dryer (Box is from Labconco, Kansas City, Mo.; Pump is from Alcatel, Laurel Md.).
Lyophilizer (Unitop 600sl in tandem with Freezemobile 12, both from Virtis, Gardiner, N.Y.)

Methods

Peptides were selected using the program Omiga™1.1 (Oxford Molecular Group, Inc., 2105 So. Bascom Ave., Suite 200, Campbell, Calif. 95008) using the Hopp/Woods method, which is described in Hopp T P, Woods K R, *Mol Immunol,* April; 20 (4):483–9 A computer program for predicting protein antigenic determinants, 1983, and Hopp T P and Woods K R, *Proc. Nat. Acad. Sci.* U.S.A. 78, 3824–3828, 1981. Preferred peptide sequences displayed minimal homology with known proteins. Three peptide sequences were selected for each polypeptide. The sequences were as follows:

Peptides for antibodies that bind to cadherin3 (GenBank accession number NP_001784):

| | |
|---|---|
| RAVFREAEVTLEAGGAEQE | (SEQ ID NO:4) |
| QEPALFSTDNDDFTVRN | (SEQ ID NO:5) |
| QKYEAHVPENAVGHE | (SEQ ID NO:6) |

Peptides for antibodies that bind to matrix metalloproteinase 14 (GenBank accession number NP_004986):

| | |
|---|---|
| AYIREGHEKQADIMIFFAE | (SEQ ID NO:7) |
| DEASLEPGYPKHIKELGR | (SEQ ID NO:8) |
| RGSFMGSDEVFTYFYK | (SEQ ID NO:9) |

Peptides for antibodies that bind to anti-cadherin EGF LAG seven-pass G-type receptor 2 (GenBank accession number NP_001399):

| | |
|---|---|
| QASSLRLEPGRANDGDWH | (SEQ ID NO:10) |
| ELKGFAERLQRNESGLDSGR | (SEQ ID NO:11) |
| RSGKSQPSYIPFLLREE | (SEQ ID NO:12) |

Peptides for antibodies that bind to anti-cytokeratin 17:

| | |
|---|---|
| KKEPVTTRQVRTIVEE | (SEQ ID NO:13) |
| QDGKVISSREQVHQTTR | (SEQ ID NO:14) |
| SSSIKGSSGLGGGSS | (SEQ ID NO:15) |

Synthesis of Peptides
Incubate: Resin was immersed in appropriate solution. All incubation steps occured with mixing.
Wash: Added 2 mls. DMF, incubated 5 minutes and drained.
Wash Cycle: Five washes.
Machine Synthesis
The sequence of the desired peptide was provided to the peptide synthesizer. The C-terminal residue was determined and the appropriate Wang Resin was attached to the reaction vessel. The peptides were synthesized C-terminus to N-terminus by adding one amino acid at a time using a synthesis cycle. Which amino acid is added was controlled by the peptide synthesizer, which looks to sequence of the peptide entered into its database.

Step 1—Resin Swelling: Added 2 mL DMF, incubated 30 minutes, drained DMF.
Step 2—Synthesis cycle
  2a—Deprotection: 1 mL deprotecting solution was added to the reaction vessel and incubated for 20 minutes.
  2b—Wash Cycle
  2c—Coupling: 750 mL of amino acid solution and 250 mL of DIC solution were added to the reaction vessel. The reaction vessel was incubated for thirty minutes and washed once. The coupling step was repeated once.
  2d—Wash Cycle
Step 2 was repeated over the length of the peptide. The amino acid solution changed as the sequence listed in peptide synthesizer dictated.
Step 3—Final Deprotection: Steps 2a and 2b were performed one last time.

Resins were deswelled in methanol—rinsed twice in 5 mL methanol, incubated 5 minutes in 5 mL methanol, rinsed in 5 mL methanol—and then vacuum dried.

Peptide was removed from the resin by incubating 2 hours in reagent R and then precipitated into ether. Peptide was washed in ether and then vacuum dried. Peptide was resolubilized in diH20, frozen, and lyophilized overnight.

Conjugation of Peptide with Keyhole Limpet Hemocyanin
Peptide (6 mg) was dissolved in PBS (6 mL) and mixed with 6 mg of maleiimide activated KLH carrier in 6 mL of PBS for a total volume of 12 mL. The entire solution was mixed for two hours, dialyzed in 1L PBS, and lyophilized.

Immunization of Rabbits
Two New Zealand White Rabbits were injected with 250 µg keyhole limpet hemocyanin (KLH) conjugated peptide in an equal volume of complete Freund's adjuvant and saline in a total volume of 1 mL. Antigens (KLH-Peptide, 100 µg each) in an equal volume of incomplete Freund's Adjuvant and saline were injected into three to four subcutaneous dorsal sites for a total volume of 1 mL two, four, and six weeks after the first immunization. The three peptides were injected together.

The immunization schedule was as follows:

| | |
|---|---|
| Day 0 | Pre-immune bleed, primary immunization |
| Day 15 | 1st Boost |
| Day 27 | 1st Bleed |
| Day 44 | 2nd Boost |
| Day 57 | 2nd Bleed and 3rd Boost |
| Day 69 | 3rd Bleed |
| Day 84 | 4th boost |
| Day 98 | 4th bleed |

The Collection of Rabbit Serum
The rabbits were bled (30 to 50 mL) from the auricular artery. The blood was allowed to clot at room temperature for 15 minutes and the serum was separated from the clot using an IEC DPR-6000 centrifuge at 5000×g. Cell-free serum was decanted gently into a clean test tube and stored at −20° C. for affinity purification.

Determination of Antibody Titer
All solutions with the exception of wash solution were added by the Hamilton Eclipse, a liquid handling dispenser. The antibody titer was determined in the rabbits using an ELISA assay with peptide on the solid phase. Flexible high binding ELISA plates were passively coated with peptide diluted in BBS (100 µL, 1 µg/well) and the plate was incubated at 4° C. in a wetbox overnight (air-tight container with moistened cotton balls). The plates were emptied and then washed three times with BBS containing 0.1% Tween-20 (BBS-TW) by repeated filling and emptying using a semi-automated plate washer. The plates were blocked by completely filling each well with BBS-TW containing 1% BSA and 0.1% gelatin (BBS-TW-BG) and incubating for 2 hours at room temperature. The plates were emptied and sera of both pre- and post-immune serum were added to wells. The first well contained sera at 1:50 in BBS. The sera were then serially titrated eleven more times across the plate at a ratio of 1:1 for a final (twelfth) dilution of 1:204,800. The plates were incubated overnight at 4° C. The plates were emptied and washed three times as described.

Biotinylated goat anti-rabbit IgG (100 µL) was added to each microtiter plate test well and incubated for four hours at room temperature. The plates were emptied and washed three times. Horseradish peroxidase-conjugated Streptavidin (100 µL diluted 1:10,000 in BBS-TW-BG) was added to each well and incubated for two hours at room temperature. The plates were emptied and washed three times. The ABTS was prepared fresh from stock by combining 10 mL of citrate buffer (0.1 M at pH 4.0), 0.2 mL of the stock solution (15 mg/mL in water) and 10 µL of 30% $H_2O_2$. The ABTS solution (100 µL) was added to each well and incubated at room temperature. The plates were read at 414λ, 20 minutes following the addition of substrate.

Preparation of the Peptide Affinity Purification Column

The affinity column was prepared by conjugating 5 mg of peptide to 10 mL of cyanogen bromide-activated Sepharose 4B, and 5 mg of peptide to hydrazine-Sepharose 4B. Briefly, 100 uL of DMF was added to peptide (5 mg) and the mixture was vortexed until the contents were completely wetted. Water was then added (900 µL) and the contents were vortexed until the peptide dissolved. Half of the dissolved peptide (500 µL) was added to separate tubes containing 10 mL of cyanogen-bromide activated sepharose 4B in 0.1 mL of borate buffered saline at pH 8.4 (BBS), and 10 mL of hydrazine-Sepharose 4B in 0.1 M carbonate buffer adjusted to pH 4.5 using excess EDC in citrate buffer pH 6.0. The conjugation reactions were allowed to proceed overnight at room temperature. The conjugated sepharose was pooled and loaded onto fritted columns, washed with 10 mL of BBS, blocked with 10 mL of 1 M glycine, and washed with 10 mL 0.1 M glycine adjusted to pH 2.5 with HCl and re-neutralized in BBS. The column was washed with enough volume for the optical density at 280λ to reach baseline.

The Affinity Purification of Antibodies

The peptide affinity column was attached to a UV monitor and chart recorder.

The titered rabbit antiserum was thawed and pooled. The serum was diluted with one volume of BBS and allowed to flow through the columns at 10 mL per minute. The non-peptide immunoglobulins and other proteins were washed from the column with excess BBS until the optical density at 280 λ reached baseline. The columns were disconnected and the affinity purified column was eluted using a stepwise pH gradient from pH 7.0 to pH 1.0. The elution was monitored at 280 nM, and fractions containing antibody (pH 3.0 to pH 1.0) were collected directly into excess 0.5 M BBS. Excess buffer (0.5 M BBS) in the collection tubes served to neutralize the antibodies collected in the acidic fractions of the pH gradient.

The entire procedure was repeated with "depleted" serum to ensure maximal recovery of antibodies. The eluted material was concentrated using a stirred cell apparatus and a membrane with a molecular weight cutoff of 30 kD. The concentration of the final preparation was determined using an optical density reading at 280 nM. The concentration was determined using the following formula: mg/mL=$OD_{280}$/1.4.

Example 11

SDS-PAGE and Immunoblot Analysis of Basal Marker Polypeptides

To investigate the expression pattern of cadherin3, matrix metalloproteinase 14, and cadherin EGF LAG seven-pass G-type receptor 2, extracts were made from a variety of different cell lines and subjected to SDS-PAGE followed by immunoblotting according to the protocol below, using affinity purified polyclonal antibody to BSTP-ECG1 prepared as described in Example 10.

Materials

Acetic acid, Glacial (Cat. No. A38$^c$-212, Fisher)
Acrylamide (Cat. No. A-3553, Sigma)
Anti-Rabbit IgG (H&L) (Cat. No. 31460ZZ, Pierce)
Bis-acrylamide (Cat. No. M-7279, Sigma)
Blotting paper (Cat. No. 170-3960, Bio-Rad, Hercules, Calif.)
Bovine Serum Albumin (LP) (Cat. No. 100-350, Boehringer Mannheim, Indianapolis, Ind.)
Brilliant Blue R-250 (Cat. No. BP101-25, Fisher)
Complete™ Mini (Cat. No. 1836153, Boehringer Mannheim)
ECL Western Blotting Detection Reagents (Cat. No. RPN2106, Amersham Pharmacia Biotech, Piscataway, N.J.)
Ethyl alcohol (AAPER Alcohol and Paper Chemical Co., Shelbyville, Ky.)
Gelplate Clean (Cat. No. 786-140RF, Geno Technology, Inc., St. Louis)
Gelatin (Cat. No. G-2500, Sigma)
Glycerol (Cat. No. BP229-1, Fisher)
Glycine (Cat. No. G-8898, Sigma)
Hybond ECL (Cat. No. RPN303D, Amersham Pharmacia Biotech)
Lauryl Sulfate (SDS) (Cat. No. L-3771, Sigma)
Methanol (Cat. No. BP1105-4, Fisher)
M-Per (Cat. No. 78501, Pierce, Rockford, Ill.)
Nalgene bottle top filters (Cat. No. 09-740-62B, Fisher)
Nonfat dry milk (Kroger Co., Cincinnati, Ohio)
Ponceau-S (Cat. No. P-07170, Sigma)
Potassium phosphate (Cat. No. P-0662, Sigma)
2X SDS gel loading buffer (Cat. No. 750006, Research Genetics, Huntsville, Ala.)
Size markers (Cat. No. M-3913, M-4038, M-3788, Sigma)
Sodium azide (Cat. No. S227I-25, Fish)
Sodium chloride (Cat. No. S271-3, Fisher)
Sodium phosphate, Dibasic, Anhydrous (Cat. No. BP332-1, Fisher)
t-amyl alcohol (Cat. No. A-16852, Sigma)
TEMED (Cat. No. T-9281, Sigma)
Trizma® Base (Cat. No. T-6066, Sigma)
Tween-20 (Cat. No. BP337-500, Fisher)

Solutions

PBS—Phosphate Buffered Saline dissolved in distilled water
  136 mM NaCl
  2.7 mM KCl
  10.1 mM $Na_2HPO_4$
  1.8 mM $KH_2PO_4$
Acrylamide/Bis (30% T, 2.67% C) dissolved in distilled water
  4.1 M acrylamide
  51.9 mM N,N'-
1.5 M Tris-HCl (pH 8.8) dissolved in distilled water
0.5 M Tris-HCl (pH 6.8) dissolved in distilled water 10% SDS—dissolve 10 grams SDS in 100 mls distilled water Running Buffer
- 24.8 mM Tris base
- 191.9 mM glycine
- 3.5 mM SDS Towbin transfer buffer (pH 8.3) dissolved in distilled water
- 20% methanol
- 25 mM Tris
- 192 mM glycine Equilibrating buffer for gel drying, mixed in distilled water
- 20% ethanol
- 10% glycerol Gel staining solution dissolved in distilled water
- 0.3 mM Coomassie brilliant blue R-250
- 40% methanol
- 7% glacial acetic acid Gel destaining solution mixed in distilled water
- 25% methanol
- 7% glacial acetic acid 10% Tween®20 in PBS 5% Nonfat dry milk in PBS 0.2% BSA Blocking Buffer dissolved in PBS
- 0.2% BSA
- 0.1 % gelatin
- 0.05% Tween®20

Wash Buffer
- 0.05% Tween®20
- 1X PBS

Equipment

Microcentrifuge (Model 5415, Eppendorf)
Power Pak 200 (Cat. No. 165-5052, Bio-Rad)
Power Pak 3000 (Cat. No. 165-5056, Bio-Rad)
Protean II xi Cell (Cat. No. 165-1813, Bio-Rad)
Recirculating chiller (Cat. No. CFT33D115V, Neslab Instruments, Inc., Portsmouth, N.H.)
20-Well comb (Cat. No. 165-1867, Bio-Rad)
pH Meter Corning 240 (Corning Science Products, Corning Glasswares, Corning, N.Y.)
Air Cadet vacuum pump (Cat. No. P-07530-50, Cole-Palmer Instruments Co., Chicago, Ill.)
Tissue Tearor tissue homogenizer (Cat. No. 985370-07, BioSpec Products Inc., Bartletsville, Okla.)

Methods

Sample Preparation

The following cell lines were used: 184B5, MCF7, OVCAR3, UACC62, HepG2, Colo205, UACC62, JURKAT, N-TERA2, MOLT4, Sw872. These cell lines are well known in the art. Descriptions of these cell lines are provided in Table 3, in Perou, et al., Molecular portraits of human breast tumours, *Nature*, 406(6797):747–52, 2000, in Ross, D. T. et al. Systematic Variation in Gene Expression Patterns in Human Cancer Cell Lines. Nature Genetics, 24(3):227–35, 2000, and at the American Type Culture Collection Web site: www.atcc.org. Cell lines were maintained under standard growth conditions and in standard tissue culture media as appropriate for the particular cell line. Cells were collected according to standard techniques (e.g., trypsinization in the case of adherent cells), and the resulting cell suspension was prepared as follows:

The cell suspension was pelleted by centrifugation at 3000 RPM for 10 minutes, and the supernatant was discarded.

The pellet was washed with 1 ml PBS, centrifuged at 10000 RPM for 10 minutes, and the supernatant was discarded.

An appropriate volume of M-Per™ Reagent was added to the cell pellet and mixed gently for 10 minutes in an ice bath. The mixture was centrifuged at 13200 RPM for 15 minutes, and the supernatant was saved.

The protein concentration in the supernatant was measured according to standard techniques. All samples were mixed at 1:1 with gel loading buffer and boiled for 5 minutes before loading.

SDS PAGE

Standard SDS-PAGE stacking and running gels were prepared and placed in an electrophoresis apparatus. After filling the upper and lower chambers with running buffers the samples (60· g/lane) were loaded. The inner core was placed in the lower chamber and the lid placed on top. The apparatus was connected to the power supply and recirculating system. The temperature setting was 10·C. The stacking gel was run at 14 mA per gel for 1 hour. The separating gel was run at 0.58 mA per gel per hour for 16 hours.

Transfer to nitrocellulose

After electrophoresis was complete, the gel was equilibrated in Towbin Buffer for 15–30 minutes. The assembly for transfer was as follows:
- cathode
- pre-soaked blotting paper
- gel
- pre-wetted nitrocellulose
- pre-soaked blotting paper
- anode The transfer was performed at 20V for 25 minutes, then 25V for 20 minutes. After the transfer was complete, the gel was stained with Coomassie and the blot was stained with Ponceau-S.

Western Blotting

Primary and Secondary Antibodies

All primary and secondary antibodies were diluted in 0.2% BSA blocking buffer. All incubation steps were done with gentle mixing.

Blots were blocked in 5% milk overnight at room temperature. The blots were rinsed with wash buffer before adding the primary antibody and incubating for two hours at room temperature.

The primary antibodies were used at titers of 1:200, 1:500, and 1:1000 for anti-matrix metalloproteinase 14 and anti-cadherin EGF LAG seven-pass G-type receptor 2 and at 1:100 for anti-cadherin3.

One wash cycle was performed. One wash cycle consisted of:
- Wash 5 min, rinse
- Wash 5 min, rinse
- Wash 10 min, rinse
- Wash 5 min, rinse
- Wash 5 min, rinse The secondary antibody was added and incubated for one hour at room temperature. One wash cycle was then performed.

Peptide Block

As a control to demonstrate the specificity of the antibody, in some experiments equal amounts (w/w) of peptide and antibody were added to ⅒ of the final volume of blocking buffer and incubated overnight at 4° C. The volume of blocking buffer was then brought up to the final volume, and the membrane was incubated for an additional two hours at room temperature.

Developing

The blots were placed in a Ziploc® bag. Equal volumes of ECL western blotting detection reagents were mixed and distributed evenly over the blots. The blots were placed in an autoradiography cassette, covered with a piece of film, and exposed.

Results

Figure 4A:
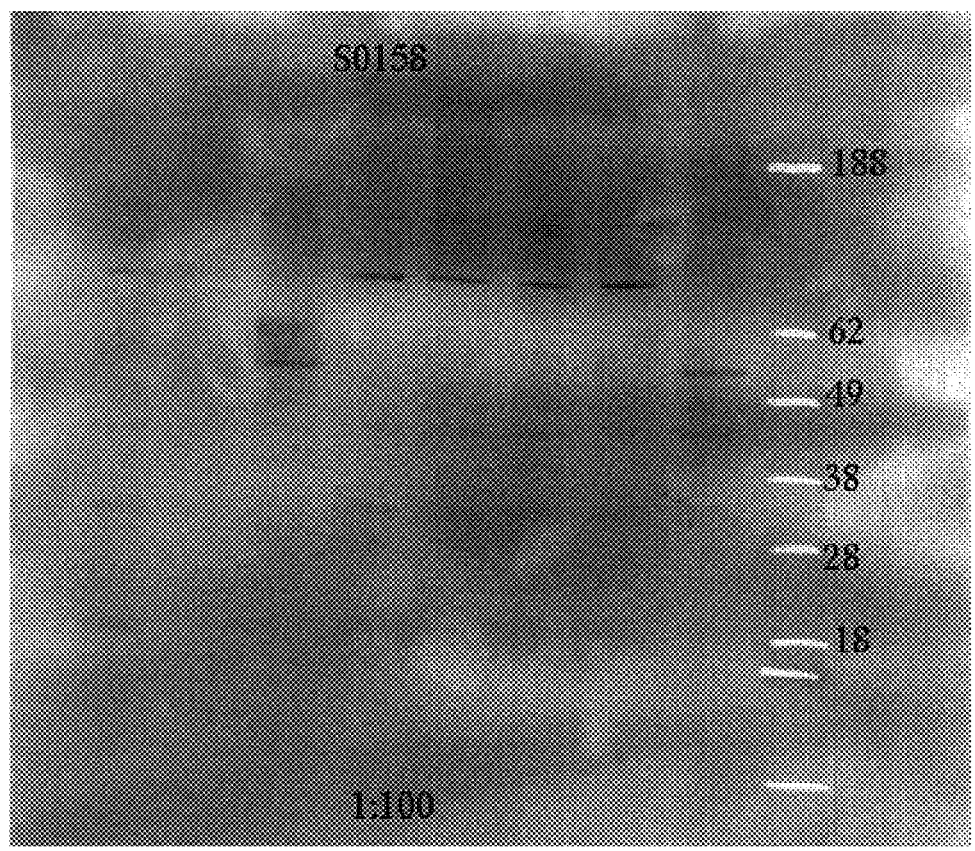
FIG. 4A shows a Western blot demonstrating expression of the cadherin3 polypeptide in various cell lines.

FIG. 4A shows a Western blot demonstrating expression of the cadherin3 polypeptide in various cell lines. The lane order is, from left to right: MCF-7, Colo205, UACC62, JURKAT, HEPG2, N-TERA2, MOLT4, Sw872. The primary antibody was used at a dilution of 1:100.

Figure 4B:
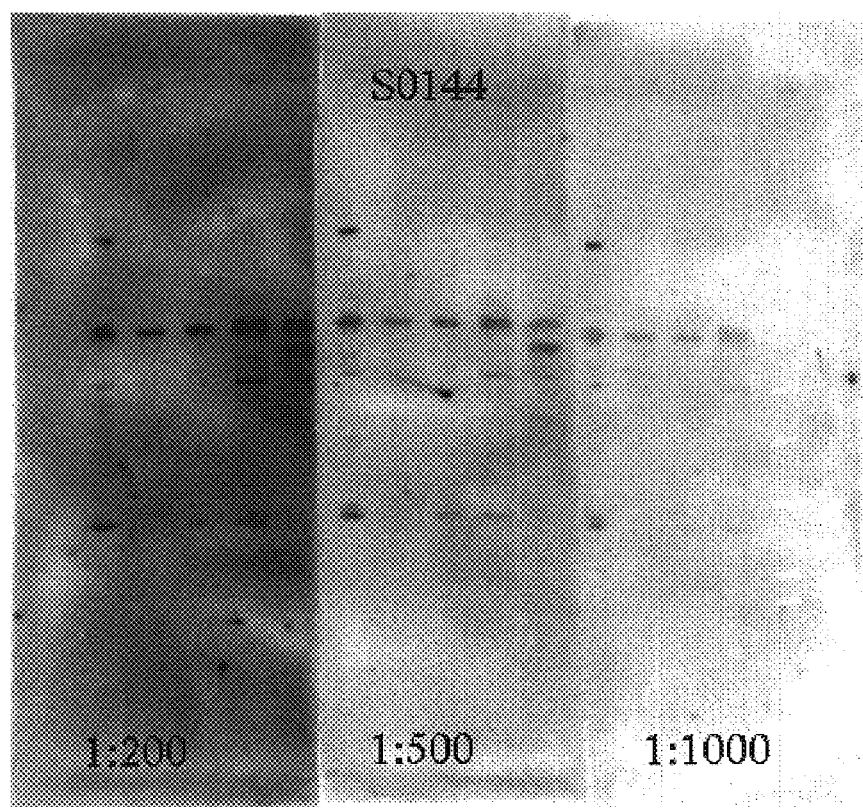
FIG. 4B shows a Western blot demonstrating expression of the matrix metalloproteinase 14 polypeptide in various cell lines.

FIG. 4B shows a Western blot demonstrating expression of the matrix metalloproteinase 14 polypeptide in various cell lines. The lane order is, from left to right: 184B5, MCF7, OVCAR3, UACC62, HepG2. The three images present identical blots in which the primary antibody was used at dilutions of 1:200 (left), 1:500 (middle), and 1:1000 (right).

Figure 4C:
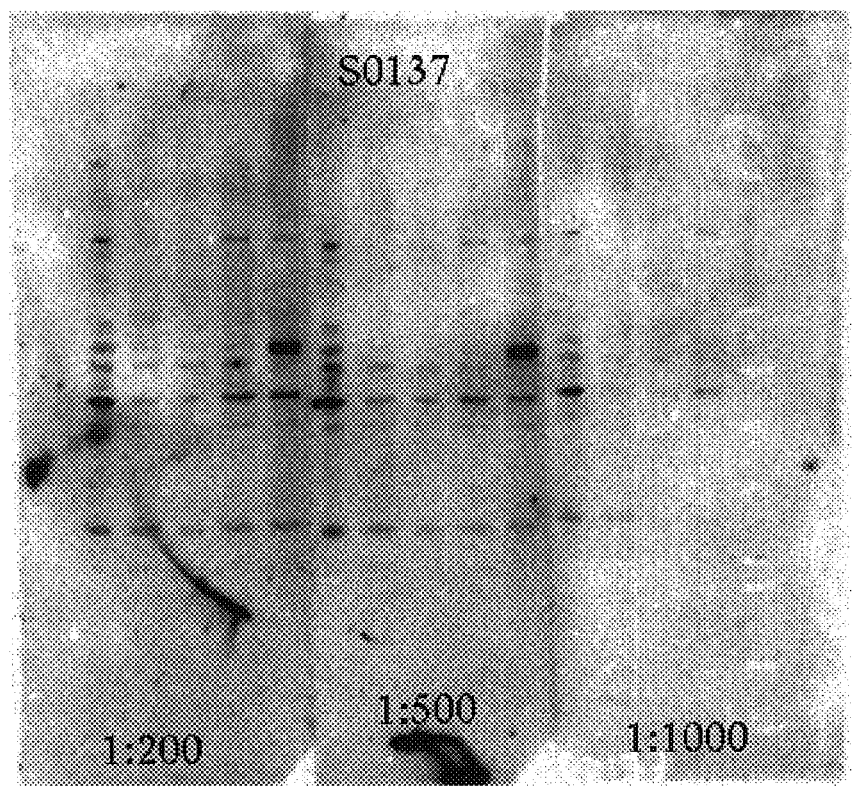
FIG. 4C shows a Western blot demonstrating expression of the cadherin EGF LAG seven-pass G-type receptor 2 polypeptide in various cell lines.

FIG. 4C shows a Western blot demonstrating expression of the cadherin EGF LAG seven-pass G-type receptor 2 polypeptide in various cell lines. The lane order is, from left to right: 184B5, MCF7, OVCAR3, UACC62, HepG2. The three images present identical blots in which the primary antibody was used at dilutions of 1:200 (left), 1:500 (middle), and 1: 1000 (right).

For all three antibodies, the Western blots demonstrated that the antibodies bind to a polypeptide of the expected size. All of the basal marker polypeptides are expressed in a range of different cell types. While not wishing to be bound by any theory, inventors postulate that basal cells in tissues other than breast may express the basal marker genes, which may make them useful for identification of basal tumor subclasses for tumors other than breast tumors.

Example 12

Immunohistochemical Staining of Breast Tumor Arrays with Antibodies to Cytokeratin 17 Demonstrates That Cytokeratin 17 Expression Correlates with Poor Outcome Materials and Methods Tissue Arrays.

A total of 611 different paraffin embedded breast carcinoma samples were identified in the files in the Department of Pathology at the University of Basel, Women's hospital Rheinfelden, and the Kreiskrankenhaus Lorrach. The specimens were obtained from patients who underwent surgery in the period between 1985 and 1994. The histologic parameters for all cases were reviewed by a single pathologist (JT) and the histologic type and grade was determined for each case according to Elston and Ellis Elston C W, Ellis I O: Pathological prognostic factors in breast cancer. I. The value of histological grade in breast cancer: experience from a large study with long-term follow-up. *Histopathology* 1991, 19:403–10.

Follow-up was obtained for 553 cases and ranged from 1 to 151 months with a mean of 65.9 months. The use of these specimens and data for research purposes was approved by the Ethics Committee of the Basel University Hospital. Tissue arrays were constructed by obtaining 0.6 mm diameter tissue cores from each tumor and placing these cores in a new paraffin block in rows and columns as described in Kononen J, Bubendorf L, Kallioniemi A, Barlund M, Schraml P, Leighton S, Torhorst J, Mihatsch M J, Sauter G, Kallioniemi O P: Tissue microarrays for high-throughput molecular profiling of tumor specimens [see comments]. *Nat Med* 1998, 4:844–7 and in Schraml P, Kononen J, Bubendorf L, Moch H, Bissig H, Nocito A, Mihatsch M J, Kallioniemi O P, Sauter G: Tissue microarrays for gene amplification surveys in many different tumor types. *Clin Cancer Res* 1999, 5:1966–75.

Each of the 611 cases was sampled twice, once from the center of the tumor, and once from the periphery of the mass. Cores taken from the central area from each case were combined in one array and cores taken from the periphery of the tumor were combined in the other array.

Immunohistochemistry and Scoring.

Double staining of normal breast epithelium in conventional paraffin sections was performed by first staining lumenal cells with CAM5.2 using alkaline phosphatase/fast blue staining and subsequently staining basal cells with CK17 using horse radish peroxidase/DAB staining.

Sections of arrays were stained with monoclonal antibodies specific for cytokeratin 17 (DAKO, clone E3, dilution 1:10) and cytokeratin 5/6 (Boehringer Mannheim, dilution 1:10) after antigen retrieval by microwaving in citrate buffer. Note that the anti-cytokeratin 5/6 antibody used herein detects both cytokeratins 5 and 6. However, cytokeratin 5 is likely to be the major antigen recognized by this antibody in breast basal cells. Staining results were scored as follows: 1=invasive tumor cells present in tissue core and no staining seen; 2=invasive tumor cells present and weak staining; 3=invasive tumor cells present with strong staining. Only those cores containing tissue consistent with a diagnosis of invasive carcinoma were included in the outcome analysis. Cases that either had no tissue present on the array sections or cases in which the material sampled consisted of fat, fibrosis, normal breast glands, or in-situ carcinoma only, were omitted from further analysis. Cytokeratins often showed only focal staining of tumor cells within the tissue array cores or conventional paraffin sections. To account for the focal expression of CK17 and CK5/6, each of the 612 breast tumors was analyzed 4 times: with anti-CK17 and anti-CK5/6 antibody on the "central sample" array, and with anti-CK17 and anti-CK5/6 antibody on the "peripheral sample" array. A breast tumor sample was scored as staining positive for the keratins if infiltrating carcinoma in one or more of the cores from that sample reacted with either of the antibodies.

To aid in recognizing infiltrating carcinoma in the core samples, sections of each array were also stained with an anti-cytokeratin antibody mix reacting with cytokeratins 8 and 18 (CAM5.2, Becton & Dickinson, dilution 1:20) after antigen unmasking by trypsin digestion to highlight invasive carcinoma cells.

Statistical Analysis

Univariate survival analysis based upon gene expression defined subgroups of patients was performed by Kaplan-Meier statistics using WinSTAT software (www.winstat.com). Subsequent multivariate analyses were performed using Cox's proportional hazards model for survival data (Cox: Regression models and life tables. *Journal Royal Statistical Society* 1972, 74:187–220).

Results

Basal Keratin Staining in Normal Breast and Breast Carcinoma.

In normal breast, antibodies that bind to cytokeratin17 (CK17) and cytokeratin 5/6 (CK5/6) stain the basal layer of breast glandular epithelium while antibodies that bind to cytokeratins 8 and 18 stain lumenal cells (FIGS. 3C and 3D). Whole paraffin sections of breast carcinoma showed that cytokeratin 17 and 5/6 expression in paraffin embedded tissue when present was focal (FIGS. 3E and 3F) with often less than 10% of tumor cells reacting. In an attempt to study further the focal reactivity of the monoclonal antibodies against the basal type cytokeratins, and to attempt to improve the reliability of this test, rabbit antisera against CK17 were raised as described in Example 12. This serum was tested on a separate tissue array with over 300 hundred breast samples. The antiserum and the monoclonal antibody against CK17 showed highly similar reactivity with epithelial cells in the breast cores. Both reagents stained the same fraction of tumor cells suggesting that neither is a significantly better reagent. These results suggest that the focal reactivity seen with monoclonal anti-CK17 was not due to weak reactivity of the monoclonal antibody but indicates that within a tumor only a subset of tumor cells express these basal keratins, reinforcing the need for alternative basal markers.

Basal Keratin Staining on Breast Carcinoma Tissue Arrays.

Since the size of sample examined in tissue array cores is significantly smaller than on conventional samples, there was a concern that the focal reactivity of basal type cytokeratins might cause positive tumors to be missed. We decided to maximize the chance of detecting basal keratin expression in the breast tumors on the arrays by staining them with monoclonal antibodies directed at CK5/6 and CK17 and by examining arrays made with cores taken from central and peripheral areas of the tumors. By combining the results from the "central" array and the "peripheral" array, 532 tumors were available for CK17 analysis, 535 were available for CK5/6 analysis, and 564 were available for either CK17 or CK5/6. The remainder of the tumors represented on the arrays were either lost in transfer during sectioning of the tissue arrays block, or showed no convincing invasive carcinoma on the core section. Of the cases available for scoring, 75 and 63 tumors scored positive (either weak or strongly) for CK17 and CK5/6, respectively. By combining the results from the stains for CK17 and CK5/6, 90 cases (16%) out of the 564 tumors examined reacted with either CK17 and/or CK5/6. Follow-up data were available for 505 of the 564 cases on which CK staining data was obtained. The follow-up period ranged from 1 to 151 months with a mean of 66.1 months.

Figure 5A:
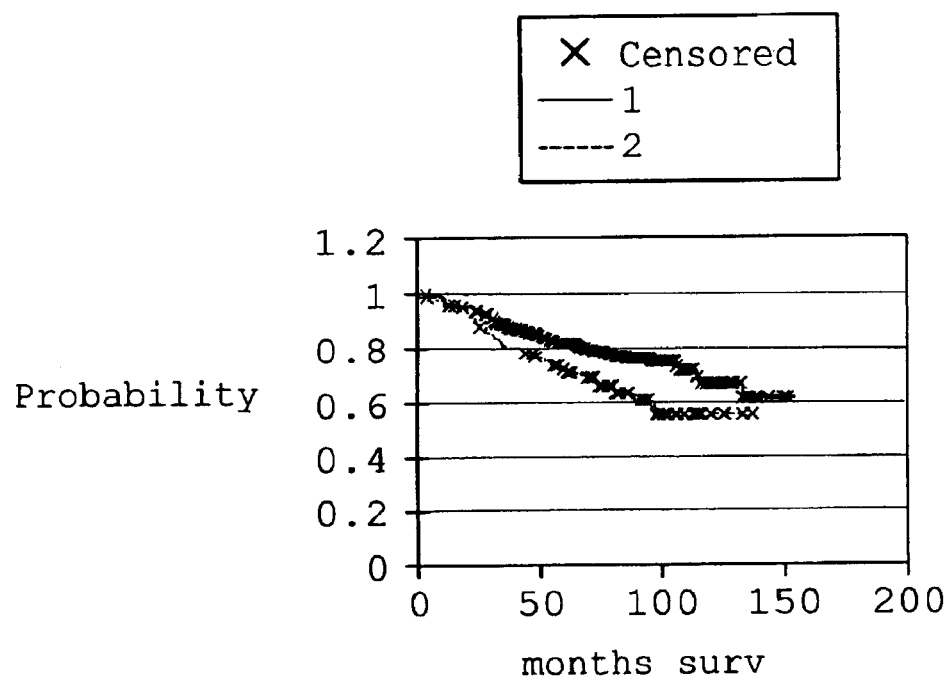
FIG. 5A shows a Kaplan-Meier survival curve demonstrating poor outcome in cytokeratin 17 and/or cytokeratin 5/6 positive tumors (p=0.012).
Figure 5B:
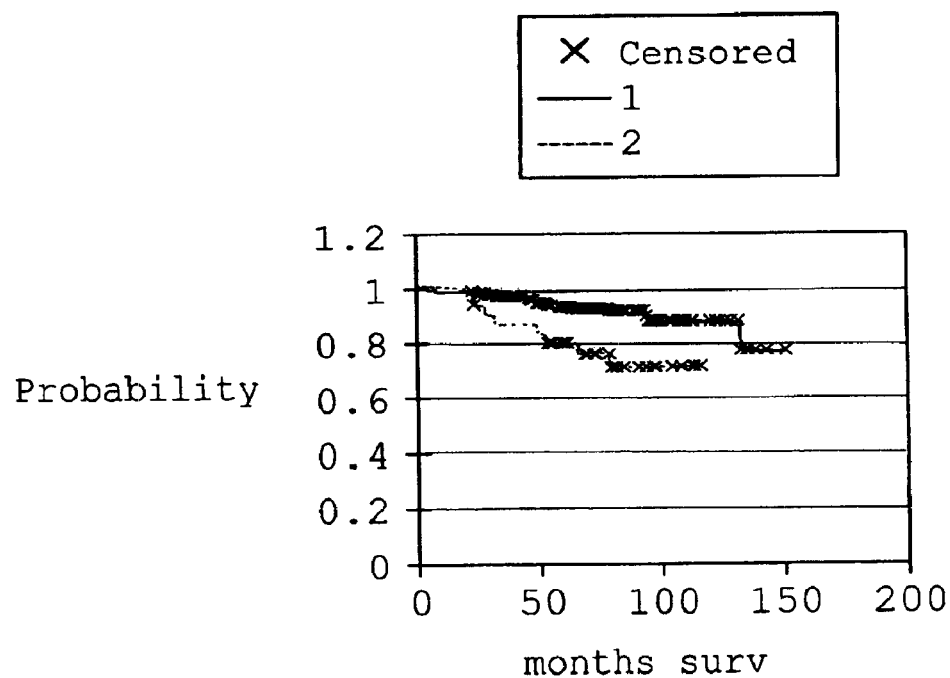
FIG. 5B shows a Kaplan-Meier survival curve demonstrating poor outcome in cytokeratin 17 and/or cytokeratin 5/6 positive tumors in lymph node negative patients (p=0.006).

Kaplan-Meier survival analysis on all patients with follow-up showed that the absence of cytokeratin 17 and cytokeratin 5 is associated with a significantly better prognosis than the presence of either of these cytokeratins (FIG. 5A, p=0.012). In the group of 229 patients with known lymph node metastases, the expression of CK17 and CK5/6 had no predictive value. In contrast, in the group of 245 patients without lymph node metastases, CK17 and/or CK5/6 expression was significantly associated with shorter survival (FIG. 5B, p=0.006). The percentage of basal keratin positive tumors was similar in patients with and without lymph node metastases. Multivariate analysis on all patients taken together showed that the prognostic association of basal cytokeratin expression with poor outcome was not independent from tumor size, LN status and histologic grade. However when analyzed on LN-negative tumors alone, the expression of basal cytokeratins is not only a statistically significant prognosticator, but is also independent of tumor size, tumor grade, her2neu status, ER status, and GATA3 status. The results clearly demonstrate the utility of cytokeratin 17 as a marker for a subclass of tumors with a poor clinical outcome while also highlighting the difficulties associated with use of anti-cytokeratin 17 antibodies.

Her2neu, Estrogen Receptor and GATA-3 Staining on Breast Carcinoma Arrays

To further confirm the accuracy of correlations between immunohistochemistry results and clinical data obtained using tissue arrays, sections of the arrays made with peripheral cores were stained for a variety of other proteins known or suspected to be associated with a good or a poor clinical outcome, for example estrogen receptor and Her2neu. As expected, expression of estrogen receptors was associated with a better clinical outcome. This finding was independent of BRE grade, LN status and size. In contrast, Her2neu expression was associated with a poor prognosis. These results are compatible with published data and are similar to those of two additional studies performed on the same breast tumor arrays. (Bucher C, Torhorst J, Kononen J, Haas P, Schraml L, Bubendorf L, Zuber M, Kochli O R, Mross F, Dieterich H, Askaa J, Godtfredsen S E, Seelig S, Moch H, Mihatsch M, Kallioniemi O, Sauter G: Prognostic significance of HER-2 amplification and overexpression in breast cancer: Methodological comparison of fluorescence in situ hybridization and immunohistochemistry using tissue microarrays of 611 primary breast cancers. in press, 2001; Torhorst J, Bucher C, Kononen J, Haas P, Zuber M, Kochli O R, Mross F, Dieterich H, Moch H, Mihatsch M, Kallioniemi O, Sauter G: Tissue microarrays for rapid linking of molecular changes to clinical endpoints. in press. 2001 )

Sections of the arrays were also stained for GATA-binding protein 3, an antigen thought to be co-expressed with estrogen receptors on the mRNA and protein level (Hoch R V, Thompson D A, Baker R J, Weigel R J: GATA-3 is expressed in association with estrogen receptor in breast cancer. *International Journal of Cancer* 1999, 84:122–8). The expression for GATA-3 was associated with a good clinical outcome and had a high correlation (Chi-square= 720.3 on 9 degrees of freedom) with estrogen receptor expression. The staining results for estrogen receptor, GATA-3 and her2neu confirm findings from prior studies, and also function as an independent validation of tissue array-based studies.

Tissue arrays present a number of advantages for tumor analysis. Analysis of large numbers of tissue sections using conventional techniques is laborious and expensive. An added disadvantage is that slides are stained in different batches, which can introduce variation in staining intensity. In addition, the analysis of large number of conventional glass slides makes comparisons between tumor samples difficult. Many of these problems are circumvented by the new technique of tissue arrays. This approach allows the efficient analysis of antibody reactivity on large numbers of tumors that are stained together on the same slide.

The tissue array studies reported here allowed separation of the patients groups into patients with lymph node metastasis and those without. In patients with metastatic disease to the lymph nodes, the expression of the basal cytokeratins was not associated with a significant difference in clinical outcome. However, in lymph node negative patients the reactivity for these markers was associated with a poor prognosis independent of tumor size, tumor grade, or immunostain reactivity for ER, her2neu or GATA3. While not wishing to be bound by any theory, taken together with the gene array data, these findings support the idea that anti-cytokeratin antibodies may identify a different type of tumor rather than just another prognostic marker and suggest the possibility that these tumors are derived from basal cells and not from lumenal cells.

Due to the focal and often weak reactivity of monoclonal antibodies against basal type keratins, the interpretation of staining results for these markers can be difficult. The intensity of staining with these markers is not comparable with other markers currently used in diagnosis of breast carcinoma, such as estrogen receptor and her2neu, a feature that prevents their use in clinical settings. We attempted to generate new reagents in the hope that they would have more robust IHC staining characteristics. Analysis of over 300 breast carcinoma samples in a separate array showed that the number of cells and the pattern of focal reactivity for the antiserum against CK17 and the intensity of staining were similar to that seen with the monoclonal antibodies. This indicates that the basal keratins are indeed only focally expressed and that the low numbers of cells stained with antibodies is not due to a weak reactivity of the monoclonal antibodies with the protein.

The studies presented here show that basal epithelial cytokeratin positive tumors occur with a significant frequency (>10%) and are associated with a poor prognosis. Patients with metastatic breast carcinoma to the axillary lymph nodes are at high risk for recurrence and most receive adjuvant therapy. The situation for node negative patients is less clear; depending on the size and grade of the tumor, the reported recurrence rate varies between 5–30%. In lymph node negative patients, the clinical decision whether to give or withhold systemic therapy thus is a difficult one and hence it is in this group of patients that the need for new prognostic markers is the greatest. The relative size of this group of patients is also expected to increase, due to continuing advances in screening and diagnostic techniques that identify increasingly smaller breast tumors. Most of these smaller tumors have not metastasized to the "sentinel" lymph node. This group of patients, therefore, has to make a difficult choice between a variety of additional therapies, such as: lumpectomy, mastectomy, chemotherapy, radiation therapy, or hormonal therapy in the absence of reliable guidance from pathologic characteristics of their tumor. The cytokeratins 17 and 5/6 appear to detect a subcategory of tumors that behave poorly and may help in treatment decisions for node-negative breast carcinoma patients. These results suggest that patients that present with basal epithelial cytokeratin expressing tumors may be candidates for more aggressive treatment procedures and also for alternate therapies directed against tumors with this particular biology.

Example 13

Immunohistochemical Staining of Normal Breast and Breast Tumor Samples in Tissue Arrays with Antibodies to Basal Marker Polypeptides Materials and Methods Tissue arrays including normal breast and breast tumor samples were prepared as described in Example 12. Monoclonal antibody to cytokeratin 5/6 (Boeringer Mannheim, Inc.) and polyclonal, affinity purified, anti-peptide antibodies to cadherin3, cadherin EGF LAG seven-pass G-type receptor 2, and matrix metalloproteinase 14 prepared as described in Example 10 were used to perform immunohistochemical staining using the DAKO Envision+, Peroxidase IHC kit (DAKO Corp., Carpenteria, Calif.) with DAB substrate according to the manufacturer's instructions.

Results

FIG. 6 shows antibody staining of normal breast tissue cores. FIG. 6A shows staining with anti-cytokeratin 5/6 monoclonal antibody (ck5/6). FIGS. 6B, 6C, and 6D show staining with anti-cadherin 3 polyclonal antibody (s0158), anti-EGF LAG seven-pass G-type receptor 2 polyclonal antibody (s0137), and anti-metalloproteinase 14 polyclonal antibody (s0144), respectively, on sections from a core derived from the same patient. The brown areas represent prominent staining of the basal layer in the two-cell layered epithelium lining the mammary gland lumen. These results confirm that the staining pattern of antibodies to the basal marker polypeptides identified herein is comparable to that of antibodies to cytokeratin 17 in terms of the cell type stained and the ability to distinguish between basal and luminal cells in the normal mammary gland.

FIG. 7 shows antibody staining of breast cancer tissue cores. FIG. 7A shows antibody staining with anti-cytokeratin 5/6 monoclonal antibody (cd5/6). FIGS. 7B and 7C show staining with anti-EGF LAG seven-pass G-type receptor 2 polyclonal antibody (s0137) and anti-cadherin 3 polyclonal antibody (s0158), respectively. The brown areas represent prominent staining of the epithelial cells within tumor tissue. Note the loss of normal breast glandular architecture consistent with the diagnosis of carcinoma.

REFERENCES

1. Tavassoli, F. A. & Schnitt, S. J. Pathology of the breast (Elsevier, New York, 1992).
2. Fambrough, D., McClure, K., Kazlauskas, A. & Lander, E. S. Diverse signaling pathways activated by growth factor receptors induce broadly overlapping, rather than independent, sets of genes [see comments]. Cell 97, 727–741 (1999).
3. Galitski, T., Saldanha, A. J., Styles, C. A., Lander, E. S. & Fink, G. R. Ploidy regulation of gene expression [see comments]. Science 285, 251–254 (1999).
4. Cho, R. J. et al. A genome-wide transcriptional analysis of the mitotic cell cycle. Mol Cell 2, 65–73 (1998).
5. Iyer, V. R. et al. The transcriptional program in the response of human fibroblasts to serum [see comments]. Science 283, 83–87 (1999).
6. Chu, S. et al. The transcriptional program of sporulation in budding yeast [published erratum appears in Science 1998 Nov 20;282(5393):1421]. Science 282, 699–705 (1998).
7. DeRisi, J. L., Iyer, V. R. & Brown, P. O. Exploring the metabolic and genetic control of gene expression on a genomic scale. Science 278, 680–686 (1997).
8. Perou, C. M. et al. Distinctive gene expression patterns in human mammary epithelial cells and breast cancers. Proc Natl Acad Sci USA 96, 9212–9217 (1999).
9. Alon, U. et al. Broad patterns of gene expression revealed by clustering analysis of tumor and normal colon tissues probed by oligonucleotide arrays. Proc Natl Acad Sci USA 96, 6745–6750 (1999).
10. Alizadeh, A. A. et al. Distinct Types of Diffuse Large B-Cell Lymphoma Identified by Gene Expression Profiling. Nature In Press (2000).
11. Golub, T. R. et al. Molecular classification of cancer: class discovery and class prediction by gene expression monitoring. Science 286, 531–537 (1999).
12. Khan, J. et al. Gene expression profiling of alveolar rhabdomyosarcoma with cDNA microarrays. Cancer Res 58, 5009–5013 (1998).
13. Pathology of familial breast cancer: differences between breast cancers in carriers of BRCA1 or BRCA2 mutations and sporadic cases. Breast Cancer Linkage Consortium [see comments]. Lancet 349, 1505–1510 (1997).
14. Andersen, T. I. et al. Prognostic significance of TP53 alterations in breast carcinoma. Br J Cancer 68, 540–548 (1993).
15. Aas, T. et al. Specific P53 mutations are associated with de novo resistance to doxorubicin in breast cancer patients. Nat Med 2, 811–814 (1996).
16. Slamon, D. J. et al. Studies of the HER-2/neu proto-oncogene in human breast and ovarian cancer. Science 244, 707–712 (1989).
17. Osborne, C. K., Yochmowitz, M. G., Knight, W. A. d. & McGuire, W. L. The value of estrogen and progesterone receptors in the treatment of breast cancer. Cancer 46, 2884–2888 (1980).
18. Ronnov-Jessen, L., Petersen, O. W. & Bissell, M. J. Cellular changes involved in conversion of normal to malignant breast: importance of the stromal reaction. Physiol Rev 76, 69–125 (1996).
19. Eisen, M. B. & Brown, P. O. DNA arrays for analysis of gene expression. Methods Enzymol 303, 179–205 (1999).
20. Eisen, M. B., Spellman, P. T., Brown, P. O. & Botstein, D. Cluster analysis and display of genome-wide expression patterns. Proc Natl Acad Sci USA 95, 14863–14868 (1998).
21. Ross, D. T. et al. Systematic Variation in Gene Expression Patterns in Human Cancer Cell Lines. Nature Genetics In Press (2000).
22. Lengauer, C., Kinzler, K. W. & Vogelstein, B. Genetic instabilities in human cancers. Nature 396, 643–649 (1998).
23. Cahill, D. P. et al. Mutations of mitotic checkpoint genes in human cancers [see comments]. Nature 392, 300–303 (1998).
24. Li, Y. & Benezra, R. Identification of a human mitotic checkpoint gene: hsMAD2. Science 274, 246–248 (1996).
25. Zhou, H. et al. Tumour amplified kinase STK15/BTAK induces centrosome amplification, aneuploidy and transformation [see comments]. Nat Genet 20, 189–193 (1998).
26. Wolf, G. et al. Prognostic significance of polo-like kinase (PLK) expression in non-small cell lung cancer. Oncogene 14, 543–549 (1997).
27. Yang, G. P., Ross, D. T., Kuang, W. W., Brown, P. O. & Weigel, R. J. Combining SSH and cDNA microarrays for rapid identification of differentially expressed genes [In Process Citation]. Nucleic Acids Res 27, 1517–1523 (1999).
28. Hoch, R. V., Thompson, D. A., Baker, R. J. & Weigel, R. J. GATA-3 is expressed in association with estrogen receptor in breast cancer. Int J Cancer 84, 122–128 (1999).
29. Prud'homme, J. F. et al. Cloning of a gene expressed in human breast cancer and regulated by estrogen in MCF-7 cells. Dna 4, 11–21 (1985).
30. Bhargava, V., Kell, D. L., van de Rijn, M. & Wamke, R. A. Bcl-2 immunoreactivity in breast carcinoma correlates with hormone receptor positivity. Am J Pathol 145, 535–540 (1994).
31. Leek, R. D., Kaklamanis, L., Pezzella, F., Gatter, K. C. & Harris, A. L. bcl-2 in normal human breast and carcinoma, association with oestrogen receptor-positive, epidermal growth factor receptor-negative tumours and in situ cancer. Br J Cancer 69, 135–139 (1994).
32. Pauletti, G., Godolphin, W., Press, M. F. & Slamon, D. J. Detection and quantitation of HER-2/neu gene amplification in human breast cancer archival material using fluorescence in situ hybridization. Oncogene 13, 63–72 (1996).
33. Pollack, J. R. et al. Genome-wide analysis of DNA copy-number changes using cDNA microarrays. Nat Genet 23, 41–46 (1999).
34. Stein, D. et al. The SH2 domain protein GRB-7 is co-amplified, overexpressed and in a tight complex with HER2 in breast cancer. Embo J 13, 1331–1340 (1994).
35. Moog-Lutz, C. et al. MLN64 exhibits homology with the steroidogenic acute regulatory protein (STAR) and is over-expressed in human breast carcinomas. Int J Cancer 71, 183–191 (1997).
36. Miettinen, M., Lindenmayer, A. E. & Chaubal, A. Endothelial cell markers CD31, CD34, and BNH9 antibody to H- and Y- antigens—evaluation of their specificity and sensitivity in the diagnosis of vascular tumors and comparison with von Willebrand factor. Mod Pathol 7, 82–90 (1994).
37. Abbas, A. K., Lichtman, A. H. & Pober, J. S. Cellular and molecular immunology (Saunders, Philadelphia, 1991).
38. Baxa, C. A. et al. Human adipocyte lipid-binding protein: purification of the protein and cloning of its complementary DNA. Biochemistry 28, 8683–8690 (1989).
39. Tontonoz, P., Hu, E., Graves, R. A., Budavari, A. I. & Spiegelman, B. M. mPPAR gamma 2: tissue-specific regulator of an adipocyte enhancer. Genes Dev 8, 1224–1234 (1994).
40. Stampfer, M.
41. Dairkee, S. H., Mayall, B. H., Smith, H. S. & Hackett, A. J. Monoclonal marker that predicts early recurrence of breast cancer [letter]. Lancet 1, 514 (1987).
42. Dairkee, S. H., Puett, L. & Hackett, A. J. Expression of basal and luminal epithelium-specific keratins in normal, benign, and malignant breast tissue. J Natl Cancer Inst 80, 691–695 (1988).
43. Malzahn, K., Mitze, M., Thoenes, M. & Moll, R. Biological and prognostic significance of stratified epithelial cytokeratins in infiltrating ductal breast carcinomas. Virchows Arch 433, 119–129 (1998).
44. Guelstein, V. I. et al. Monoclonal antibody mapping of keratins 8 and 17 and of vimentin in normal human mammary gland, benign tumors, dysplasias and breast cancer. Int J Cancer 42, 147–153 (1988).
45. Gusterson, B. A. et al. Distribution of myoepithelial cells and basement membrane proteins in the normal breast and in benign and malignant breast diseases. Cancer Res 42, 4763–4770 (1982).
46. Nagle, R. B. et al. Characterization of breast carcinomas by two monoclonal antibodies distinguishing myoepithelial from luminal epithelial cells. J Histochem Cytochem 34, 869–881 (1986).
47. Dairkee, S. H., Ljung, B. M., Smith, H. & Hackett, A. Immunolocalization of a human basal epithelium specific keratin in benign and malignant breast disease. Breast Cancer Res Treat 10, 11–20 (1987).
48. Berns, E. M. et al. Prevalence of amplification of the oncogenes c-myc, HER2/neu, and int-2 in one thousand human breast tumours: correlation with steroid receptors. Eur J Cancer 28, 697–700 (1992).
49. Heintz, N. H., Leslie, K. O., Rogers, L. A. & Howard, P. L. Amplification of the c-erb B-2 oncogene and prognosis of breast adenocarcinoma. Arch Pathol Lab Med 114, 160–163 (1990).
50. Guerin, M., Barrois, M., Terrier, M. J., Spielmann, M. & Riou, G. Overexpression of either c-myc or c-erbB-2/neu proto-oncogenes in human breast carcinomas: correlation with poor prognosis. Oncogene Res 3, 21–31 (1988).
51. Wang, K. et al. Monitoring gene expression profile changes in ovarian carcinomas using cDNA microarray [In Process Citation]. Gene 229, 101–108 (1999).
52. Spellman, P T, et al., Comprehensive identification of cell cycle-regulated genes of the yeast *Saccharomyces cerevisiae* by microarray hybridization, *Mol Biol Cell*, 9(12):3273–97, 1998.
53. Berx, G., Staes, K., van Hengel, J., Molemans, F., Bussemakers, M. J. G., van Bokhoven, A. & van Roy, F. (1995). Cloning and characterization of the invasion suppressor gene E-cadherin (CDH1). Genomics, 26, 281–289.
54. Islam, S., Carey, T. E., Wolf, G. T., Wheelock, M. J. Johnson, K. R. (1996). Expression of N-Cadherin by human squamous carcinomacells induces a scattered fibroblastic phenotype with disrupted cell-cell adhesion. J. Cell Biol. 136, 1643–1654.
55. Lee S W (1996) H-cadherin, a novel cadherin with growth inhibitory functions and diminished expression in human breast cancer. Nat Med 2:7 776–82

56. Lee, S. W., Reimer, C. L., Campbell, D. B., Cheresh, P., Duda, R. B. & Kocher, O. (1998). H-cadherin expression inhibits in vitro invasiveness and tumor formation in vivo. Carcinogenesis, 19, 1157–1159.
57. Nollet F, Berx G, van Roy F (1999) The role of the E-cadherin/catenin adhesion complex in the development and progression of cancer. Mol Cell Biol Res Commun 2:2 77–85
58. Nollet F, Berx G, van Roy F (2000) Phylogenetic Analysis of the Cadherin Superfamily allows Identification of Six Major Subfamilies Besides Several Solitary Members. JMB 299, 551–572
59. Paul, R., Ewing, C. M., Robinson, J. C., Marshall, F. F., Johnson, K. R., Wheelock, M. J. & Isaacs, W. B. (1997). Cadherin-6, a cell adhesion molecule specifically expressed in the proximal renal tubule and renal cell carcinoma. Cancer Res. 57, 2741–2748.
60. Sato M, Mori Y, Sakurada A, Fujimura S, Horii A (1998) The H-cadherin (CDH13) gene is inactivated in human lung cancer. Hum Genet 103:1 96–101
61. Shimazui, T., Giroldi, L. A., Bringuier, P. P., Oosterwijk, E. & Schalken, J. A. (1996). Complex cadherin expression in renal cell carcinoma. Cancer Res. 56, 3234–3237.

What is claimed is:

1. A method of classifying a breast tumor comprising the steps of:

providing a breast tumor sample;

detecting expression or activity of a gene encoding the polypeptide of SEQ ID NO:3 in the sample; and classifying the tumor as belonging to a tumor subclass based on the results of the detecting step.

2. The method of claim 1, wherein the detecting step comprises detecting the polypeptide of SEQ ID NO:3.

3. The method of claim 2, wherein the polypeptide is detected by performing immunohistochemical analysis on the sample using an antibody that specifically binds to the polypeptide.

4. The method of claim 2, wherein the polypeptide is detected by performing an ELISA assay using an antibody that specifically binds to the polypeptide.

5. The method of claim 2, wherein the polypeptide is detected using an antibody array comprising an antibody that specifically binds to the polypeptide.

6. The method of claim 2, wherein the polypeptide is detected by detecting modification of a substrate by the polypeptide.

7. The method of claim 1, wherein, in the step of providing, the sample is isolated from a subject having a tumor, the method further comprising:

stratifying the subject having the tumor for a clinical trial based on the results of the classifying step.

8. The method of claim 1, wherein the tumor subclass is a basal tumor subclass.

9. A method of providing diagnostic, prognostic, or predictive information for a breast tumor comprising steps of:

providing a breast tumor sample;

detecting expression or activity of a gene encoding the polypeptide of SEQ ID NO:3 in the sample;

classifying the tumor as belonging to a tumor subclass based on the results of the detecting step; and providing diagnostic, prognostic, or predictive information based on the classifying step.

10. The method of claim 9 wherein the detecting step comprises detecting the polypeptide of SEQ ID NO:3.

11. The method of claim 10, wherein the polypeptide is detected by performing immunohistochemical analysis on the sample using an antibody that specifically binds to the polypeptide.

12. The method of claim 10, wherein the polypeptide is detected by performing an ELISA assay using an antibody that specifically binds to the polypeptide.

13. The method of claim 10, wherein the polypeptide is detected using an antibody array comprising an antibody that specifically binds to the polypeptide.

14. The method of claim 10, wherein the polypeptide is detected by detecting modification of a substrate by the polypeptide.

15. The method of claim 9, wherein the tumor subclass is a basal tumor subclass.

16. A method of selecting a treatment for a breast tumor comorising steps of:

providing a breast tumor sample;

detecting expression or activity of a gene encoding the polypeptide of SEQ ID NO:3 in the sample;

classifying the tumor as belonging to a tumor subclass based on the results of the detecting step; and selecting a treatment based on the classifying step.

17. The method of claim 16 wherein the detecting step comprises detecting the polypeptide of SEQ ID NO:3.

18. The method of claim 17, wherein the polypeptide is detected by performing immunohistochemical analysis on the sample using an antibody that specifically binds to the polypeptide.

19. The method of claim 17, wherein the polypeptide is detected by performing an ELISA assay using an antibody that specifically binds to the polypeptide.

20. The method of claim 17, wherein the polypeptide is detected using an antibody array comprising an antibody that specifically binds to the polypeptide.

21. The method of claim 17, wherein the polypeptide is detected by detecting modification of a substrate by the polypeptide.

22. The method of claim 16, wherein the tumor subclass is a basal tumor subclass.

23. A method of providing diagnostic, prognostic, or predictive information about a subject having a breast tumor comprising steps of:
   providing a sample isolated from a subject having a breast tumor;
   detecting expression or activity of a gene encoding the polypeptide of SEQ ID NO:3 in the sample; and
   providing diagnostic, prognostic, or predictive information about the subject based on the results of the detecting step.

24. The method of claim 23, wherein the detecting step comprises detecting the polypeptide of SEQ ID NO:3.

25. The method of claim 24, wherein the polypeptide is detected by performing immnunohistochemical analysis on the sample using an antibody that specifically binds to the polypeptide.

26. The method of claim 24, wherein the polypeptide is detected by performing an ELISA assay using an antibody that specifically binds to the polypeptide.

27. The method of claim 24, wherein the polypeptide is detected using an antibody array comprising an antibody that specifically binds to the polypeptide.

28. The method of claim 24, wherein the polypeptide is detected by detecting modification of a substrate by the polypeptide.

29. The method of claim 23, wherein the sample is selected from the group consisting of:
   a blood sample, a urine sample, a serum sample, an ascites sample, a saliva sample, a cell, and a portion of tissue.

30. The method of claim 23, wherein the sample is a tumor sample.

31. A method of stratifying a subject having a breast tumor for a clinical trial comprising steps of:
   providing a sample isolated from a subject having a breast tumor;
   detecting expression or activity of a gene encoding the polypeptide of SEQ ID NO:3 in the sample; and
   stratifying the subject for a clinical trial based on the results of the detecting step.

32. The method of claim 31, wherein the detecting step comprises detecting the polypeptide or polypeptides.

33. The method of claim 32, wherein the polypeptide is detected by performing immunohistochemical analysis on the sample using an antibody that specifically binds to the polypeptide.

34. The method of claim 32, wherein the polypeptide is detected by performing an ELISA assay using an antibody that specifically binds to the polypeptide.

35. The method of claim 32, wherein the polypeptide is detected using an antibody array comprising an antibody that specifically binds to the polypeptide.

36. The method of claim 32, wherein the polypeptide is detected by detecting modification of a substrate by the polypeptide.

37. The method of claim 31, wherein the sample is selected from the group consisting of:
   a blood sample, a urine sample, a serum sample, an ascites sample, a saliva sample, a cell, and a portion of tissue.

38. The method of claim 31, wherein the sample is a tumor sample.

39. A method of selecting a treatment for a subject having a breast tumor comprising steps of:
   providing a sample isolated from a subject having a breast tumor;
   detecting expression or activity of a gene encoding the polypeptide of SEQ ID NO:3 in the sample; and
   selecting a treatment based on the results of the detecting step.

40. The method of claim 39, wherein the detecting step comprises detecting the polypeptide of SEQ ID NO:3.

41. The method of claim 40, wherein the polypeptide is detected by performing immunohistochemical analysis on the sample using an antibody that specifically binds to the polypeptide.

42. The method of claim 40, wherein the polypeptide is detected by performing an ELISA assay using an antibody that specifically binds to the polypeptide.

43. The method of claim 40, wherein the polypeptide is detected using an antibody array comprising an antibody that specifically binds to the polypeptide.

44. The method of claim 40, wherein the polypeptide is detected by detecting modification of a substrate by the polypeptide.

45. The method of claim 39, wherein the sample is selected from the group consisting of:
   a blood sample, a urine sample, a serum sample, an ascites sample, a saliva sample, a cell, and a portion of tissue.

46. The method of claim 39, wherein the sample is a tumor sample.

* * * * *

SEQUENCE LISTING

<160> NUMBER OF SEQ ID NOS: 15

<210> SEQ ID NO 1
<211> LENGTH: 829
<212> TYPE: PRT
<213> ORGANISM: Artificial Sequence
<220> FEATURE:
<223> OTHER INFORMATION: Description of Artificial Sequence:Sequence of Cadherin 3

<400> SEQUENCE: 1

```
Met Gly Leu Pro Arg Gly Pro Leu Ala Ser Leu Leu Leu Leu Gln Val
 1               5                  10                  15

Cys Trp Leu Gln Cys Ala Ala Ser Glu Pro Cys Arg Ala Val Phe Arg
            20                  25                  30

Glu Ala Glu Val Thr Leu Glu Ala Gly Gly Ala Glu Gln Glu Pro Gly
        35                  40                  45

Gln Ala Leu Gly Lys Val Phe Met Gly Cys Pro Gly Gln Glu Pro Ala
    50                  55                  60

Leu Phe Ser Thr Asp Asn Asp Asp Phe Thr Val Arg Asn Gly Glu Thr
65                  70                  75                  80

Val Gln Glu Arg Arg Ser Leu Lys Glu Arg Asn Pro Leu Lys Ile Phe
                85                  90                  95

Pro Ser Lys Arg Ile Leu Arg Arg His Lys Arg Asp Trp Val Val Ala
            100                 105                 110

Pro Ile Ser Val Pro Glu Asn Gly Lys Gly Pro Phe Pro Gln Arg Leu
        115                 120                 125

Asn Gln Leu Lys Ser Asn Lys Asp Arg Asp Thr Lys Ile Phe Tyr Ser
    130                 135                 140

Ile Thr Gly Pro Gly Ala Asp Ser Pro Pro Glu Gly Val Phe Ala Val
145                 150                 155                 160

Glu Lys Glu Thr Gly Trp Leu Leu Leu Asn Lys Pro Leu Asp Arg Glu
                165                 170                 175

Glu Ile Ala Lys Tyr Glu Leu Phe Gly His Ala Val Ser Glu Asn Gly
            180                 185                 190

Ala Ser Val Glu Asp Pro Met Asn Ile Ser Ile Ile Val Thr Asp Gln
        195                 200                 205

Asn Asp His Lys Pro Lys Phe Thr Gln Asp Thr Phe Arg Gly Ser Val
    210                 215                 220

Leu Glu Gly Val Leu Pro Gly Thr Ser Val Met Gln Val Thr Ala Thr
225                 230                 235                 240

Asp Glu Asp Asp Ala Ile Tyr Thr Tyr Asn Gly Val Val Ala Tyr Ser
                245                 250                 255
```

```
Ile His Ser Gln Glu Pro Lys Asp Pro His Asp Leu Met Phe Thr Ile
        260                 265                 270

His Arg Ser Thr Gly Thr Ile Ser Val Ile Ser Ser Gly Leu Asp Arg
            275                 280                 285

Glu Lys Val Pro Glu Tyr Thr Leu Thr Ile Gln Ala Thr Asp Met Asp
    290                 295                 300

Gly Asp Gly Ser Thr Thr Thr Ala Val Ala Val Val Glu Ile Leu Asp
305                 310                 315                 320

Ala Asn Asp Asn Ala Pro Met Phe Asp Pro Gln Lys Tyr Glu Ala His
                325                 330                 335

Val Pro Glu Asn Ala Val Gly His Glu Val Gln Arg Leu Thr Val Thr
            340                 345                 350

Asp Leu Asp Ala Pro Asn Ser Pro Ala Trp Arg Ala Thr Tyr Leu Ile
        355                 360                 365

Met Gly Gly Asp Asp Gly Asp His Phe Thr Ile Thr Thr His Pro Glu
370                 375                 380

Ser Asn Gln Gly Ile Leu Thr Thr Arg Lys Gly Leu Asp Phe Glu Ala
385                 390                 395                 400

Lys Asn Gln His Thr Leu Tyr Val Glu Val Thr Asn Glu Ala Pro Phe
                405                 410                 415

Val Leu Lys Leu Pro Thr Ser Thr Ala Thr Ile Val Val His Val Glu
            420                 425                 430

Asp Val Asn Glu Ala Pro Val Phe Val Pro Pro Ser Lys Val Val Glu
        435                 440                 445

Val Gln Glu Gly Ile Pro Thr Gly Glu Pro Val Cys Val Tyr Thr Ala
    450                 455                 460

Glu Asp Pro Asp Lys Glu Asn Gln Lys Ile Ser Tyr Arg Ile Leu Arg
465                 470                 475                 480

Asp Pro Ala Gly Trp Leu Ala Met Asp Pro Asp Ser Gly Gln Val Thr
                485                 490                 495

Ala Val Gly Thr Leu Asp Arg Glu Asp Glu Gln Phe Val Arg Asn Asn
            500                 505                 510

Ile Tyr Glu Val Met Val Leu Ala Met Asp Asn Gly Ser Pro Pro Thr
        515                 520                 525

Thr Gly Thr Gly Thr Leu Leu Leu Thr Leu Ile Asp Val Asn Asp His
    530                 535                 540

Gly Pro Val Pro Glu Pro Arg Gln Ile Thr Ile Cys Asn Gln Ser Pro
545                 550                 555                 560

Val Arg His Val Leu Asn Ile Thr Asp Lys Asp Leu Ser Pro His Thr
                565                 570                 575

Ser Pro Phe Gln Ala Gln Leu Thr Asp Asp Ser Asp Ile Tyr Trp Thr
            580                 585                 590

Ala Glu Val Asn Glu Glu Gly Asp Thr Val Val Leu Ser Leu Lys Lys
        595                 600                 605

Phe Leu Lys Gln Asp Thr Tyr Asp Val His Leu Ser Leu Ser Asp His
    610                 615                 620

Gly Asn Lys Glu Gln Leu Thr Val Ile Arg Ala Thr Val Cys Asp Cys
625                 630                 635                 640

His Gly His Val Glu Thr Cys Pro Gly Pro Trp Lys Gly Gly Phe Ile
                645                 650                 655

Leu Pro Val Leu Gly Ala Val Leu Ala Leu Leu Phe Leu Leu Leu Val
            660                 665                 670
```

```
Leu Leu Leu Leu Val Arg Lys Lys Arg Lys Ile Lys Glu Pro Leu Leu
            675                 680                 685

Leu Pro Glu Asp Asp Thr Arg Asp Asn Val Phe Tyr Tyr Gly Glu Glu
        690                 695                 700

Gly Gly Gly Glu Glu Asp Gln Asp Tyr Asp Ile Thr Gln Leu His Arg
705                 710                 715                 720

Gly Leu Glu Ala Arg Pro Glu Val Val Leu Arg Asn Asp Val Ala Pro
                725                 730                 735

Thr Ile Ile Pro Thr Pro Met Tyr Arg Pro Arg Pro Ala Asn Pro Asp
            740                 745                 750

Glu Ile Gly Asn Phe Ile Ile Glu Asn Leu Lys Ala Ala Asn Thr Asp
        755                 760                 765

Pro Thr Ala Pro Pro Tyr Asp Thr Leu Leu Val Phe Asp Tyr Glu Gly
    770                 775                 780

Ser Gly Ser Asp Ala Ala Ser Leu Ser Ser Leu Thr Ser Ser Ala Ser
785                 790                 795                 800

Asp Gln Asp Gln Asp Tyr Asp Tyr Leu Asn Glu Trp Gly Ser Arg Phe
                805                 810                 815

Lys Lys Leu Ala Asp Met Tyr Gly Gly Gly Glu Asp Asp
            820                 825

<210> SEQ ID NO 2
<211> LENGTH: 582
<212> TYPE: PRT
<213> ORGANISM: Artificial Sequence
<220> FEATURE:
<223> OTHER INFORMATION: Description of Artificial Sequence:Matrix
      Metalloproteinase

<400> SEQUENCE: 2

Met Ser Pro Ala Pro Arg Pro Pro Arg Cys Leu Leu Leu Pro Leu Leu
 1               5                  10                  15

Thr Leu Gly Thr Ala Leu Ala Ser Leu Gly Ser Ala Gln Ser Ser Ser
            20                  25                  30

Phe Ser Pro Glu Ala Trp Leu Gln Gln Tyr Gly Tyr Leu Pro Pro Gly
        35                  40                  45

Asp Leu Arg Thr His Thr Gln Arg Ser Pro Gln Ser Leu Ser Ala Ala
    50                  55                  60

Ile Ala Ala Met Gln Lys Phe Tyr Gly Leu Gln Val Thr Gly Lys Ala
65                  70                  75                  80

Asp Ala Asp Thr Met Lys Ala Met Arg Arg Pro Arg Cys Gly Val Pro
                85                  90                  95

Asp Lys Phe Gly Ala Glu Ile Lys Ala Asn Val Arg Arg Lys Arg Tyr
            100                 105                 110

Ala Ile Gln Gly Leu Lys Trp Gln His Asn Glu Ile Thr Phe Cys Ile
        115                 120                 125

Gln Asn Tyr Thr Pro Lys Val Gly Glu Tyr Ala Thr Tyr Glu Ala Ile
    130                 135                 140

Arg Lys Ala Phe Arg Val Trp Glu Ser Ala Thr Pro Leu Arg Phe Arg
145                 150                 155                 160

Glu Val Pro Tyr Ala Tyr Ile Arg Glu Gly His Glu Lys Gln Ala Asp
                165                 170                 175

Ile Met Ile Phe Phe Ala Glu Gly Phe His Gly Asp Ser Thr Pro Phe
            180                 185                 190
```

```
Asp Gly Glu Gly Gly Phe Leu Ala His Ala Tyr Phe Pro Gly Pro Asn
            195                 200                 205
Ile Gly Gly Asp Thr His Phe Asp Ser Ala Glu Pro Trp Thr Val Arg
        210                 215                 220
Asn Glu Asp Leu Asn Gly Asn Asp Ile Phe Leu Val Ala Val His Glu
225                 230                 235                 240
Leu Gly His Ala Leu Gly Leu Glu His Ser Ser Asp Pro Ser Ala Ile
                245                 250                 255
Met Ala Pro Phe Tyr Gln Trp Met Asp Thr Glu Asn Phe Val Leu Pro
            260                 265                 270
Asp Asp Arg Arg Gly Ile Gln Gln Leu Tyr Gly Gly Glu Ser Gly
        275                 280                 285
Phe Pro Thr Lys Met Pro Pro Gln Pro Arg Thr Thr Ser Arg Pro Ser
    290                 295                 300
Val Pro Asp Lys Pro Lys Asn Pro Thr Tyr Gly Pro Asn Ile Cys Asp
305                 310                 315                 320
Gly Asn Phe Asp Thr Val Ala Met Leu Arg Gly Glu Met Phe Val Phe
                325                 330                 335
Lys Glu Arg Trp Phe Trp Arg Val Arg Asn Asn Gln Val Met Asp Gly
            340                 345                 350
Tyr Pro Met Pro Ile Gly Gln Phe Trp Arg Gly Leu Pro Ala Ser Ile
        355                 360                 365
Asn Thr Ala Tyr Glu Arg Lys Asp Gly Lys Phe Val Phe Phe Lys Gly
370                 375                 380
Asp Lys His Trp Val Phe Asp Glu Ala Ser Leu Glu Pro Gly Tyr Pro
385                 390                 395                 400
Lys His Ile Lys Glu Leu Gly Arg Gly Leu Pro Thr Asp Lys Ile Asp
                405                 410                 415
Ala Ala Leu Phe Trp Met Pro Asn Gly Lys Thr Tyr Phe Phe Arg Gly
            420                 425                 430
Asn Lys Tyr Tyr Arg Phe Asn Glu Glu Leu Arg Ala Val Asp Ser Glu
        435                 440                 445
Tyr Pro Lys Asn Ile Lys Val Trp Glu Gly Ile Pro Glu Ser Pro Arg
    450                 455                 460
Gly Ser Phe Met Gly Ser Asp Glu Val Phe Thr Tyr Phe Tyr Lys Gly
465                 470                 475                 480
Asn Lys Tyr Trp Lys Phe Asn Asn Gln Lys Leu Lys Val Glu Pro Gly
                485                 490                 495
Tyr Pro Lys Ser Ala Leu Arg Asp Trp Met Gly Cys Pro Ser Gly Gly
            500                 505                 510
Arg Pro Asp Glu Gly Thr Glu Glu Thr Glu Val Ile Ile Ile Glu
        515                 520                 525
Val Asp Glu Glu Gly Gly Ala Val Ser Ala Ala Val Val Leu
    530                 535                 540
Pro Val Leu Leu Leu Leu Leu Val Leu Ala Val Gly Leu Ala Val Phe
545                 550                 555                 560
Phe Phe Arg Arg His Gly Thr Pro Arg Arg Leu Leu Tyr Cys Gln Arg
                565                 570                 575
Ser Leu Leu Asp Lys Val
            580

<210> SEQ ID NO 3
<211> LENGTH: 2923
```

```
<212> TYPE: PRT
<213> ORGANISM: Artificial Sequence
<220> FEATURE:
<223> OTHER INFORMATION: Description of Artificial Sequence:Cadherin EGF
      LAG Seven Pass G-Type Receptor 2

<400> SEQUENCE: 3
```

Met Arg Ser Pro Ala Thr Gly Val Pro Leu Pro Thr Pro Pro Pro
 1               5                  10                  15

Leu Leu Leu Leu Leu Leu Leu Leu Pro Pro Leu Leu Gly Asp
            20                  25                  30

Gln Val Gly Pro Cys Arg Ser Leu Gly Ser Arg Gly Arg Gly Ser Ser
            35                  40                  45

Gly Ala Cys Ala Pro Met Gly Trp Leu Cys Pro Ser Ser Ala Ser Asn
        50                  55                  60

Leu Trp Leu Tyr Thr Ser Arg Cys Arg Asp Ala Gly Thr Glu Leu Thr
 65                  70                  75                  80

Gly His Leu Val Pro His His Asp Gly Leu Arg Val Trp Cys Pro Glu
                85                  90                  95

Ser Glu Ala His Ile Pro Leu Pro Pro Ala Pro Glu Gly Cys Pro Trp
            100                 105                 110

Ser Cys Arg Leu Leu Gly Ile Gly Gly His Leu Ser Pro Gln Gly Lys
        115                 120                 125

Leu Thr Leu Pro Glu Glu His Pro Cys Leu Lys Ala Pro Arg Leu Arg
130                 135                 140

Cys Gln Ser Cys Lys Leu Ala Gln Ala Pro Gly Leu Arg Ala Gly Glu
145                 150                 155                 160

Arg Ser Pro Glu Glu Ser Leu Gly Gly Arg Arg Lys Arg Asn Val Asn
                165                 170                 175

Thr Ala Pro Gln Phe Gln Pro Pro Ser Tyr Gln Ala Thr Val Pro Glu
            180                 185                 190

Asn Gln Pro Ala Gly Thr Pro Val Ala Ser Leu Arg Ala Ile Asp Pro
        195                 200                 205

Asp Glu Gly Glu Ala Gly Arg Leu Glu Tyr Thr Met Asp Ala Leu Phe
210                 215                 220

Asp Ser Arg Ser Asn Gln Phe Phe Ser Leu Asp Pro Val Thr Gly Ala
225                 230                 235                 240

Val Thr Thr Ala Glu Glu Leu Asp Arg Glu Thr Lys Ser Thr His Val
                245                 250                 255

Phe Arg Val Thr Ala Gln Asp His Gly Met Pro Arg Arg Ser Ala Leu
            260                 265                 270

Ala Thr Leu Thr Ile Leu Val Thr Asp Thr Asn Asp His Asp Pro Val
        275                 280                 285

Phe Glu Gln Gln Glu Tyr Lys Glu Ser Leu Arg Glu Asn Leu Glu Val
290                 295                 300

Gly Tyr Glu Val Leu Thr Val Arg Ala Thr Asp Gly Asp Ala Pro Pro
305                 310                 315                 320

Asn Ala Asn Ile Leu Tyr Arg Leu Leu Glu Gly Ser Gly Gly Ser Pro
                325                 330                 335

Ser Glu Val Phe Glu Ile Asp Pro Arg Ser Gly Val Ile Arg Thr Arg
            340                 345                 350

Gly Pro Val Asp Arg Glu Glu Val Glu Ser Tyr Gln Leu Thr Val Glu
        355                 360                 365

Ala Ser Asp Gln Gly Arg Asp Pro Gly Pro Arg Ser Thr Thr Ala Ala
370                 375                 380

-continued

```
Val Phe Leu Ser Val Glu Asp Asn Asp Asn Ala Pro Gln Phe Ser
385                 390                 395                 400

Glu Lys Arg Tyr Val Val Gln Val Arg Glu Asp Val Thr Pro Gly Ala
            405                 410                 415

Pro Val Leu Arg Val Thr Ala Ser Asp Arg Asp Lys Gly Ser Asn Ala
            420                 425                 430

Val Val His Tyr Ser Ile Met Ser Gly Asn Ala Arg Gly Gln Phe Tyr
            435                 440                 445

Leu Asp Ala Gln Thr Gly Ala Leu Asp Val Val Ser Pro Leu Asp Tyr
    450                 455                 460

Glu Thr Thr Lys Glu Tyr Thr Leu Arg Val Arg Ala Gln Asp Gly Gly
465                 470                 475                 480

Arg Pro Pro Leu Ser Asn Val Ser Gly Leu Val Thr Val Gln Val Leu
                485                 490                 495

Asp Ile Asn Asp Asn Ala Pro Ile Phe Val Ser Thr Pro Phe Gln Ala
                500                 505                 510

Thr Val Leu Glu Ser Val Pro Leu Gly Tyr Leu Val Leu His Val Gln
            515                 520                 525

Ala Ile Asp Ala Asp Ala Gly Asp Asn Ala Arg Leu Glu Tyr Arg Leu
    530                 535                 540

Ala Gly Val Gly His Asp Phe Pro Phe Thr Ile Asn Asn Gly Thr Gly
545                 550                 555                 560

Trp Ile Ser Val Ala Ala Glu Leu Asp Arg Glu Glu Val Asp Phe Tyr
                565                 570                 575

Ser Phe Gly Val Glu Ala Arg Asp His Gly Thr Pro Ala Leu Thr Ala
                580                 585                 590

Ser Ala Ser Val Ser Val Thr Val Leu Asp Val Asn Asp Asn Asn Pro
            595                 600                 605

Thr Phe Thr Gln Pro Glu Tyr Thr Val Arg Leu Asn Glu Asp Ala Ala
    610                 615                 620

Val Gly Thr Ser Val Val Thr Val Ser Ala Val Asp Arg Asp Ala His
625                 630                 635                 640

Ser Val Ile Thr Tyr Gln Ile Thr Ser Gly Asn Thr Arg Asn Arg Phe
                645                 650                 655

Ser Ile Thr Ser Gln Ser Gly Gly Leu Val Ser Leu Ala Leu Pro
                660                 665                 670

Leu Asp Tyr Lys Leu Glu Arg Gln Tyr Val Leu Ala Val Thr Ala Ser
            675                 680                 685

Asp Gly Thr Arg Gln Asp Thr Ala Gln Ile Val Val Asn Val Thr Asp
    690                 695                 700

Ala Asn Thr His Arg Pro Val Phe Gln Ser Ser His Tyr Thr Val Asn
705                 710                 715                 720

Val Asn Glu Asp Arg Pro Ala Gly Thr Thr Val Val Leu Ile Ser Ala
                725                 730                 735

Thr Asp Glu Asp Thr Gly Glu Asn Ala Arg Ile Thr Tyr Phe Met Glu
            740                 745                 750

Asp Ser Ile Pro Gln Phe Arg Ile Asp Ala Asp Thr Gly Ala Val Thr
            755                 760                 765

Thr Gln Ala Glu Leu Asp Tyr Glu Asp Gln Val Ser Tyr Thr Leu Ala
    770                 775                 780

Ile Thr Ala Arg Asp Asn Gly Ile Pro Gln Lys Ser Asp Thr Thr Tyr
785                 790                 795                 800
```

-continued

Leu Glu Ile Leu Val Asn Asp Val Asn Asp Asn Ala Pro Gln Phe Leu
              805                 810                 815

Arg Asp Ser Tyr Gln Gly Ser Val Tyr Glu Asp Val Pro Pro Phe Thr
          820                 825                 830

Ser Val Leu Gln Ile Ser Ala Thr Asp Arg Asp Ser Gly Leu Asn Gly
          835                 840                 845

Arg Val Phe Tyr Thr Phe Gln Gly Gly Asp Asp Gly Asp Gly Asp Phe
      850                 855                 860

Ile Val Glu Ser Thr Ser Gly Ile Val Arg Thr Leu Arg Arg Leu Asp
865                 870                 875                 880

Arg Glu Asn Val Ala Gln Tyr Val Leu Arg Ala Tyr Ala Val Asp Lys
                  885                 890                 895

Gly Met Pro Pro Ala Arg Thr Pro Met Glu Val Thr Val Thr Val Leu
              900                 905                 910

Asp Val Asn Asp Asn Pro Pro Val Phe Glu Gln Asp Glu Phe Asp Val
          915                 920                 925

Phe Val Glu Glu Asn Ser Pro Ile Gly Leu Ala Val Ala Arg Val Thr
      930                 935                 940

Ala Thr Asp Pro Asp Glu Gly Thr Asn Ala Gln Ile Met Tyr Gln Ile
945                 950                 955                 960

Val Glu Gly Asn Ile Pro Glu Val Phe Gln Leu Asp Ile Phe Ser Gly
                  965                 970                 975

Glu Leu Thr Ala Leu Val Asp Leu Asp Tyr Glu Asp Arg Pro Glu Tyr
              980                 985                 990

Val Leu Val Ile Gln Ala Thr Ser Ala Pro Leu Val Ser Arg Ala Thr
          995                 1000                1005

Val His Val Arg Leu Leu Asp Arg Asn Asp Asn Pro Pro Val Leu Gly
      1010                1015                1020

Asn Phe Glu Ile Leu Phe Asn Asn Tyr Val Thr Asn Arg Ser Ser Ser
1025                1030                1035                1040

Phe Pro Gly Gly Ala Ile Gly Arg Val Pro Ala His Asp Pro Asp Ile
              1045                1050                1055

Ser Asp Ser Leu Thr Tyr Ser Phe Glu Arg Gly Asn Glu Leu Ser Leu
          1060                1065                1070

Val Leu Leu Asn Ala Ser Thr Gly Glu Leu Lys Leu Ser Arg Ala Leu
      1075                1080                1085

Asp Asn Asn Arg Pro Leu Glu Ala Ile Met Ser Val Leu Val Ser Asp
      1090                1095                1100

Gly Val His Ser Val Thr Ala Gln Cys Ala Leu Arg Val Thr Ile Ile
1105                1110                1115                1120

Thr Asp Glu Met Leu Thr His Ser Ile Thr Leu Arg Leu Glu Asp Met
              1125                1130                1135

Ser Pro Glu Arg Phe Leu Ser Pro Leu Leu Gly Leu Phe Ile Gln Ala
          1140                1145                1150

Val Ala Ala Thr Leu Ala Thr Pro Pro Asp His Val Val Phe Asn
      1155                1160                1165

Val Gln Arg Asp Thr Asp Ala Pro Gly Gly His Ile Leu Asn Val Ser
      1170                1175                1180

Leu Ser Val Gly Gln Pro Pro Gly Pro Gly Gly Gly Pro Pro Phe Leu
      1185                1190                1195                1200

Pro Ser Glu Asp Leu Gln Glu Arg Leu Tyr Leu Asn Arg Ser Leu Leu
          1205                1210                1215

-continued

```
Thr Ala Ile Ser Ala Gln Arg Val Leu Pro Phe Asp Asp Asn Ile Cys
        1220                1225                1230
Leu Arg Glu Pro Cys Glu Asn Tyr Met Arg Cys Val Ser Val Leu Arg
    1235                1240                1245
Phe Asp Ser Ser Ala Pro Phe Ile Ala Ser Ser Val Leu Phe Arg
1250                1255                1260
Pro Ile His Pro Val Gly Gly Leu Arg Cys Arg Cys Pro Pro Gly Phe
1265                1270                1275                1280
Thr Gly Asp Tyr Cys Glu Thr Glu Val Asp Leu Cys Tyr Ser Arg Pro
        1285                1290                1295
Cys Gly Pro His Gly Arg Cys Arg Ser Arg Glu Gly Gly Tyr Thr Cys
    1300                1305                1310
Leu Cys Arg Asp Gly Tyr Thr Gly Glu His Cys Glu Val Ser Ala Arg
        1315                1320                1325
Ser Gly Arg Cys Thr Pro Gly Val Cys Lys Asn Gly Gly Thr Cys Val
    1330                1335                1340
Asn Leu Leu Val Gly Gly Phe Lys Cys Asp Cys Pro Ser Gly Asp Phe
1345                1350                1355                1360
Glu Lys Pro Tyr Cys Gln Val Thr Thr Arg Ser Phe Pro Ala His Ser
        1365                1370                1375
Phe Ile Thr Phe Arg Gly Leu Arg Gln Arg Phe His Phe Thr Leu Ala
        1380                1385                1390
Leu Ser Phe Ala Thr Lys Glu Arg Asp Gly Leu Leu Leu Tyr Asn Gly
        1395                1400                1405
Arg Phe Asn Glu Lys His Asp Phe Val Ala Leu Glu Val Ile Gln Glu
    1410                1415                1420
Gln Val Gln Leu Thr Phe Ser Ala Gly Glu Ser Thr Thr Thr Val Ser
1425                1430                1435                1440
Pro Phe Val Pro Gly Gly Val Ser Asp Gly Gln Trp His Thr Val Gln
        1445                1450                1455
Leu Lys Tyr Tyr Asn Lys Pro Leu Leu Gly Gln Thr Gly Leu Pro Gln
        1460                1465                1470
Gly Pro Ser Glu Gln Lys Val Ala Val Val Thr Val Asp Gly Cys Asp
    1475                1480                1485
Thr Gly Val Ala Leu Arg Phe Gly Ser Val Leu Gly Asn Tyr Ser Cys
    1490                1495                1500
Ala Ala Gln Gly Thr Gln Gly Gly Ser Lys Lys Ser Leu Asp Leu Thr
1505                1510                1515                1520
Gly Pro Leu Leu Leu Gly Gly Val Pro Asp Leu Pro Glu Ser Phe Pro
        1525                1530                1535
Val Arg Met Arg Gln Phe Val Gly Cys Met Arg Asn Leu Gln Val Asp
        1540                1545                1550
Ser Arg His Ile Asp Met Ala Asp Phe Ile Ala Asn Asn Gly Thr Val
        1555                1560                1565
Pro Gly Cys Pro Ala Lys Lys Asn Val Cys Asp Ser Asn Thr Cys His
    1570                1575                1580
Asn Gly Gly Thr Cys Val Asn Gln Trp Asp Ala Phe Ser Cys Glu Cys
1585                1590                1595                1600
Pro Leu Gly Phe Gly Gly Lys Ser Cys Ala Gln Glu Met Ala Asn Pro
        1605                1610                1615
Gln His Phe Leu Gly Ser Ser Leu Val Ala Trp His Gly Leu Ser Leu
        1620                1625                1630
```

-continued

Pro Ile Ser Gln Pro Trp Tyr Leu Ser Leu Met Phe Arg Thr Arg Gln
     1635                1640                1645

Ala Asp Gly Val Leu Gln Ala Ile Thr Arg Gly Arg Ser Thr Ile
1650                1655                1660

Thr Leu Gln Leu Arg Glu Gly His Val Met Leu Ser Val Glu Gly Thr
1665                1670                1675                1680

Gly Leu Gln Ala Ser Ser Leu Arg Leu Glu Pro Gly Arg Ala Asn Asp
         1685                1690                1695

Gly Asp Trp His His Ala Gln Leu Ala Leu Gly Ala Ser Gly Gly Pro
         1700                1705                1710

Gly His Ala Ile Leu Ser Phe Asp Tyr Gly Gln Gln Arg Ala Glu Gly
         1715                1720                1725

Asn Leu Gly Pro Arg Leu His Gly Leu His Leu Ser Asn Ile Thr Val
         1730                1735                1740

Gly Gly Ile Pro Gly Pro Ala Gly Gly Val Ala Arg Gly Phe Arg Gly
1745                1750                1755                1760

Cys Leu Gln Gly Val Arg Val Ser Asp Thr Pro Glu Gly Val Asn Ser
              1765                1770                1775

Leu Asp Pro Ser His Gly Glu Ser Ile Asn Val Glu Gln Gly Cys Ser
              1780                1785                1790

Leu Pro Asp Pro Cys Asp Ser Asn Pro Cys Pro Ala Asn Ser Tyr Cys
              1795                1800                1805

Ser Asn Asp Trp Asp Ser Tyr Ser Cys Ser Cys Asp Pro Gly Tyr Tyr
              1810                1815                1820

Gly Asp Asn Cys Thr Asn Val Cys Asp Leu Asn Pro Cys Glu His Gln
1825                1830                1835                1840

Ser Val Cys Thr Arg Lys Pro Ser Ala Pro His Gly Tyr Thr Cys Glu
              1845                1850                1855

Cys Pro Pro Asn Tyr Leu Gly Pro Tyr Cys Glu Thr Arg Ile Asp Gln
              1860                1865                1870

Pro Cys Pro Arg Gly Trp Trp Gly His Pro Thr Cys Gly Pro Cys Asn
         1875                1880                1885

Cys Asp Val Ser Lys Gly Phe Asp Pro Asp Cys Asn Lys Thr Ser Gly
    1890                1895                1900

Glu Cys His Cys Lys Glu Asn His Tyr Arg Pro Pro Gly Ser Pro Thr
1905                1910                1915                1920

Cys Leu Leu Cys Asp Cys Tyr Pro Thr Gly Ser Leu Ser Arg Val Cys
         1925                1930                1935

Asp Pro Glu Asp Gly Gln Cys Pro Cys Lys Pro Gly Val Ile Gly Arg
         1940                1945                1950

Gln Cys Asp Arg Cys Asp Asn Pro Phe Ala Glu Val Thr Thr Asn Gly
         1955                1960                1965

Cys Glu Val Asn Tyr Asp Ser Cys Pro Arg Ala Ile Glu Ala Gly Ile
    1970                1975                1980

Trp Trp Pro Arg Thr Arg Phe Gly Leu Pro Ala Ala Ala Pro Cys Pro
1985                1990                1995                2000

Lys Gly Ser Phe Gly Thr Ala Val Arg His Cys Asp Glu His Arg Gly
              2005                2010                2015

Trp Leu Pro Pro Asn Leu Phe Asn Cys Thr Ser Ile Thr Phe Ser Glu
              2020                2025                2030

Leu Lys Gly Phe Ala Glu Arg Leu Gln Arg Asn Glu Ser Gly Leu Asp
         2035                2040                2045

Ser Gly Arg Ser Gln Gln Leu Ala Leu Leu Leu Arg Asn Ala Thr Gln

-continued

```
             2050                2055                2060
His Thr Ala Gly Tyr Phe Gly Ser Asp Val Lys Val Ala Tyr Gln Leu
     2065                2070                2075                2080
Ala Thr Arg Leu Leu Ala His Glu Ser Thr Gln Arg Gly Phe Gly Leu
             2085                2090                2095
Ser Ala Thr Gln Asp Val His Phe Thr Glu Asn Leu Leu Arg Val Gly
     2100                2105                2110
Ser Ala Leu Leu Asp Thr Ala Asn Lys Arg His Trp Glu Leu Ile Gln
         2115                2120                2125
Gln Thr Glu Gly Gly Thr Ala Trp Leu Leu Gln His Tyr Glu Ala Tyr
     2130                2135                2140
Ala Ser Ala Leu Ala Gln Asn Met Arg His Thr Tyr Leu Ser Pro Phe
2145                2150                2155                2160
Thr Ile Val Thr Pro Asn Ile Val Ile Ser Val Val Arg Leu Asp Lys
             2165                2170                2175
Gly Asn Phe Ala Gly Ala Lys Leu Pro Arg Tyr Glu Ala Leu Arg Gly
         2180                2185                2190
Glu Gln Pro Pro Asp Leu Glu Thr Thr Val Ile Leu Pro Glu Ser Val
         2195                2200                2205
Phe Arg Glu Thr Pro Pro Val Val Arg Pro Ala Gly Pro Gly Glu Ala
     2210                2215                2220
Gln Glu Pro Glu Glu Leu Ala Arg Arg Gln Arg Arg His Pro Glu Leu
2225                2230                2235                2240
Ser Gln Gly Glu Ala Val Ala Ser Val Ile Ile Tyr Arg Thr Leu Ala
         2245                2250                2255
Gly Leu Leu Pro His Asn Tyr Asp Pro Asp Lys Arg Ser Leu Arg Val
         2260                2265                2270
Pro Lys Arg Pro Ile Ile Asn Thr Pro Val Val Ser Ile Ser Val His
             2275                2280                2285
Asp Asp Glu Glu Leu Leu Pro Arg Ala Leu Asp Lys Pro Val Thr Val
         2290                2295                2300
Gln Phe Arg Leu Leu Glu Thr Glu Glu Arg Thr Lys Pro Ile Cys Val
2305                2310                2315                2320
Phe Trp Asn His Ser Ile Leu Val Ser Gly Thr Gly Gly Trp Ser Ala
             2325                2330                2335
Arg Gly Cys Glu Val Val Phe Arg Asn Glu Ser His Val Ser Cys Gln
             2340                2345                2350
Cys Asn His Met Thr Ser Phe Ala Val Leu Met Asp Val Ser Arg Arg
         2355                2360                2365
Glu Asn Gly Glu Ile Leu Pro Leu Lys Thr Leu Thr Tyr Val Ala Leu
     2370                2375                2380
Gly Val Thr Leu Ala Ala Leu Leu Leu Thr Phe Phe Leu Thr Leu
2385                2390                2395                2400
Leu Arg Ile Leu Arg Ser Asn Gln His Gly Ile Arg Arg Asn Leu Thr
             2405                2410                2415
Ala Ala Leu Gly Leu Ala Gln Leu Val Phe Leu Leu Gly Ile Asn Gln
         2420                2425                2430
Ala Asp Leu Pro Phe Ala Cys Thr Val Ile Ala Ile Leu Leu His Phe
         2435                2440                2445
Leu Tyr Leu Cys Thr Phe Ser Trp Ala Leu Leu Glu Ala Leu His Leu
     2450                2455                2460
Tyr Arg Ala Leu Thr Glu Val Arg Asp Val Asn Thr Gly Pro Met Arg
2465                2470                2475                2480
```

```
Phe Tyr Tyr Met Leu Gly Trp Gly Val Pro Ala Phe Ile Thr Gly Leu
            2485                2490                2495

Ala Val Gly Leu Asp Pro Glu Gly Tyr Gly Asn Pro Asp Phe Cys Trp
        2500                2505                2510

Leu Ser Ile Tyr Asp Thr Leu Ile Trp Ser Phe Ala Gly Pro Val Ala
        2515                2520                2525

Phe Ala Val Ser Met Ser Val Phe Leu Tyr Ile Leu Ala Ala Arg Ala
        2530                2535                2540

Ser Cys Ala Ala Gln Arg Gln Gly Phe Glu Lys Lys Gly Pro Val Ser
2545                2550                2555                2560

Gly Leu Gln Pro Ser Phe Ala Val Leu Leu Leu Ser Ala Thr Trp
            2565                2570                2575

Leu Leu Ala Leu Leu Ser Val Asn Ser Asp Thr Leu Leu Phe His Tyr
            2580                2585                2590

Leu Phe Ala Thr Cys Asn Cys Ile Gln Gly Pro Phe Ile Phe Leu Ser
            2595                2600                2605

Tyr Val Val Leu Ser Lys Glu Val Arg Lys Ala Leu Lys Leu Ala Cys
            2610                2615                2620

Ser Arg Lys Pro Ser Pro Asp Pro Ala Leu Thr Thr Lys Ser Thr Leu
2625                2630                2635                2640

Thr Ser Ser Tyr Asn Cys Pro Ser Pro Tyr Ala Asp Gly Arg Leu Tyr
            2645                2650                2655

Gln Pro Tyr Gly Asp Ser Ala Gly Ser Leu His Ser Thr Ser Arg Ser
            2660                2665                2670

Gly Lys Ser Gln Pro Ser Tyr Ile Pro Phe Leu Leu Arg Glu Glu Ser
            2675                2680                2685

Ala Leu Asn Pro Gly Gln Gly Pro Pro Gly Leu Gly Asp Pro Gly Ser
            2690                2695                2700

Leu Phe Leu Glu Gly Gln Asp Gln Gln His Asp Pro Asp Thr Asp Ser
2705                2710                2715                2720

Asp Ser Asp Leu Ser Leu Glu Asp Asp Gln Ser Gly Ser Tyr Ala Ser
            2725                2730                2735

Thr His Ser Ser Asp Ser Glu Glu Glu Glu Glu Glu Glu Glu Glu
            2740                2745                2750

Ala Ala Phe Pro Gly Glu Gln Gly Trp Asp Ser Leu Leu Gly Pro Gly
            2755                2760                2765

Ala Glu Arg Leu Pro Leu His Ser Thr Pro Lys Asp Gly Gly Pro Gly
            2770                2775                2780

Pro Gly Lys Ala Pro Trp Pro Gly Asp Phe Gly Thr Thr Ala Lys Glu
2785                2790                2795                2800

Ser Ser Gly Asn Gly Ala Pro Glu Glu Arg Leu Arg Glu Asn Gly Asp
            2805                2810                2815

Ala Leu Ser Arg Glu Gly Ser Leu Gly Pro Leu Pro Gly Ser Ser Ala
            2820                2825                2830

Gln Pro His Lys Gly Ile Leu Lys Lys Cys Leu Pro Thr Ile Ser
            2835                2840                2845

Glu Lys Ser Ser Leu Leu Arg Leu Pro Leu Glu Gln Cys Thr Gly Ser
            2850                2855                2860

Ser Arg Gly Ser Ser Ala Ser Glu Gly Ser Arg Gly Gly Pro Pro Pro
2865                2870                2875                2880

Arg Pro Pro Pro Arg Gln Ser Leu Gln Glu Gln Leu Asn Gly Val Met
            2885                2890                2895
```

-continued

Pro Ile Ala Met Ser Ile Lys Ala Gly Thr Val Asp Glu Asp Ser Ser
            2900                2905                2910

Gly Ser Glu Phe Leu Phe Phe Asn Phe Leu His
        2915                2920

<210> SEQ ID NO 4
<211> LENGTH: 19
<212> TYPE: PRT
<213> ORGANISM: Artificial Sequence
<220> FEATURE:
<223> OTHER INFORMATION: Description of Artificial Sequence:Peptides for
      Antibodies that Bind to Cadherin 3

<400> SEQUENCE: 4

Arg Ala Val Phe Arg Glu Ala Glu Val Thr Leu Glu Ala Gly Gly Ala
  1               5                  10                  15

Glu Gln Glu

<210> SEQ ID NO 5
<211> LENGTH: 17
<212> TYPE: PRT
<213> ORGANISM: Artificial Sequence
<220> FEATURE:
<223> OTHER INFORMATION: Description of Artificial Sequence:Peptides for
      Antibodies that Bind to Cadherin 3

<400> SEQUENCE: 5

Gln Glu Pro Ala Leu Phe Ser Thr Asp Asn Asp Asp Phe Thr Val Arg
  1               5                  10                  15

Asn

<210> SEQ ID NO 6
<211> LENGTH: 15
<212> TYPE: PRT
<213> ORGANISM: Artificial Sequence
<220> FEATURE:
<223> OTHER INFORMATION: Description of Artificial Sequence:Peptides for
      Antibodies that Bind to Cadherin 3

<400> SEQUENCE: 6

Gln Lys Tyr Glu Ala His Val Pro Glu Asn Ala Val Gly His Glu
  1               5                  10                  15

<210> SEQ ID NO 7
<211> LENGTH: 19
<212> TYPE: PRT
<213> ORGANISM: Artificial Sequence
<220> FEATURE:
<223> OTHER INFORMATION: Description of Artificial Sequence:Peptides for
      Antibodies that Bind to Matrix Metalloproteinase
      14

<400> SEQUENCE: 7

Ala Tyr Ile Arg Glu Gly His Glu Lys Gln Ala Asp Ile Met Ile Phe
  1               5                  10                  15

Phe Ala Glu

<210> SEQ ID NO 8
<211> LENGTH: 18
<212> TYPE: PRT
<213> ORGANISM: Artificial Sequence
<220> FEATURE:
<223> OTHER INFORMATION: Description of Artificial Sequence:Peptides for
      Antibodies that Bind to Matrix Metalloporteinase

<400> SEQUENCE: 8

-continued

```
Asp Glu Ala Ser Leu Glu Pro Gly Tyr Pro Lys His Ile Lys Glu Leu
  1               5                  10                  15

Gly Arg

<210> SEQ ID NO 9
<211> LENGTH: 16
<212> TYPE: PRT
<213> ORGANISM: Artificial Sequence
<220> FEATURE:
<223> OTHER INFORMATION: Description of Artificial Sequence:Peptides for
      Antibodies that bind to Matrix Metalloporteinase

<400> SEQUENCE: 9

Arg Gly Ser Phe Met Gly Ser Asp Glu Val Phe Thr Tyr Phe Tyr Lys
  1               5                  10                  15

<210> SEQ ID NO 10
<211> LENGTH: 18
<212> TYPE: PRT
<213> ORGANISM: Artificial Sequence
<220> FEATURE:
<223> OTHER INFORMATION: Description of Artificial Sequence: Peptides
      for Antibodies that Bind to Anti-Cadherin EGF LAG
      Seven-Pass G-Type Receptor 2

<400> SEQUENCE: 10

Gln Ala Ser Ser Leu Arg Leu Glu Pro Gly Arg Ala Asn Asp Gly Asp
  1               5                  10                  15

Trp His

<210> SEQ ID NO 11
<211> LENGTH: 20
<212> TYPE: PRT
<213> ORGANISM: Artificial Sequence
<220> FEATURE:
<223> OTHER INFORMATION: Description of Artificial Sequence:Peptides for
      Antibodies that bind to Anti-Cadherin EGF LAG
      Seven-Pass G-Type Receptor 2

<400> SEQUENCE: 11

Glu Leu Lys Gly Phe Ala Glu Arg Leu Gln Arg Asn Glu Ser Gly Leu
  1               5                  10                  15

Asp Ser Gly Arg
            20

<210> SEQ ID NO 12
<211> LENGTH: 17
<212> TYPE: PRT
<213> ORGANISM: Artificial Sequence
<220> FEATURE:
<223> OTHER INFORMATION: Description of Artificial Sequence: Peptides
      for Antibodies that Bind to Anti-Cadherin EGF LAG
      Seven-Pass G-Type Receptor 2

<400> SEQUENCE: 12

Arg Ser Gly Lys Ser Gln Pro Ser Tyr Ile Pro Phe Leu Leu Arg Glu
  1               5                  10                  15

Glu

<210> SEQ ID NO 13
<211> LENGTH: 16
<212> TYPE: PRT
<213> ORGANISM: Artificial Sequence
<220> FEATURE:
<223> OTHER INFORMATION: Description of Artificial Sequence:Peptides for
```

-continued

```
       Antibodies that Bind to Anti-Cytokeratin 17

<400> SEQUENCE: 13

Lys Lys Glu Pro Val Thr Thr Arg Gln Val Arg Thr Ile Val Glu Glu
  1               5                  10                  15

<210> SEQ ID NO 14
<211> LENGTH: 17
<212> TYPE: PRT
<213> ORGANISM: Artificial Sequence
<220> FEATURE:
<223> OTHER INFORMATION: Description of Artificial Sequence:Peptides for
      Antibodies that Bind to Anti-Cytokeratin 17

<400> SEQUENCE: 14

Gln Asp Gly Lys Val Ile Ser Ser Arg Glu Gln Val His Gln Thr Thr
  1               5                  10                  15

Arg

<210> SEQ ID NO 15
<211> LENGTH: 15
<212> TYPE: PRT
<213> ORGANISM: Artificial Sequence
<220> FEATURE:
<223> OTHER INFORMATION: Description of Artificial Sequence: Peptides
      for Antibodies that Bind to Anti-Cytokeratin 17

<400> SEQUENCE: 15

Ser Ser Ser Ile Lys Gly Ser Ser Gly Leu Gly Gly Gly Ser Ser
  1               5                  10                  15
```